US011229391B2

United States Patent
Drakulic et al.

(10) Patent No.: US 11,229,391 B2
(45) Date of Patent: Jan. 25, 2022

(54) APPARATUS FOR PROCESSING BIOMEDICAL SIGNALS FOR DISPLAY

(71) Applicant: BioSig Technologies, Inc., Westport, CT (US)

(72) Inventors: Budimir S. Drakulic, Los Angeles, CA (US); Sina Fakhar, Encino, CA (US); Thomas G. Foxall, Surrey (CA); Branislav Vlajinic, Los Angeles, CA (US)

(73) Assignee: BioSig Technologies, Inc., Westport, CT (US)

( * ) Notice: Subject to any disclaimer, the term of this patent is extended or adjusted under 35 U.S.C. 154(b) by 0 days.

(21) Appl. No.: 17/130,842

(22) Filed: Dec. 22, 2020

(65) Prior Publication Data

US 2021/0112014 A1 Apr. 15, 2021

Related U.S. Application Data

(60) Division of application No. 16/866,195, filed on May 4, 2020, now Pat. No. 10,911,365, which is a
(Continued)

(51) Int. Cl.
*A61B 5/30* (2021.01)
*A61B 5/00* (2006.01)
(Continued)

(52) U.S. Cl.
CPC .............. *A61B 5/30* (2021.01); *A61B 5/0245* (2013.01); *A61B 5/308* (2021.01); *A61B 5/318* (2021.01);
(Continued)

(58) Field of Classification Search
CPC .................... H04L 47/50; H04L 43/02; H04L 2924/14335; A61B 5/0215; A61B 5/0245;
(Continued)

(56) References Cited

U.S. PATENT DOCUMENTS

| 4,360,030 A | 11/1982 | Citron et al. |
| 5,025,784 A | 6/1991 | Shao et al. |

(Continued)

FOREIGN PATENT DOCUMENTS

| CN | 103201800 A | 7/2013 |
| CN | 105517616 A | 4/2016 |

(Continued)

OTHER PUBLICATIONS

Badran, et al., Neurophysiologic Effects of Transcutaneous Auricular Vagus Nerve Stimulation (taVNS) Via Electrical Stimulation of the Tragus: A Concurrent taVNS/fMRI Study and Review, Brain Stimulation, vol. 11, No. 3, May-Jun. 2018, pp. 492-500.

(Continued)

*Primary Examiner* — Jung Kim
(74) *Attorney, Agent, or Firm* — Sterne, Kessler, Goldstein & Fox P.L.L.C.

(57) ABSTRACT

Apparatus and methods remove a voltage offset from an electrical signal, specifically a biomedical signal. A signal is received at a first operational amplifier and is amplified by a gain. An amplitude of the signal is monitored, by a first pair of diode stages coupled to an output of the first operational amplifier, for the voltage offset. The amplitude of the signal is then attenuated by the first pair of diode stages and a plurality of timing banks. The attenuating includes limiting charging, by the first pair of diode stages, of the plurality of timing banks and setting a time constant based on the charging. The attenuating removes the voltage offset persisting at a threshold for a duration of at least the time constant. Saturation of the signal is limited to a saturation recovery time while the saturated signal is gradually pulled into monitoring range over the saturation recovery time.

9 Claims, 66 Drawing Sheets

Related U.S. Application Data continuation of application No. 16/718,996, filed on Dec. 18, 2019, now Pat. No. 10,841,232, which is a division of application No. 16/195,562, filed on Nov. 19, 2018, now Pat. No. 10,686,715.

(60) Provisional application No. 62/669,345, filed on May 9, 2018.

(51) Int. Cl.

| | | |
|---|---|---|
| *A61B 5/0245* | (2006.01) | |
| *A61B 5/318* | (2021.01) | |
| *A61B 5/308* | (2021.01) | |
| H04L 12/26 | (2006.01) | |
| H04L 12/863 | (2013.01) | |
| G16H 40/63 | (2018.01) | |
| A61B 18/00 | (2006.01) | |
| H02H 9/04 | (2006.01) | |
| H03F 3/45 | (2006.01) | |
| H03F 3/68 | (2006.01) | |
| H03K 5/125 | (2006.01) | |
| A61B 5/0215 | (2006.01) | |
| A61B 5/024 | (2006.01) | |
| A61B 5/0538 | (2021.01) | |
| A61B 18/14 | (2006.01) | |
| A61B 5/361 | (2021.01) | |
| A61B 5/363 | (2021.01) | |
| A61B 5/352 | (2021.01) | |
| A61B 5/366 | (2021.01) | |

(52) U.S. Cl.
CPC .......... *A61B 5/7203* (2013.01); *A61B 5/7225* (2013.01); *A61B 5/7246* (2013.01); *A61B 5/0006* (2013.01); *A61B 5/0215* (2013.01); *A61B 5/02405* (2013.01); *A61B 5/0538* (2013.01); *A61B 5/352* (2021.01); *A61B 5/361* (2021.01); *A61B 5/363* (2021.01); *A61B 5/366* (2021.01); *A61B 5/4836* (2013.01); *A61B 5/7217* (2013.01); *A61B 5/742* (2013.01); *A61B 5/7435* (2013.01); *A61B 18/1492* (2013.01); *A61B 2018/00351* (2013.01); *A61B 2018/00577* (2013.01); *A61B 2562/18* (2013.01); *A61B 2562/223* (2013.01); *G16H 40/63* (2018.01); *H01L 2924/14335* (2013.01); *H02H 9/04* (2013.01); *H02H 9/045* (2013.01); *H03F 3/45* (2013.01); *H03F 3/45475* (2013.01); *H03F 3/68* (2013.01); *H03F 2200/129* (2013.01); *H03F 2200/171* (2013.01); *H03F 2200/234* (2013.01); *H03F 2200/375* (2013.01); *H03F 2200/451* (2013.01); *H03F 2203/45116* (2013.01); *H03F 2203/45528* (2013.01); *H03F 2203/45601* (2013.01); *H03K 5/125* (2013.01); *H04L 43/02* (2013.01); *H04L 47/50* (2013.01)

(58) Field of Classification Search
CPC ... A61B 5/046; A61B 5/0464; A61B 18/1492; A61B 5/0428; A61B 5/4836; A61B 5/7217; A61B 5/7225; A61B 5/7435; A61B 5/7203; A61B 5/742; A61B 5/7246; A61B 5/0402; A61B 5/02405; A61B 5/0456; A61B 5/0472; A61B 5/0538; A61B 2018/00351; A61B 2018/00577; A61B 2562/18; A61B 2562/223; A61B 5/0006; A61B 5/7221; A61B 5/04017; H03F 3/45475; H03F 3/45; H03F 3/68; H03F 2200/171; H03F 2200/234; H03F 2200/451; H03F 2200/129; H03F 2200/375; H03F 2203/45116; H03F 2203/45528; H03F 2203/45601; H03K 5/125; G16H 40/63; H02H 9/045; H02H 9/04
See application file for complete search history.

(56) References Cited

U.S. PATENT DOCUMENTS

| | | |
|---|---|---|
| 5,381,803 A | 1/1995 | Herleikson et al. |
| RE35,122 E | 12/1995 | Corenman et al. |
| 5,511,553 A | 4/1996 | Segalowitz |
| 5,555,285 A | 9/1996 | Tapia et al. |
| 5,651,010 A | 7/1997 | Kostreski et al. |
| 5,908,393 A | 6/1999 | Albrecht et al. |
| 6,027,500 A | 2/2000 | Buckles et al. |
| 6,085,347 A | 7/2000 | Du et al. |
| 6,405,227 B1 | 6/2002 | Prakash |
| 6,496,712 B1 | 12/2002 | Dahl et al. |
| 6,545,213 B1 | 4/2003 | Gabriel |
| 6,563,545 B1 | 5/2003 | Masumoto |
| 6,695,838 B2 | 2/2004 | Wellman et al. |
| 6,807,195 B1 | 10/2004 | Moore, Jr. et al. |
| 6,871,084 B1 | 3/2005 | Kingsley et al. |
| 6,892,093 B2 | 5/2005 | Brodnick |
| 7,072,709 B2 | 7/2006 | Xue |
| 7,094,235 B2 | 8/2006 | Francischelli |
| 7,146,213 B1 | 12/2006 | Levine |
| 7,174,210 B1 | 2/2007 | Levine |
| 7,196,892 B2 | 3/2007 | Gabriel |
| 7,256,638 B2 | 8/2007 | Vice |
| 7,263,397 B2 | 8/2007 | Hauck et al. |
| 7,282,049 B2 | 10/2007 | Orszulak et al. |
| 7,367,972 B2 | 5/2008 | Francischelli et al. |
| 7,502,642 B2 | 3/2009 | Boese et al. |
| 7,613,499 B2 | 11/2009 | Rahn et al. |
| 7,694,917 B2 | 4/2010 | Gabriel |
| RE41,334 E | 5/2010 | Beatty et al. |
| 7,783,339 B2 | 8/2010 | Lee et al. |
| 7,806,829 B2 | 10/2010 | Hauck |
| 7,824,399 B2 | 11/2010 | Francischelli et al. |
| 7,824,403 B2 | 11/2010 | Vaska et al. |
| 7,881,778 B2 | 2/2011 | Rantala |
| 8,021,361 B2 | 9/2011 | Paul et al. |
| 8,157,848 B2 | 4/2012 | Zhang et al. |
| 8,211,096 B2 | 7/2012 | Pless et al. |
| 8,221,402 B2 | 7/2012 | Francischelli et al. |
| 8,221,415 B2 | 7/2012 | Francischelli |
| 8,290,578 B2 | 10/2012 | Schneider |
| 8,396,541 B2 | 3/2013 | Zhang |
| 8,403,925 B2 | 3/2013 | Miller et al. |
| 8,406,866 B2 | 3/2013 | Deno et al. |
| 8,406,875 B2 | 3/2013 | Levin et al. |
| 8,433,398 B2 | 4/2013 | Zhang |
| 8,449,535 B2 | 5/2013 | Deno et al. |
| 8,475,440 B2 | 7/2013 | Abboud et al. |
| 8,521,262 B2 | 8/2013 | Webler |
| 8,583,220 B2 | 11/2013 | Schwartz |
| 8,603,084 B2 | 12/2013 | Fish et al. |
| 8,620,978 B2 | 12/2013 | Koyrakh |
| 8,632,582 B2 | 1/2014 | Levy |
| 8,641,705 B2 | 2/2014 | Leo et al. |
| 8,647,284 B2 | 2/2014 | Afonso |
| 8,658,892 B2 | 2/2014 | Gabriel |
| 8,675,996 B2 | 3/2014 | Liao et al. |
| 8,676,315 B2 | 3/2014 | Warner et al. |
| 8,721,636 B2 | 5/2014 | Vaska et al. |
| 8,755,860 B2 | 6/2014 | Paul et al. |
| 8,795,270 B2 | 8/2014 | Drake |
| 8,801,707 B2 | 8/2014 | Francischelli et al. |
| 8,825,148 B2 | 9/2014 | Zhang et al. |
| 8,834,461 B2 | 9/2014 | Wereth et al. |
| 8,849,387 B2 | 9/2014 | Gilbert et al. |
| 8,868,168 B2 | 10/2014 | Zhang |
| 8,880,352 B2 | 11/2014 | Kale et al. |
| 8,912,436 B2 | 12/2014 | Gabriel |

(56) References Cited

U.S. PATENT DOCUMENTS

| | | |
|---|---|---|
| 8,998,890 B2 | 4/2015 | Paul et al. |
| 9,050,014 B2 | 6/2015 | Zhang |
| 9,055,959 B2 | 6/2015 | Vaska et al. |
| 9,060,890 B2 | 6/2015 | Bingener-Casey et al. |
| 9,084,584 B2 | 7/2015 | Weiland et al. |
| 9,107,600 B2 | 8/2015 | Narayan et al. |
| 9,113,896 B2 | 8/2015 | Mulier et al. |
| 9,173,586 B2 | 11/2015 | Deno et al. |
| 9,186,081 B2 | 11/2015 | Afonso et al. |
| 9,192,315 B2 | 11/2015 | Zhang |
| 9,204,927 B2 | 12/2015 | Afonso et al. |
| 9,220,435 B2 | 12/2015 | Deno |
| 9,237,920 B2 | 1/2016 | Leo et al. |
| 9,254,163 B2 | 2/2016 | Paul et al. |
| 9,265,557 B2 | 2/2016 | Sherman et al. |
| 9,271,782 B2 | 3/2016 | Paul et al. |
| 9,277,956 B2 | 3/2016 | Zhang |
| 9,283,025 B2 | 3/2016 | Paul et al. |
| 9,283,026 B2 | 3/2016 | Paul et al. |
| 9,314,180 B2 | 4/2016 | Indla et al. |
| 9,320,443 B2 | 4/2016 | Libbus et al. |
| 9,332,160 B1 | 5/2016 | Chenillo et al. |
| 9,380,953 B2 | 7/2016 | Houben et al. |
| 9,463,072 B2 | 10/2016 | Comaniciu et al. |
| 9,504,518 B2 | 11/2016 | Condie et al. |
| 9,561,070 B2 | 2/2017 | Brotz et al. |
| 9,603,554 B2 | 3/2017 | Liang et al. |
| 9,610,119 B2 | 4/2017 | Fish et al. |
| 9,610,396 B2 | 4/2017 | Curley et al. |
| 9,636,069 B2 | 5/2017 | Chakravarthy et al. |
| 9,662,033 B2 | 5/2017 | Severino |
| 9,668,802 B2 | 6/2017 | Brannan |
| 9,713,490 B2 | 7/2017 | Brotz et al. |
| 9,770,282 B2 | 9/2017 | Hoey et al. |
| 9,782,094 B2 | 10/2017 | Du et al. |
| 9,801,585 B2 | 10/2017 | Shah et al. |
| 9,808,171 B2 | 11/2017 | Balachandran et al. |
| 9,820,813 B2 | 11/2017 | Brannan |
| 9,889,006 B2 | 2/2018 | Sandhu et al. |
| 10,031,536 B2 | 7/2018 | Gabriel |
| 10,314,507 B2 * | 6/2019 | Govari .................. A61B 5/30 |
| 10,356,001 B1 | 7/2019 | Drakulic et al. |
| 10,485,485 B1 | 11/2019 | Drakulic et al. |
| 2001/0033614 A1 | 10/2001 | Hudson |
| 2002/0140857 A1 | 10/2002 | Limaye |
| 2002/0191107 A1 | 12/2002 | Hull et al. |
| 2004/0059237 A1 | 3/2004 | Narayan et al. |
| 2004/0092801 A1 | 5/2004 | Drakulic |
| 2004/0158167 A1 | 8/2004 | Smith et al. |
| 2005/0070968 A1 | 3/2005 | Bergelson et al. |
| 2005/0277826 A1 | 12/2005 | Dunseath |
| 2006/0276702 A1 | 12/2006 | McGinnis |
| 2007/0009108 A1 | 1/2007 | Furge |
| 2007/0171960 A1 | 7/2007 | Zhang |
| 2008/0080561 A1 | 4/2008 | Lide |
| 2008/0188965 A1 | 8/2008 | Bruey |
| 2008/0312523 A1 | 12/2008 | Dunseath |
| 2009/0018458 A1 | 1/2009 | Cao |
| 2009/0051759 A1 | 2/2009 | Adkins |
| 2009/0163801 A1 | 6/2009 | Sliwa |
| 2009/0259138 A1 | 10/2009 | Lin et al. |
| 2009/0275850 A1 | 11/2009 | Mehendale et al. |
| 2009/0307383 A1 | 12/2009 | Joiner |
| 2010/0183163 A1 | 7/2010 | Matsui |
| 2011/0028848 A1 | 2/2011 | Shaquer et al. |
| 2011/0263978 A1 | 10/2011 | Chen et al. |
| 2011/0286533 A1 | 11/2011 | Fortney |
| 2011/0319777 A1 | 12/2011 | Mehrotra et al. |
| 2012/0047435 A1 | 2/2012 | Holladay |
| 2012/0165735 A1 | 6/2012 | Keh et al. |
| 2012/0265084 A1 | 10/2012 | Stewart et al. |
| 2013/0158423 A1 | 6/2013 | Kapoor |
| 2013/0338529 A1 | 12/2013 | Ishijima et al. |
| 2014/0364848 A1 | 12/2014 | Heimbecher et al. |
| 2015/0012222 A1 | 1/2015 | Warner et al. |
| 2015/0032797 A1 | 1/2015 | Pan |
| 2015/0141807 A1 | 5/2015 | Fetterly |
| 2015/0313620 A1 | 11/2015 | Suri |
| 2015/0327815 A1 | 11/2015 | Hwang |
| 2015/0360032 A1 | 12/2015 | Bennet et al. |
| 2016/0001036 A1 | 1/2016 | Nickerson et al. |
| 2016/0015410 A1 | 1/2016 | Asirvatham et al. |
| 2016/0038047 A1 | 2/2016 | Urman et al. |
| 2016/0051322 A1 | 2/2016 | Asirvatham et al. |
| 2016/0058520 A1 | 3/2016 | Yang et al. |
| 2016/0143543 A1 | 5/2016 | Zhang |
| 2016/0158006 A1 | 6/2016 | Sandhu et al. |
| 2016/0183832 A1 | 6/2016 | Indla et al. |
| 2016/0184004 A1 | 6/2016 | Hull et al. |
| 2016/0188827 A1 | 6/2016 | Warner et al. |
| 2016/0193045 A1 | 7/2016 | Pollak |
| 2016/0203589 A1 | 7/2016 | Dzyubak et al. |
| 2016/0235485 A1 | 8/2016 | Belohlavek et al. |
| 2016/0256063 A1 | 9/2016 | Friedman et al. |
| 2016/0278756 A1 | 9/2016 | Aho et al. |
| 2016/0310039 A1 | 10/2016 | Everling et al. |
| 2016/0324485 A1 | 11/2016 | Erdemir et al. |
| 2016/0325108 A1 | 11/2016 | Volpe |
| 2016/0374754 A1 | 12/2016 | Asirvatham et al. |
| 2017/0000471 A1 | 1/2017 | Callstrom et al. |
| 2017/0042449 A1 | 2/2017 | Deno et al. |
| 2017/0056091 A1 | 3/2017 | Wallace |
| 2017/0056648 A1 | 3/2017 | Syed et al. |
| 2017/0124256 A1 | 5/2017 | Nantz et al. |
| 2017/0149510 A1 | 5/2017 | Bolshtyansky |
| 2017/0156616 A1 | 6/2017 | Talkachova et al. |
| 2017/0209060 A1 | 7/2017 | Srivathsan |
| 2017/0209691 A1 | 7/2017 | Sorajja |
| 2017/0231517 A1 | 8/2017 | Severino |
| 2017/0251939 A1 | 9/2017 | Santala et al. |
| 2017/0252152 A1 | 9/2017 | Sandhu et al. |
| 2017/0258521 A1 | 9/2017 | Asirvatham et al. |
| 2017/0258611 A1 | 9/2017 | Tefft et al. |
| 2017/0281193 A1 | 10/2017 | Asirvatham et al. |
| 2017/0296082 A1 | 10/2017 | Deno |
| 2017/0304624 A1 | 10/2017 | Friedman et al. |
| 2017/0309048 A1 | 10/2017 | Stepanek et al. |
| 2018/0067063 A1 | 3/2018 | Cherkassky et al. |
| 2018/0092563 A1 | 4/2018 | Matthiesen et al. |
| 2018/0168475 A1 | 6/2018 | Pekander |
| 2018/0183227 A1 | 6/2018 | Gabriel |
| 2018/0184932 A1 | 7/2018 | Saunamaki et al. |
| 2018/0249960 A1 | 9/2018 | Gupta et al. |
| 2018/0325375 A1 | 11/2018 | Cho et al. |
| 2019/0343414 A1 | 11/2019 | Drakulic et al. |
| 2019/0343463 A1 | 11/2019 | Drakulic et al. |
| 2019/0348975 A1 | 11/2019 | Drakulic et al. |
| 2019/0349310 A1 | 11/2019 | Drakulic et al. |
| 2019/0365250 A1 | 12/2019 | Drakulic et al. |
| 2020/0015687 A1 | 1/2020 | Drakulic et al. |
| 2020/0022591 A1 | 1/2020 | Drakulic et al. |

FOREIGN PATENT DOCUMENTS

| | | |
|---|---|---|
| EP | 2622612 B1 | 3/2018 |
| EP | 3565116 A1 | 11/2019 |
| WO | WO 2014/172398 A1 | 10/2014 |
| WO | WO 2014/189887 A3 | 11/2014 |
| WO | WO 2015/002935 A2 | 1/2015 |
| WO | WO 2015/002940 A2 | 1/2015 |
| WO | WO 2015/002945 A2 | 1/2015 |
| WO | WO 2015/013238 A3 | 1/2015 |
| WO | WO 2015/034897 A1 | 3/2015 |
| WO | WO 2015/048514 A1 | 4/2015 |
| WO | WO 2015/143327 A1 | 9/2015 |
| WO | WO 2017/074920 A1 | 5/2017 |
| WO | WO 2017/091736 A1 | 6/2017 |
| WO | WO 2017/096133 A1 | 6/2017 |

(56) References Cited

FOREIGN PATENT DOCUMENTS

| WO | WO 2017/106490 A1 | 6/2017 |
| WO | WO 2017/156229 A1 | 9/2017 |

OTHER PUBLICATIONS

Couck, et al., Effects of Short and Prolonged Transcutaneous Vagus Nerve Stimulation on Heart Rate Variability in Healthy Subjects, Autonomic Neuroscience, vol. 203, Mar. 2017, pp. 88-96.

Huck, et al., Preprocessing of Unipolar Signals Acquired by a Novel Intracardiac Mapping System, Current Directions in Biomedical Engineering 2016, vol. 2, No. 1, pp. 259-262.

Martinez-Iniesta, et al., Waveform Integrity in Atrial Fibrillation: The Forgotten Issue of Cardiac Electrophysiology, Annals of Biomedical Engineering, vol. 45, No. 8, Aug. 2017, pp. 1890-1907.

Mitrea, et al., Imaging Electrical Excitation Inside the Myocardial Wall, Biomedical Optics Express, vol. 2, No. 3, Mar. 1, 2011, pp. 620-633.

Shivkumar, K. and Ardell, J.L., Vagal Neuromodulation for Atrial Arrhythmias, JACC: Clinical Electrophysiology, vol. 3, No. 9, Sep. 2017, pp. 939-941.

Silberbauer, J., Wilson's Central Terminal, the Keystone to Electrogram Recording . . . What, Where and Why?, Apr. 23, 2013, 7 pages.

Venkatachalam, et al., Signals and Signal Processing for the Electrophysiologist: Part I: Electrogram Acquisition, Circulation: Arrhythmia and Electrophysiology 2011, vol. 4, pp. 965-973.

Venkatachalam, et al., Signals and Signal Processing for the Electrophysiologist: Part II: Signal Processing and Artifact, Circulation: Arrhythmia and Electrophysiology 2011, vol. 4, pp. 974-981.

Google: "digital signal processing." (Year: 2019).

Notification of the Transmittal of the International Search Report and the Written Opinion of the International Searching Authority directed to application No. PCT/US2019/031434, dated Jul. 16, 2019, 10 pages.

Notification of the Transmittal of the International Search Report and the Written Opinion of the International Searching Authority directed to application No. PCT/US2019/031433, dated Jun. 21, 2019, 11 pages.

International Preliminary Report on Patentability directed to related International Patent Application No. PCT/US2019/031433, dated Nov. 10, 2020; 6 pages.

International Preliminary Report on Patentability directed to related International Patent Application No. PCT/US2019/031434, dated Nov. 10, 2020, with attached English-language translation; 6 pages.

* cited by examiner

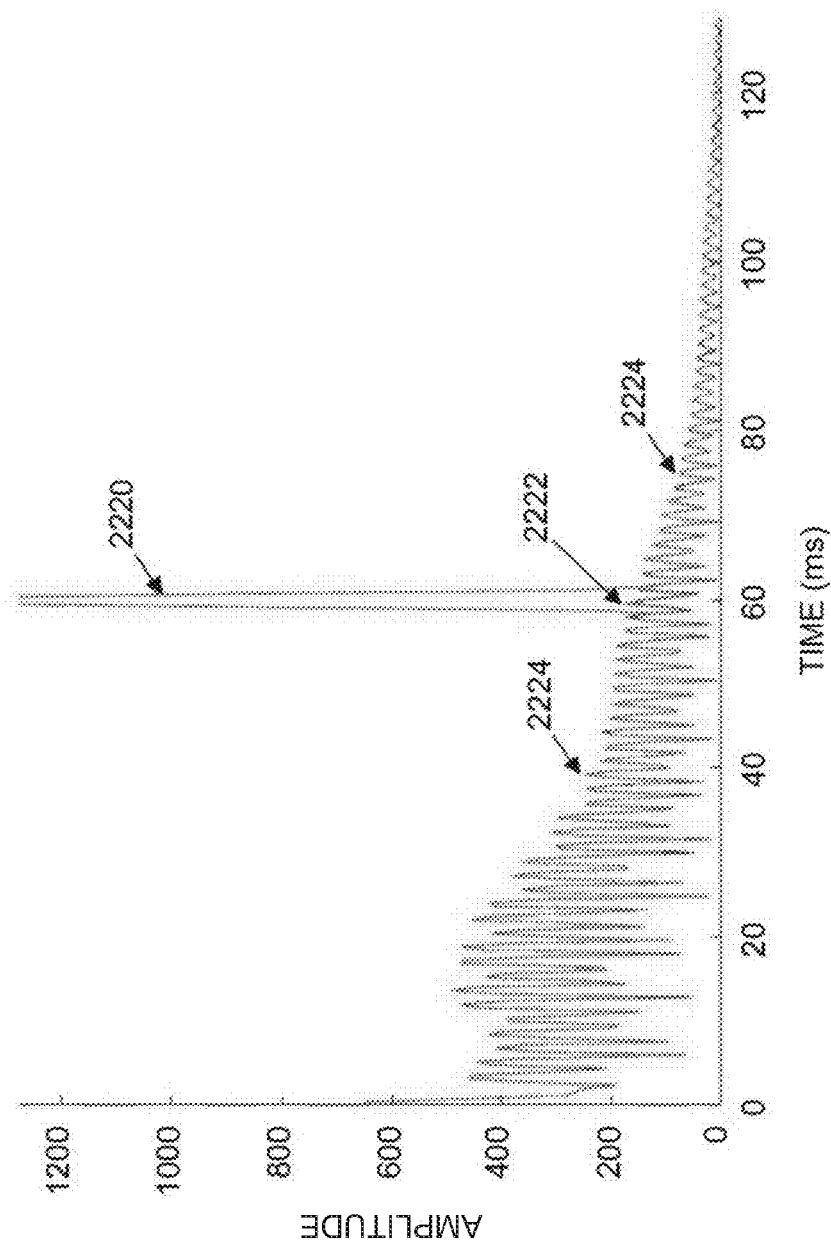

APPARATUS FOR PROCESSING BIOMEDICAL SIGNALS FOR DISPLAY

CROSS-REFERENCE TO RELATED APPLICATIONS

This application is a divisional of U.S. patent application Ser. No. 16/866,195, filed May 4, 2020 (now U.S. Pat. No. 10,911,365), which is a continuation of U.S. patent application Ser. No. 16/718,996, filed Dec. 18, 2019 (now U.S. Pat. No. 10,841,232), which is a divisional of U.S. patent application Ser. No. 16/195,562, filed Nov. 19, 2018 (now U.S. Pat. No. 10,686,715), which claims the benefit of U.S. Provisional Patent Application No. 62/669,345, filed May 9, 2018, entitled "Acquisition and Preservation of Electrical Signal Information in a Multi-Signal-Source Environment," all of which are hereby incorporated by reference.

TECHNICAL FIELD

Embodiments included herein generally relate to cardiac electrophysiology (EP) signal acquisition and recording systems. More particularly, apparatus and method embodiments are disclosed for removing a large-signal voltage offset from a biomedical signal.

BACKGROUND

Catheter ablation is a procedure to treat arrhythmias such as atrial fibrillation, a disease of the heart muscle characterized by abnormal conduction. Depending on the severity of the problem, multiple ablation procedures may be necessary to achieve effective results. This is because current electrophysiology (EP) technology has limitations in precisely locating the tissue to ablate that is the source of the abnormality.

The conventional diagnostic process starts with an electrocardiogram (ECG) taken from electrodes attached to the surface of the skin of a subject (e.g., a patient). A medical team evaluates the ECG signal and determines whether medication and/or ablation are/is indicated. If ablation is indicated, an EP study is performed. A catheter is inserted into the heart via the patient's neck or groin and the electrical activity of the heart is recorded. Based on this EP study, ablation is performed on the area(s) of the heart that the medical team suspects is causing the abnormal heart rhythm(s).

An ablation catheter is inserted into the patient's blood vessel and guided to the site of the tissue that is causing the abnormal electrical propagation in the heart. The catheter may use different energy sources (the most common being heat or cold) to scar the tissue, reducing its ability to initiate and/or transmit abnormal electrical impulses, which eliminates the abnormal heart rhythm. ECG signals are recorded from a surface electrode on a patient's skin, and intracardiac (IC) signals may be obtained from catheters inside the patient's heart and recorded as an electrogram (EGM). Both ECG and IC (EGM) signals are small signals that require conditioning and amplification to be accurately evaluated.

In conventional EP systems, to confirm whether the ablation treatment of a certain tissue site is successful, the medical team must often stop the ablation process and collect physiologic signals (e.g., cardiac) from a monitoring device (e.g., ECG monitor). This is because current systems do not allow accurate simultaneous detection, acquisition, and isolation of small cardiac signals (on the order of 0.1-5 mV over a range of frequencies) in near real-time during the application of large ablation signals (on the order of a few hundred volts at frequencies around 450 kHz).

Specifically, U.S. Patent Application Publication No. US 2006/0142753A1 to Francischelli, et al. propose a system and method for ablation and assessing their completeness or transmurality by monitoring the depolarization ECG signals from electrodes adjacent to the tissue to be ablated. Francischelli, et al. point out that, to minimize noise-sensing problems during measurements of the ECG signals from the electrodes on the ablation device, the measurements are preferably made during interruptions in the delivery of ablation energy to the ablation electrodes.

Generally, some current EP recording systems can effectively support treatment of arrhythmias such as atrial flutter and supra ventricular tachycardia, which show up as large-amplitude, low-frequency signals. However, more complex and prevalent arrhythmias, such as atrial fibrillation and ventricular tachycardia, which are characterized by low-amplitude, high-frequency signals, have not found effective evaluation of all relevant signals.

This signal detection, acquisition, and isolation can be further complicated by equipment line noise and pacing signals. To remove noise and artifacts from the various electrical signal information, current EP recorders use low-pass, high-pass, and notch filters. Unfortunately, conventional filtering techniques can alter signals and make it difficult or impossible to see low-amplitude, high-frequency signals that can be inherent in cardiac monitoring, the visualization of which signals could help treat atrial fibrillation and ventricular tachycardia. It has been recently recognized that the assurance of waveform integrity, such as for noise-free acquisition of IC and ECG signals in an EP environment, had not been previously accomplished due to contamination of various signals by artifacts and noise.

Specifically, in an article titled *Waveform Integrity in Atrial Fibrillation: The Forgotten Issue of Cardiac Electrophysiology* (Annals of Biomedical Engineering, Apr. 18, 2017), Martinez-Iniesta, et al. point out that high-frequency and broadband equipment noise is "unavoidably recorded" during signal acquisition, and that further complications of acquisition result from a variety of other signals, including 50 or 60 Hz electrical mains, high-frequency patient muscle activity, and low-frequency baseline wander from respiratory or catheter movements or unstable catheter contact. Martinez-Iniesta, et al. further point out that regular filtering causes significant alteration of waveforms and spectral properties, as well as poor noise reduction. Yet aggressive filtering between 30 and 300 Hz is still a routine EP practice.

Conventional practices distort morphological features in resulting signals, causing loss of relevant (of interest) signal information and affecting signal validity. Martinez-Iniesta, et al. propose a partial software solution for only mid- and high-frequency noise reduction using preprocessing and de-noising methods, yet no solution exists combining low-frequency noise-reduction components in software with noise-reduction components in hardware. A desired feature of EP systems is the ability to preserve the integrity of original signal information using a combination of hardware and software that can remove noise from signals (or promote a high signal-to-noise ratio) while minimizing hardware filtering that would otherwise remove signal content of interest.

Currently, the predominant approach for ablation treatment of paroxysmal and persistent atrial fibrillation is pulmonary vein isolation (PVI), wherein a medical team, using a cardiac mapping system, recreates the heart geometry in 3D and performs ablation on anatomical locations such as the pulmonary vein from which the atrial fibrillation emanates. The procedure is a long 2-8 hours, and a physician may not achieve a durable lesion/scar to isolate the tissue causing the problem from the left atrium. Thus, patients are often required to return for additional ablation procedures to complete the treatment. However, additional ablation procedures, and possible complications, can be avoided by being able to clearly visualize the cardiac signals during ablation and determine whether an ablation lesion is transmural.

Conventional EP systems may suffer from several other limitations. First, a user often wants to process and display multiple versions of signals in near real-time. For example, a medical team may want to simultaneously display various and multiple versions of ECG, IC, and other physiologic signals in near real-time to evaluate different signal attributes. But conventional EP systems are often unable to simultaneously process and display multiple versions of signals in near real-time.

Second, a user often wants to dynamically apply a new digital signal processing function to a signal without interfering with other digital signal processing functions already being applied to the signal. But conventional solutions do not enable a user to dynamically apply a new digital signal processing function to a signal without stopping the capture of the signal, or interfering with other digital signal processing functions already being applied to the signal.

Finally, a user often wants to synchronize the processing and display of multiple signals in near real-time. For example, a user may want to synchronize the display of multiple processed versions of the same signal. Further, a medical team may want to synchronize the display of multiple processed versions of ECG, IC, and other physiologic signals. This is because the ability of the medical team to make an effective clinical diagnosis may depend on comparing multiple signals at the same point in time. But conventional solutions may not be able to process and synchronize the display of multiple processed signals in near real-time.

SUMMARY OF THE EMBODIMENTS

Apparatus, systems, and methods are disclosed for EP signal acquisition and recording with multiple improvements in noise cancellation, sampling rate, and dynamic range in various biomedical applications.

The embodiments of the disclosed EP system can record raw (unaltered) cardiac and other physiologic signals with multiple display options and with low noise and large input signal dynamic range. This is achieved using a low-noise amplifier topology, with minimal filtering to band-limit the signal, and a high-resolution A/D converter. In addition, the disclosed EP system can provide large-signal (e.g., from a defibrillator) input protection and radio frequency (RF) signal (e.g., from ablation) noise suppression. In this architecture, there is no need for gain switching, and the full range of input signals is digitized with high resolution.

Raw signals acquired by an acquisition module are filtered and processed in accompanying software using a digital processing module, with minimal use of filters in the hardware (e.g., hardware filters are only used for AC coupling, anti-aliasing, and RF suppression). The use of software-based digital signal processing algorithms allows the display of signals in real-time as a raw signal, or as a combination of raw and processed signals simultaneously in real-time in a single window or in multiple windows. Furthermore, the visualization and review capabilities of the disclosed EP system allow a user to mark features specified in algorithms on real-time tracings.

The disclosed EP system allows for the display of signals with more than one signal processing algorithm applied at the same time, a feature not found in conventional systems. This allows a user to look at signals filtered in multiple ways for specific reasons. In the real-time window, waveforms of interest can be displayed as raw signals or as any combination of raw and filtered signals to enable better visualization of signals in the presence of noise and artifacts.

All displayed signals are time synchronized. On a review screen, the user has the option of opening multiple review windows, with the ability to display the results of various signal-processing algorithms, independent of the real-time tracings. The disclosed EP system also uses novel optimal biphasic waveforms and signal processing algorithms for signal enhancement during pacing, and novel algorithms for enhanced user visualization.

From a clinical perspective, the disclosed EP system can significantly assist in a medical team's decision making for patients undergoing various medical therapies (such as ablation), with benefits including, but not limited to: suppression of RF energy for cleaner, more reliable recordings of intracardiac signals, less wander, and noise reduction; improved dynamic range for better visualization, especially of very low amplitude signals temporally situated within large-amplitude signals; real-time digital processing and recording of raw signals to facilitate signal filtering without affecting original information and to reduce artifacts and noise; high-quality unipolar signals to assist in the determination of tissue type and catheter location; improved waveform integrity and reduced artifacts that are byproducts of signal processing, allowing a medical team to enhance procedure outcomes; and improved signal information, allowing a medical team to provide more accurate catheter tip position for ablation and other therapeutic levels and durations for therapy effectiveness.

Some embodiments herein describe a circuit for removing a large-signal voltage offset from a biomedical signal. The circuit includes a first operational amplifier having a differential input and a differential output, and is configured to receive the biomedical signal with the large-signal voltage offset at the differential input. The circuit also includes a second operational amplifier having a common mode voltage input and configured to output a common mode reference voltage at a common mode node. A first pair of diode stages is coupled between the differential output and respective ones of a first differential node and a second differential node and is configured to monitor an amplitude of the large-signal voltage offset. A plurality of timing banks is coupled between the respective ones of the first differential node and the second differential node and the common mode node. The first pair of diode stages and the plurality of timing banks may be configured to attenuate the large-signal voltage offset persisting for a duration of at least the time constant, wherein the large-signal voltage offset is above an activation threshold. Further, a second pair of diode stages is coupled between the respective ones of the first differential node and the second differential node and the common mode node, wherein the large-signal voltage offset is attenuated at an output of each of the second pair of diode stages. The second pair of diode stages is configured to limit a saturation duration of the large-signal voltage offset to shorter than a saturation recovery time.

Various method embodiments are described for removing a voltage offset from an electrical signal (e.g., a biomedical signal in some embodiments), including receiving, at a differential input of a first operational amplifier, the electrical signal, and amplifying, by the first operational amplifier, the electrical signal by a first gain. Method embodiments include monitoring, by a first pair of diode stages coupled to a differential output of the first operational amplifier, an amplitude of the electrical signal for the voltage offset. Further, the method embodiments include attenuating, by the first pair of diode stages and a plurality of timing banks, the amplitude of the electrical signal. The attenuating includes limiting charging, by the first pair of diode stages, of the plurality of timing banks from the electrical signal and producing, by the plurality of timing banks, a differential signal. The attenuating further includes charging of a resistor-capacitor network of the plurality of timing banks and setting, by the plurality of timing banks, a time constant based on the charging of the resistor-capacitor network. The method allows for attenuating the amplitude of the differential signal to remove the voltage offset persisting at an activation threshold for a duration of at least the time constant.

Some method embodiments include limiting, by a second pair of diode stages, the differential signal from the plurality of timing banks and further limiting a saturation duration of the differential signal to less than a saturation recovery time. Some method embodiments further include pulling an output voltage of the second pair of diode stages toward a common mode reference voltage at a common mode node coupled to the plurality of timing banks. Some method embodiments may include pulling, by the second pair of diode stages, a positive input node voltage of the first operational amplifier down toward the common mode reference voltage and a negative input node voltage of the first operational amplifier up toward the common mode reference voltage. Some method embodiments further include limiting, by the second pair of diode stages, the differential signal from the plurality of timing banks, wherein the positive input node voltage and the negative input node voltage are gradually pulled into monitoring range after about the saturation recovery time.

BRIEF DESCRIPTION OF THE DRAWINGS

The accompanying drawings, which are incorporated herein and form part of the specification, illustrate the present embodiments and, together with the description, further serve to explain the principles of the present embodiments and to enable a person skilled in the relevant art(s) to make and use the present embodiments.

FIG. 22C illustrates the EP system's ability to remove 60 Hz noise, without saturation or delayed recovery, while preserving the component of the 60 Hz signal that belongs to the original waveform, according to an exemplary embodiment.

Figure 1:
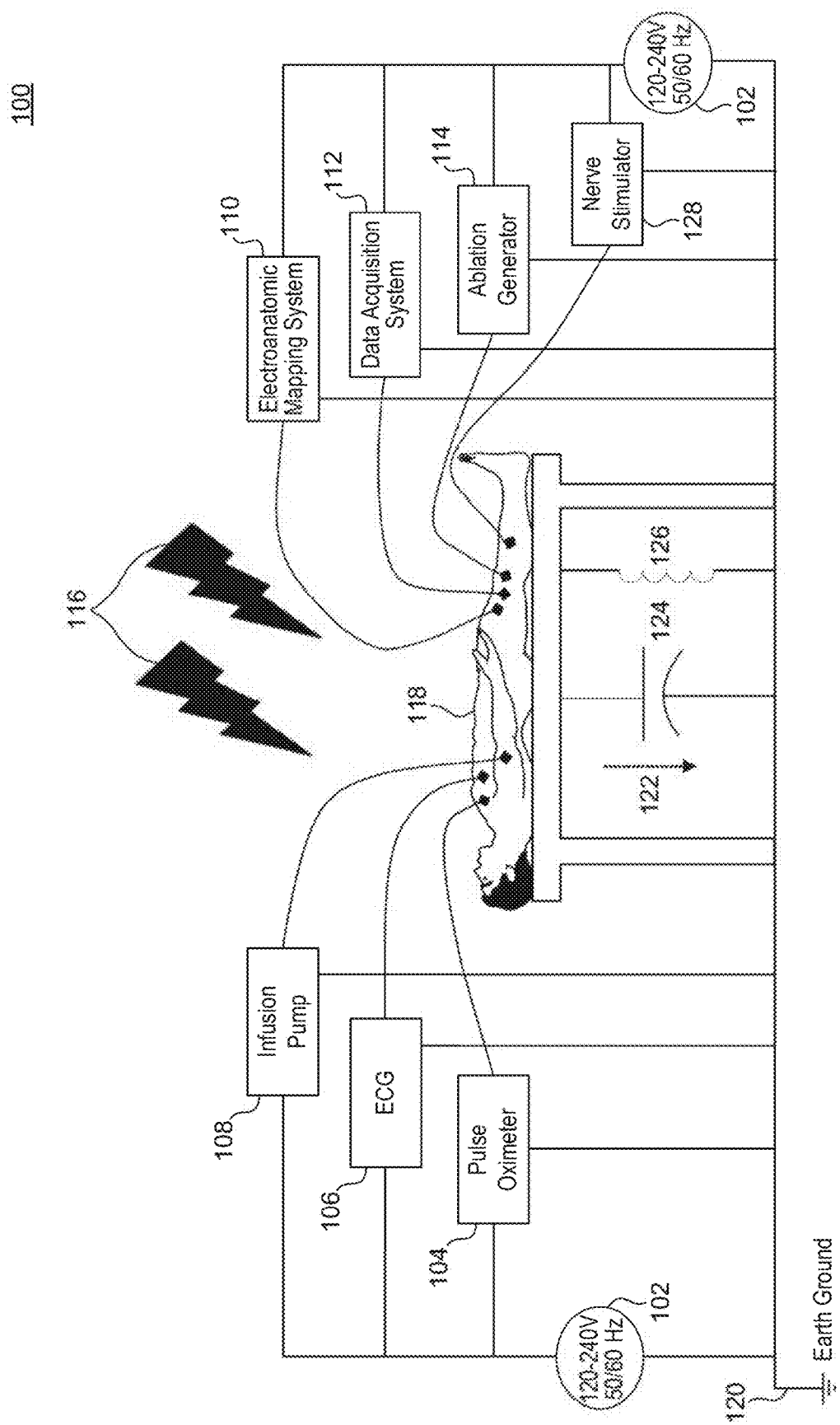
FIG. 1 illustrates a block diagram of a conventional electrophysiology (EP) environment with patient connections and sources of interference.

The features and advantages of the present embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

Apparatus, systems, and methods related to a unique amplifier topology are disclosed for conditioning cardiac (e.g., ECG and IC) and other physiologic signals, specifically to clearly define and record low-amplitude, low-frequency information, which may be acquired during ablation and other similar large-signal perturbations, such as pacing and stimulation. During procedures, the tip of a catheter (or other electrodes) can be connected to pacing, ablation, and stimulator systems to allow visualization, pacing, ablation, and stimulation without mode switching. For example, the disclosed apparatus, systems, and methods can effectively separate ablation signals from cardiac signals during ablation while simultaneously providing input protection against high voltage, such as from defibrillation signals. Similarly, the disclosed apparatus, systems, and methods can effectively separate stimulation signals from physiologic signals during stimulation.

As different system recording requirements cannot be satisfied simultaneously for each signal type, each block, or module, of the system can be performance optimized to achieve multiple signal conditioning requirements desired by clinicians. The various embodiments can enable the system to handle cardiac, pacing, ablation, defibrillation, stimulator, and other physiologic signal types simultaneously by detecting, conditioning, and displaying the signal of interest, to monitor, for example, the effect of an ongoing procedure on a cardiac signal.

Additionally, the various embodiments can ensure the acquisition of multiple low-amplitude cardiac signals in the presence of numerous sources of electrical noise and environmental interference aside from the large signals injected during ablation and stimulation procedures, pacing, or defibrillation. The cardiac signals of interest can also be displayed in an uncomplicated and clinically-relevant way, processing the signals in real-time, or near-real-time, to display a comprehensive cause-and-effect relationship between physician-initiated procedures and resulting cardiac signals, while contemporaneously identifying signal artifacts and removing unwanted noise. This disclosure identifies both hardware and software embodiments to achieve these objectives.

This disclosure refers to both "unipolar" and "bipolar signals," which are both widely used in EP recordings, but for complementary purposes. Both unipolar and bipolar signals are taken from the potential difference recorded at two (or more) different, separated electrodes on a patient's body, specifically the limbs and chest of the patient, for example, to measure ECG signals, or at two (or more) different, separated catheters placed directly on cardiac tissue, for another example, to measure IC signals.

It is conventional to use a 12-lead ECG system consisting of a connection to each of the limbs: right arm (RA), left arm (LA), right leg (RL), and left leg (LL), and six precordial connections V1 through V6 from six separate electrodes placed at various locations on the patient's chest. The individual ECG electrode wires are connected to a terminal block at the end of a patient table, routing from there to a data acquisition system. All leads are conventionally connected to protection circuitry to prevent damage to the instrumentation caused by defibrillation potentials or static electricity from the environment.

Bipolar signals are standard for certain ECG measurements (lead I, II, III), but they may also be obtained directly from the heart surface to collect IC signals. Bipolar signals may be obtained by attaching two (or more) electrodes in close proximity in a specific area of the heart or cardiac tissue and measuring the potential difference between the electrodes, providing information about local electrical activity, such as late potentials caused by damaged heart muscle. Bipolar IC signals do not, however, provide information about electrical impulse propagation direction.

Unipolar signals arise from a point source, such as may be obtained from an IC potential, by placing one IC electrode on the surface of the patient's heart and the other electrode at a distance from the first to serve as a reference signal. Unipolar leads from IC electrodes are connected in such a way that one lead serves as the active lead while the other lead(s) is/are at an inactive location or the result of a calculated inactive location (WCT, discussed below). In this way, the current flowing towards the active electrode produces a positive deflection, while current flowing away from the active electrode produces a negative deflection. This provides information about cardiac signal propagation direction. Unipolar recordings are especially useful when directionality information is desired, such as in the determination of depolarization and repolarization pathways in the endocardium and epicardium.

Leads may also be connected to the limbs to create an imaginary triangle called "Einthoven's triangle." In this way, true bipolar leads can be obtained by referencing each connection to one of the other two (e.g., LA referenced to RA is Lead I; LL to RA is Lead II, and finally, LA to LL is Lead III). Then, an average of the three limb wires RA, LA, and LL can approximate a zero potential point to provide a reference electrode (WCT, discussed below). Here, the vector sum of Lead I and Lead III is Lead II.

Using the concept of Einthoven's triangle, the Wilson Central Terminal (WCT) is an electrical circuit concept used in the art (and discussed further in this disclosure) that can be used as an indifferent electrode that acts as an electrical center of the heart as a reference. The WCT can be used when IC signals are desired to be displayed in unipolar fashion. When using the WCT as a reference for unipolar signals, the unipolar signals can approximate widely-spaced bipolar signals for consistent unipolar recording. The WCT can prevent an additional catheter from having to be used as a reference for unipolar recordings of IC signals.

In this disclosure, "near real-time" refers to the acquisition and visualization of signals through the EP system from the time they occur at the input of the hardware circuitry of the EP system to the time they are first displayed on the EP system display monitor(s), either in raw (unprocessed) form or after being processed by the EP system Main Processing Unit (MPU) and one or more digital signal processing (DSP) module(s). "Near real-time" for a raw signal can be less than approximately five (5) milliseconds, and for a processed signal can be less than approximately fifty (50) milliseconds.

FIG. 1 is a block diagram representing a conventional EP environment 100 with patient connections and sources of interference. As understood by a person of ordinary skill in the art, the patient 118 may be connected to diagnostic equipment such as a pulse oximeter 104, one or more ECG units 106, an infusion pump 108, an electroanatomic mapping system 110, a data acquisition system 112, such as the EP system disclosed herein, an ablation generator 114, a nerve stimulator 128, and other diagnostic equipment, such as an external defibrillator, and several IC catheters. Such diagnostic equipment can be connected to and can be powered by 120-240V, 50/60 Hz AC power mains 102. The laboratory diagnostic equipment can be connected to earth ground 120, through its power source connection.

As the number of connections to the patient 118 increases, the leakage current 122 from all patient connections through the patient 118 to earth ground 120 increases, increasing the likelihood of interference and adverse effects. Total leakage current 122 when such equipment is connected and operating at the same time may safely and allowably be up to several tens of microamperes at a fundamental mains frequency of 50 or 60 Hz, with harmonics extending to several thousand Hertz. This leakage current 122 can interfere substantially with the processing of ECG and IC signals. Furthermore, the patient 118 can be both capacitively coupled 124 and inductively coupled 126 to the 120/240 AC power mains 102. The patient 118 may additionally pick up RF interference 116 from equipment in proximity to the EP environment, such as wireless headsets, mobile phones, and wireless monitors.

For reference, TABLE 1 outlines signals that may be found in a conventional medical instrumentation/EP environment, both wanted and unwanted, and their signal characteristics.

TABLE 1

Signal characteristics in a conventional EP environment

| Signal Type | Signal Amplitude/ Output | Frequency | Nature/Use of Signal |
|---|---|---|---|
| ECG (cardiac skin electrodes) | 0.5 to 4 mV | 0.01 to 250 Hz | Conventionally required for cardiac monitoring |
| IC (intracardiac leads) | 20 µV to 10 mV | 0.05 to 500 Hz | Conventionally required for cardiac monitoring |
| EGG (electro-gastrography) | 10 µV to 1000 µV | DC to 1 Hz | Smallest biomedical signal of interest (non-EEG) |
| RF Ablation System | RF output: 100 W, 100 s of V | 300-600 kHz, 460-500 kHz typical | Conventional equipment used during EP study |
| Defibrillation | 4500 to 5000 V | 10 s of ms duration | Possible equipment used in EP environment |
| Pacing Cardiac Stimulator | 0.1 to 25 mA, 27 Vmax | 0.5 to 10 ms duration; up to 1000 µs pulse width; up to 1200 Hz | Conventional equipment used during EP study |
| Equipment power-line noise | 2 Vpp typical | 60 Hz, 180 Hz harmonic | Conventional lab environment power |

As a result of equipment noise and other EP environment interference, measured voltages on a patient's body can be upwards of 1-3V RMS (root mean squared) over a frequency spectrum ranging from 50 Hz to several tens of megahertz. Yet, the amplitude of cardiac signals can measure in the range of 25 microvolts to 5 mV. To display these signals amongst the noisy environment, the cardiac signals are conventionally amplified and displayed with no loss of detail (so as not to miss relevant information, for example) and minimal added noise (so as not to cover up signal details, for example), while delivering RF ablation energy at about 70 V RMS at 500 kHz, or cardiac stimulation up to 25 mA, for example.

To properly acquire and identify cardiac signals of interest in such an environment, a very high signal-to-noise (SNR) ratio (on the order of 30 dB) is desirable but not achievable without an approach to minimize or eliminate sources of electrical interference before having to process them electrically through software methods. Conventional hardware approaches used to condition the signals in such a noisy environment include shielding of cables, grounding of equipment, balancing inputs and outputs, differential amplification, filtering, lowering circuit impedances, electric isolation, or signal enhancement techniques. These conventional methods have had limited success in achieving sufficient SNR.

The disclosed hardware embodiments can decrease interference while applying novel electrical circuit topology to minimize noise, isolate the IC and ECG signals of interest, condition those signals, and remove unwanted artifacts. This can be done before the signals are passed to processing software that provides an electrophysiologist the power of near real-time visualization and comprehensive signal review. Embodiments of the EP system described herein can achieve considerable SNR improvement.

Figure 2:
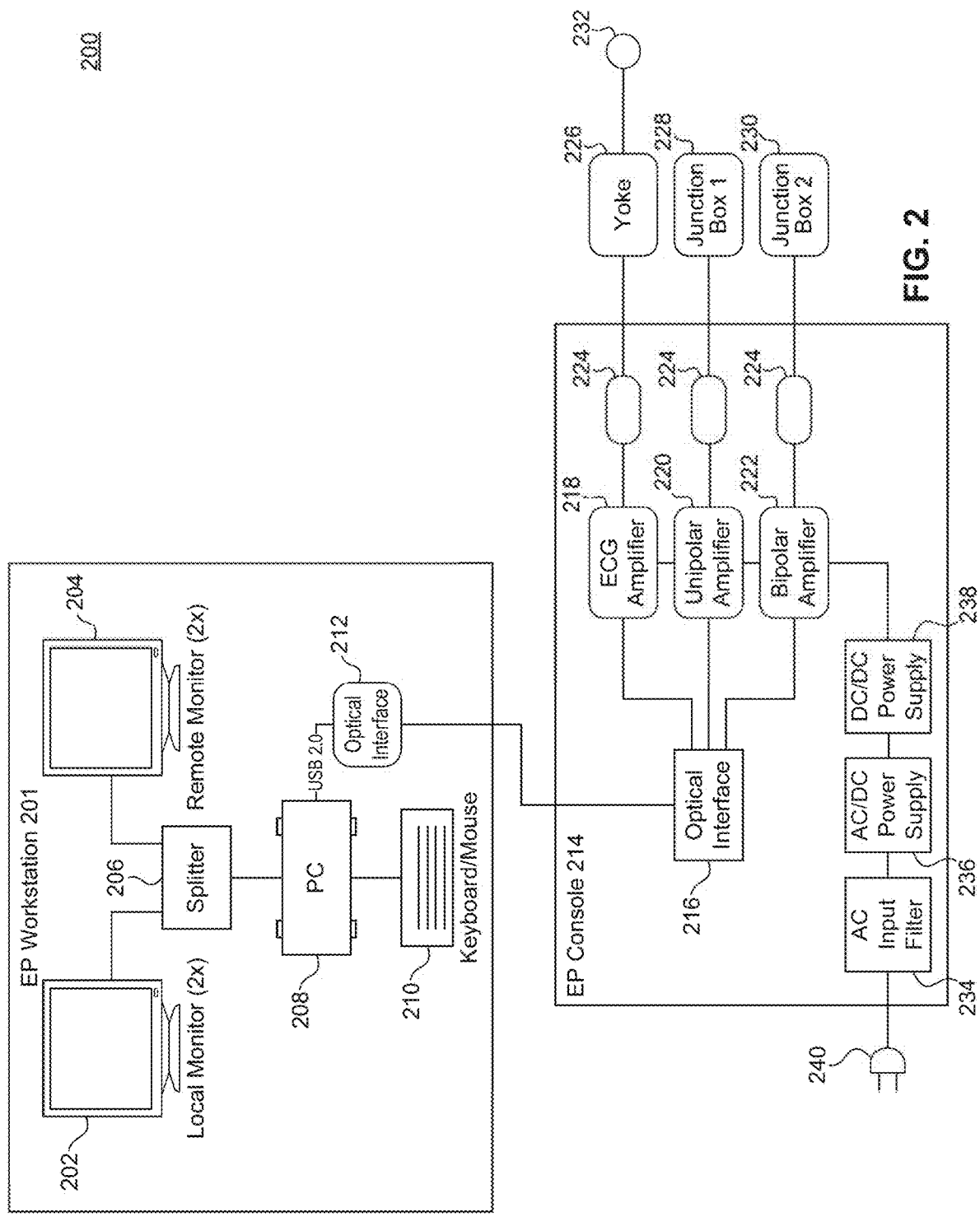
FIG. 2 illustrates a hardware system block diagram of the disclosed EP hardware system, according to some embodiments.

FIG. 2 is a hardware system block diagram representing the disclosed EP hardware system 200, including, for example, an EP workstation 201 and an EP console 214, according to some embodiments. The system can include an EP console 214 with an optical interface 216 of the EP measurement hardware from a user input, visualization, and review workstation (herein, "EP workstation" 201). The EP workstation 201 can include, for example, a conventional laboratory PC 208 with a keyboard/mouse 210 and a monitor splitter 206 facilitating multiple monitors 202, 204 to provide multiple-signal, multiple-context display capability for EP signal visualization and review software. The EP workstation 201 can also include an additional optical interface 212 for electrically isolated data transmission from the EP console 214 over USB 2.0, for example.

The EP console 214 can include one or more ECG amplifiers 218, one or more unipolar amplifiers 220 to process unipolar signals, and one or more bipolar amplifiers 222 to process bipolar signals from a plurality of ECG and EGM monitoring units 224. The EP console 214 can also include a dedicated AC input filter 234, a AC/DC power supply 236, and a DC/DC power supply 238 to condition and transform mains 120/240 V, 50/60 Hz source power 240 into DC power for use by the diagnostic equipment. ECG and EGM electrode inputs 232 can enter the EP console 214 through a yoke 226 that provides additional input impedance for protection. Junction boxes (1 and 2) 228, 230 can provide convenient plug-in interfaces for IC catheter inputs (not shown) for subsequent processing by EGM monitoring units 224.

Figure 3:
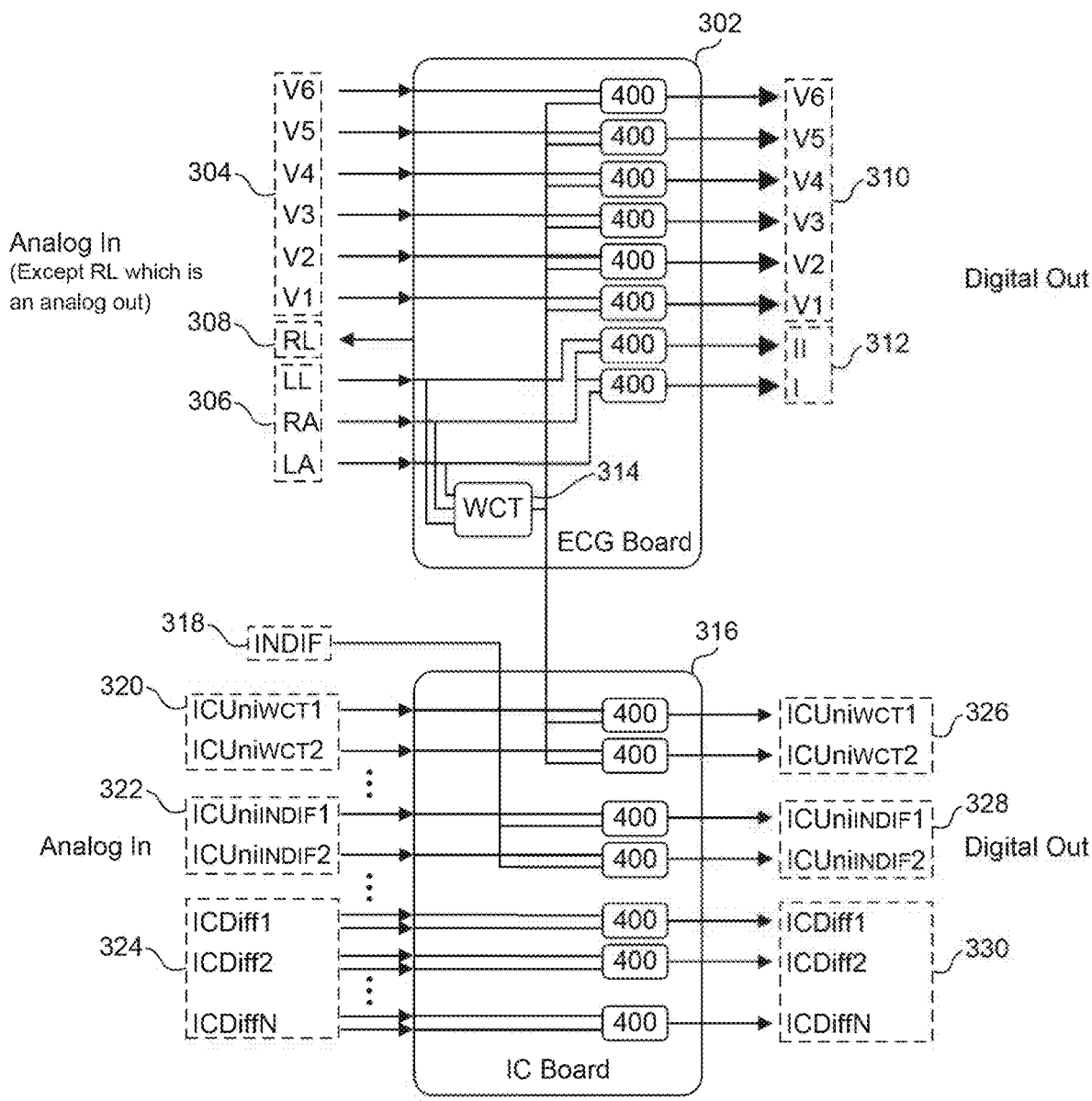
FIG. 3 illustrates a block diagram of a multi-channel analog-to-digital input/output of the EP hardware system input stage, according to some embodiments.

FIG. 3 is a block diagram representing a multi-channel analog-to-digital input/output module 300 of the EP hardware system input stage, including an ECG board 302 and an IC board 316, according to some embodiments. The ECG board 302 and the IC board 316 represent a portion of the ECG amplifier 218, unipolar amplifier 220, and bipolar amplifier 222 of FIG. 2. The ECG board 302 and the IC board 316 include a plurality of EP hardware system input stage 400 channels, discussed below (see FIG. 4). FIG. 3 illustrates one (1) 8-channel ECG board and one (1) multi-channel IC board, according to an exemplary embodiment. Some embodiments have at least sixteen (16) channels. Other embodiments can include more or fewer channels.

In FIG. 3, analog inputs V1-V6 304 represent six separate ECG (precordial) electrodes that can be placed at various locations on the patient's chest. Analog inputs LL, RA, and LA 306 represent the left leg, right arm, and left arm limb leads, respectively. Analog output RL 308 represents the patient return line to drive the right leg, as discussed later in this disclosure. WCT 314 on the ECG board 302, also discussed later in this disclosure, represents the Wilson Central Terminal, which also uses the analog inputs LL, RA, and LA 306. The output of the WCT 314 can then be input to each channel of the EP hardware system input stage 400 corresponding to the analog inputs V1-V6 304. Each of the digital outputs V1-V6 310 represents a conditioned and digitized version of the respective analog inputs V1-V6 304. In an exemplary embodiment, digital outputs I, II 312 can include LA referenced to RA as lead I, and LL referenced to RA as lead II, in a conditioned and digitized form. Then, an average of the three limb wires LL, RA, and LA 306 can approximate a zero potential point to provide a reference level for the generation of RL 308.

In FIG. 3, a plurality of analog inputs to the IC board 316 represent possible connections and channels through the EP hardware system input stage 400 (see FIG. 4) from the intracardiac catheters. The IC board 316 can accept IC signals that are either unipolar or bipolar. INDIF 318 represents the indifferent electrode, which provides a reference for a plurality of unipolar indifferent leads. ICUniWCT1, 2, through N signals 320, represent unipolar IC signals referenced to the WCT. ICUniINDIF1, 2, through N signals 322, represent the active electrode of each IC unipolar signal.

ICDiff1, 2, through N signals 324, represent a plurality of the bipolar differential signals from IC catheters. A plurality of digital outputs represents the conditioned and digitized versions of the analog inputs, specifically ICUniWCT1, 2, through N signals 326; ICUniINDIF1, 2, through N signals 328; and ICDiff1, 2, through N signals 330.

Figure 4:
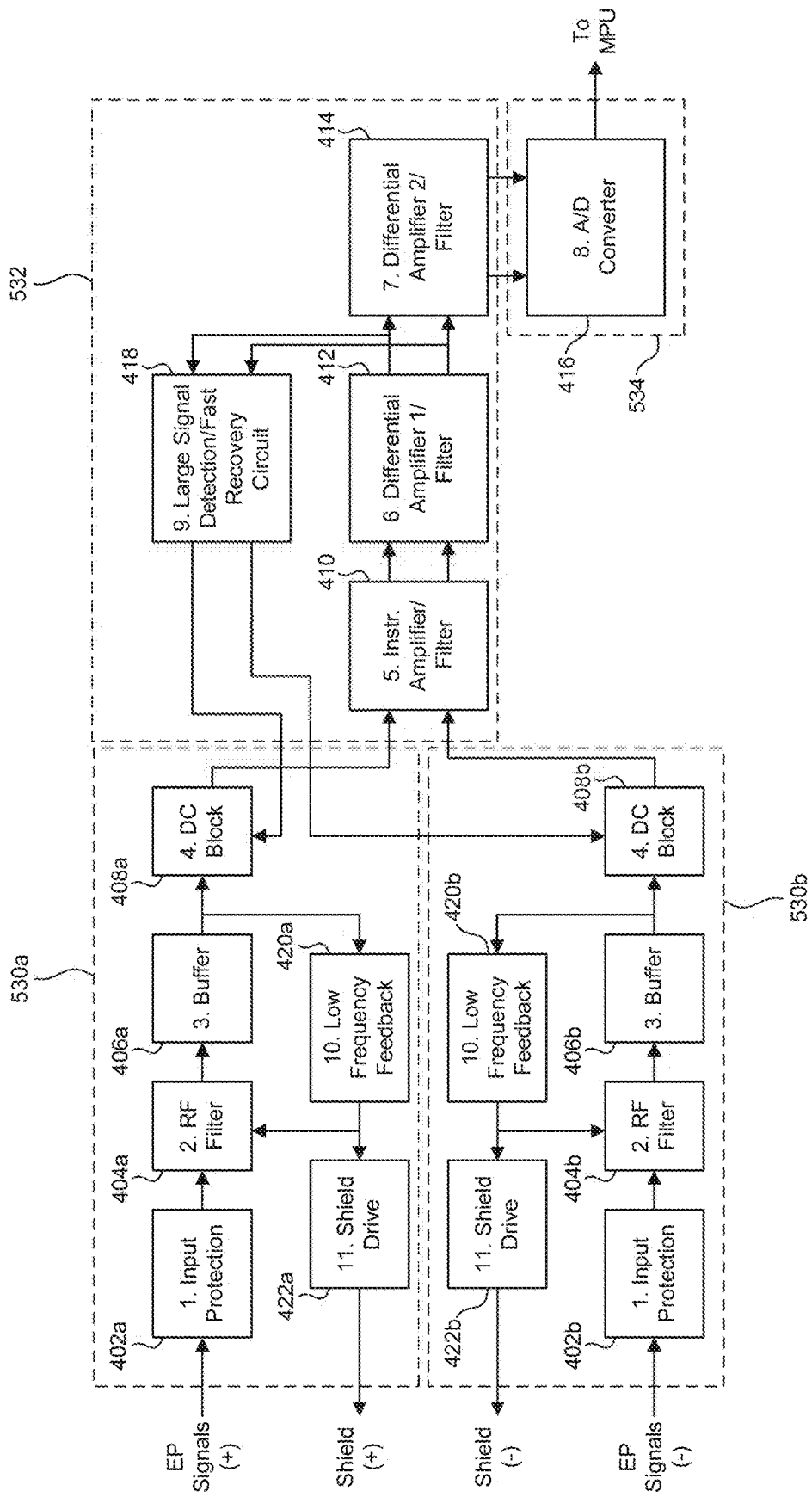
FIG. 4 illustrates a block diagram of a single channel of the EP hardware system input stage, according to some embodiments.

FIG. 4 is a block diagram representing a single channel of the EP hardware system input stage 400, having circuitry for input protection, signal filtering, detection, feedback, and amplification, according to some embodiments. The circuitry is illustrated in the block diagram by numbered blocks 1 through 11, each representing a part of the functionality of the hardware. This division and labeling of blocks is for ease of description and not meant to limit the scope of protection afforded by the appended claims. The input protection and signal filtering sections of the EP hardware system input stage 400 include symmetric positive and negative circuitry to generate differential versions of each input signal for a differential signal amplification stage 532, described below.

Figure 5A:
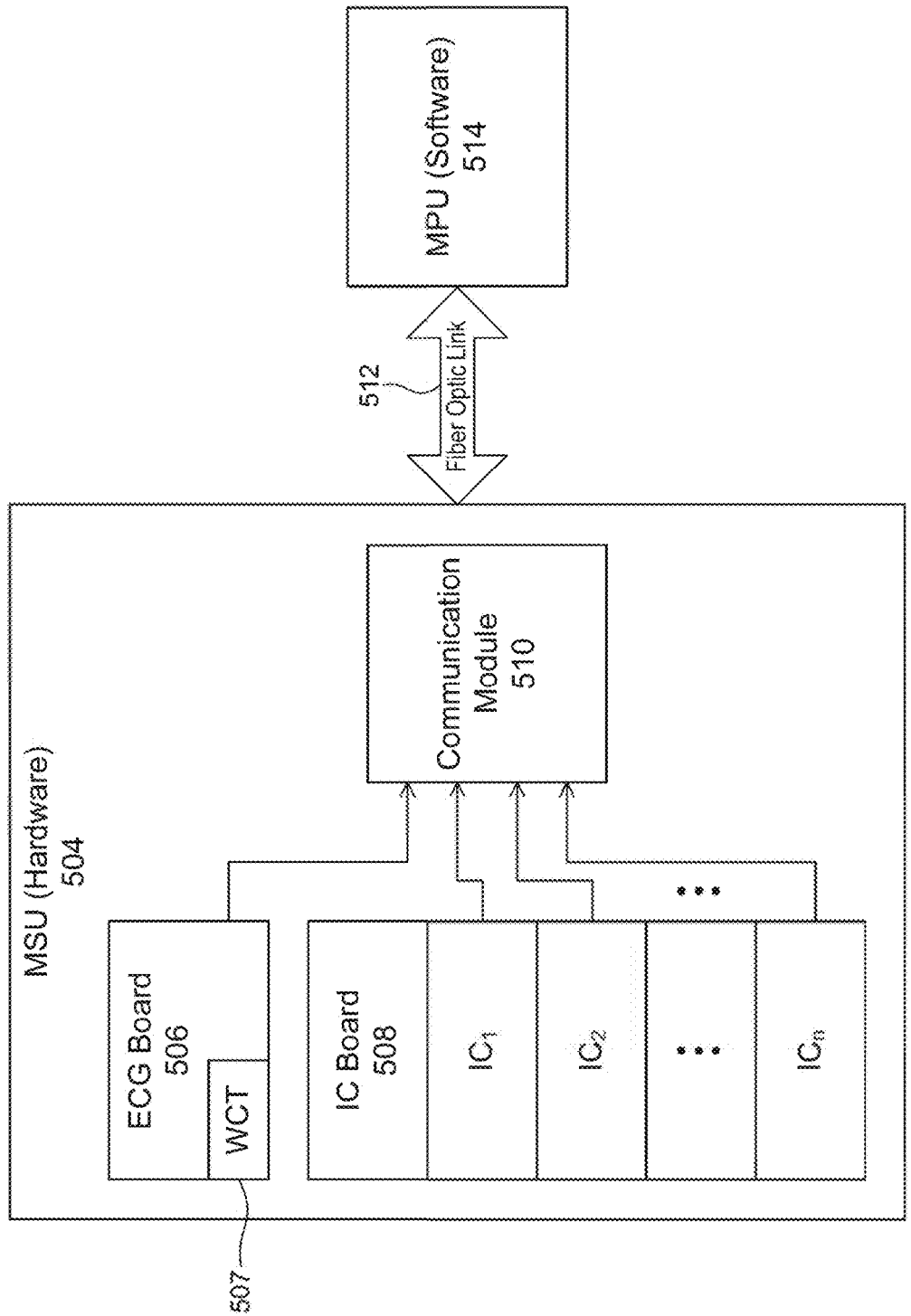
FIG. 5A illustrates a block diagram of the overall EP system, according to some embodiments.

FIG. 5A is a block diagram 500 of the overall EP system disclosed herein, according to some embodiments, generally showing the interface of the Main System Unit (MSU) (hardware components) 504 to the Main Processing Unit (MPU) (software components) 514. FIG. 5A is discussed in more detail later in this disclosure.

Figure 5B:
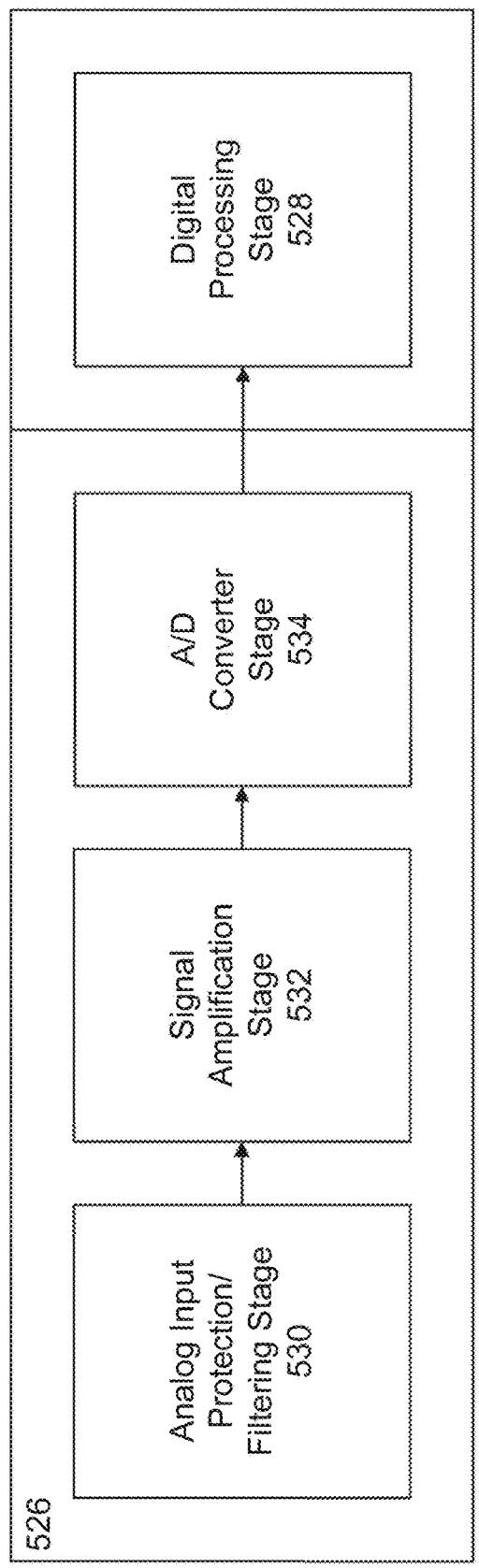
FIG. 5B illustrates a high-level abstraction of the overall EP system hardware and software, according to some embodiments.

FIG. 5B is a block diagram 524 representing the main sections of the EP hardware system input stage 400, with sections 530, 532, 534 cross-referenced to sections shown in the EP hardware system input stage 400.

In FIG. 5B, the analog input protection/filtering stage 530 includes Block 1—Input Protection 402a, Block 2—RF Filter 404a, Block 3—Buffer 406a, Block 4—DC Block 408a, Block 10—Low Frequency Feedback 420a, and Block 11—Shield Drive 422a. The symmetric negative circuitry includes Block 1—Input Protection 402b, Block 2—RF Filter 404b, Block 3—Buffer 406b, Block 4—DC Block 408b, Block 10—Low Frequency Feedback 420b, and Block 11—Shield Drive 422b. The signal amplification stage 532 includes differential circuitry that includes Block 5—Instrumentation Amplifier/Filter 410, Block 6—Differential Amplifier 1/Filter 412, Block 7—Differential Amplifier 2/Filter 414, and Block 9—Large Signal Detection/Fast Recovery 418. The A/D converter stage 534 includes Block 8—the A/D Converter 416. The A/D converter stage 534 also includes a communication module 510 (shown in FIG. 5A) that can format the signals for transmission over fiber optic link 512 to the Digital Processing Stage 528, represented in some embodiments by the MPU 514.

The functionality of the specific Blocks 1-11 of FIG. 4, a single channel of the EP hardware system input stage 400, is described in the following paragraphs.

Analog Input Protection/Filtering Stage

The analog input protection/filtering stage 530 of the EP system, shown in FIG. 5B, includes Block 1—Input Protection 402a, 402b; Block 2—RF Filter 404a, 404b; Block 3—Buffer 406a, 406b; Block 4—DC Block 408a, 408b; Block 10—Low Frequency Feedback 420a, 420b; and Block 11—Shield Drive 422a, 422b. These elements, according to some embodiments, are described in more detail in the following paragraphs.

Input Protection Circuitry

Figure 6A:
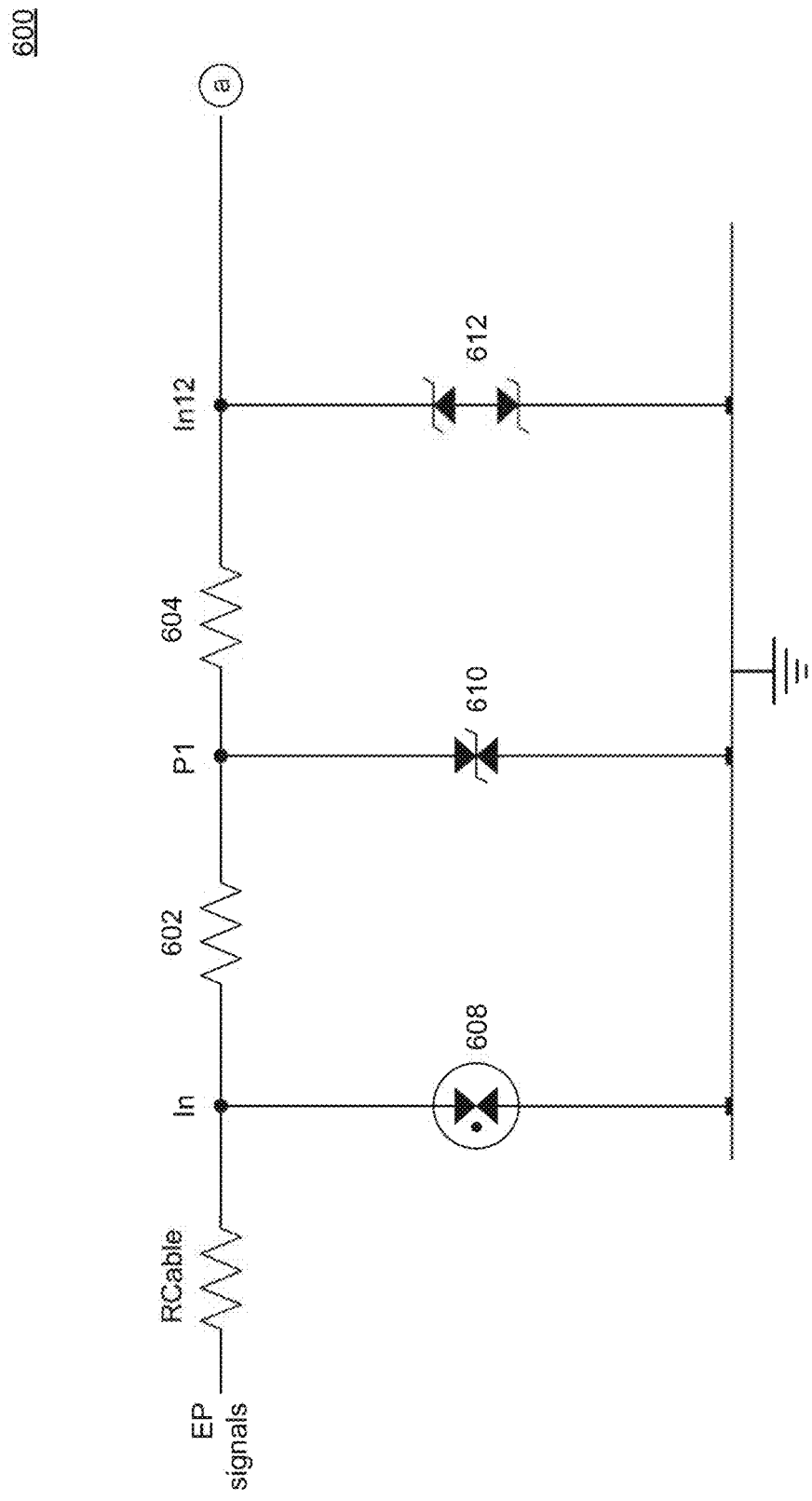
FIG. 6A illustrates a schematic diagram of the large-signal input protection portion of the input protection circuit of the EP hardware system, according to some embodiments.
Figure 6B:
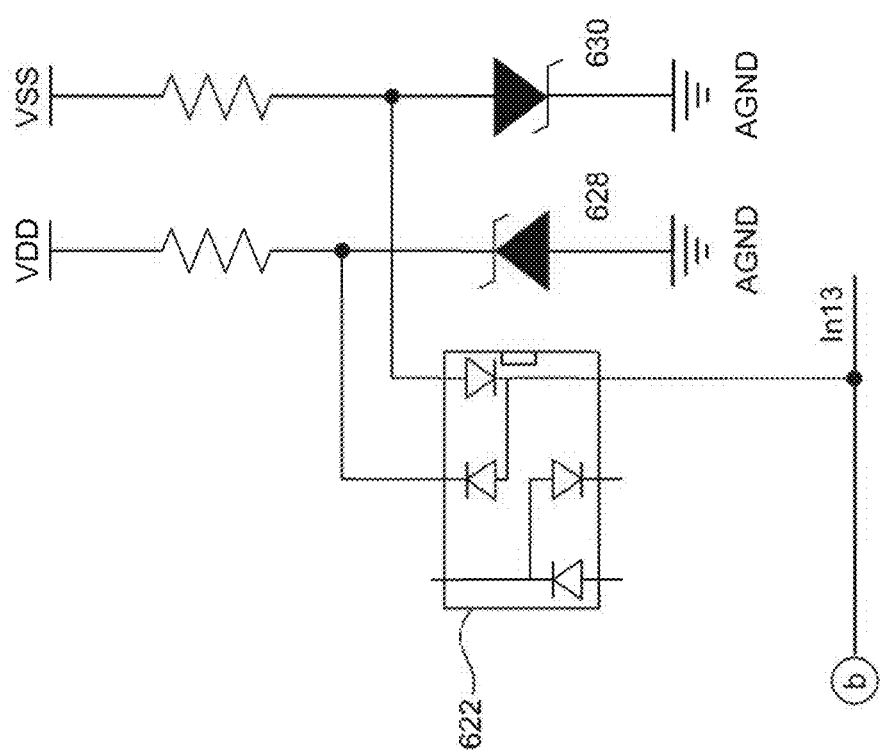
FIG. 6B illustrates a schematic diagram of the electrostatic discharge (ESD) protection portion of the input protection circuit of the EP hardware system, according to some embodiments.
Figure 7:
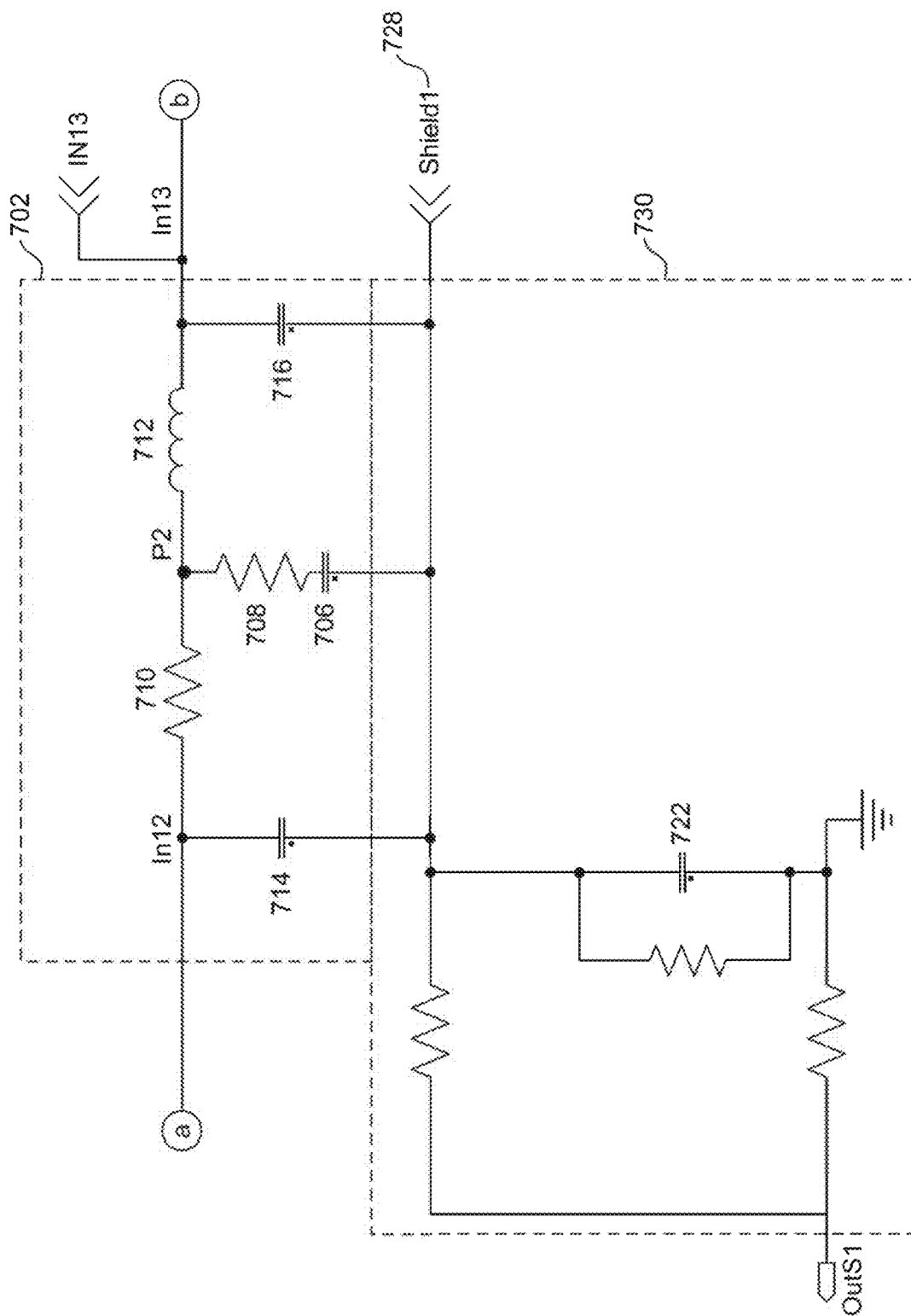
FIG. 7 illustrates a schematic diagram of the radio frequency (RF) filtering portion of the input protection circuit of the EP hardware system, according to some embodiments.

FIGS. 6A, 7, and 6B illustrate circuits that include the analog input protection/filtering stage 530 of the disclosed EP system, according to some embodiments. FIG. 6A illustrates the overvoltage protection circuitry 600 (represented by Block 1 (402a, 402b) in FIG. 4), which can protect the other EP hardware system input stage 400 circuits from large transient voltages, specifically, for example, from defibrillation pulses. The analog input protection/filtering stage 530 can protect against an input voltage that is out of the range of what the circuits can practically handle.

Specifically, the analog input protection/filtering stage 530 can reduce high voltage transients at the ECG, IC, and other electrode lead inputs, which are connected to the patient's body, to less than ten (10) volts, for example, at the inputs to the EP system buffers. The analog input protection/filtering stage 530 can stop a large signal, for example, from a defibrillator, from damaging other portions of the system. In addition, the analog input protection/filtering stage 530 can perform these functions without sinking more than 10%, for example, of the energy of an applied defibrillation pulse, without clamping, or without adding non-linearities when ablation signals are applied.

FIG. 6A illustrates an exemplary embodiment of Block 1's overvoltage protection circuitry 600, including an off-the-shelf gas discharge tube (GDT) 608 that can fire at very high voltages, such as voltages above 300 V, to provide high voltage surge protection. GDT 608 is coupled to two stages of diodes 610, 612 (and resistors 602, 604) designed to sequentially clip the signal to 18 V, for example, to remove a defibrillation signal of up to 5000 V, for example. Diodes 610 represent an off-the-shelf electrostatic discharge (ESD) voltage suppressor device that can aid the GDT 608 until the GDT 608 is fully on. Diodes 612 represent an off-the-shelf bidirectional ESD protection diode that can limit the In2 input of the RF filter (Block 2) to 18 V at the node labeled (a) in FIGS. 6A and 7.

Conventionally, a defibrillation signal of approximately 5000 V would be clamped to +/−5 V to prevent harm. In the case of this disclosure, defibrillation signals can be similarly clamped, but ablation signals with an ablation voltage of approximately 200 V at 500 kHz, for example, can be passed linearly and attenuated by the input resistors RCable, 602, 604 and Block 2 (FIG. 4, 404a, 404b), the RF filter 702.

FIG. 7 illustrates an RF filter/shield drive 700, including an RF filter 702 and a shield drive 730. The RF filter/shield drive 700 connects to the overvoltage protection circuitry 600 of FIG. 6A at the node labeled (a) for the transmission of signal In12 through the analog input protection/filtering stage 530. The RF filter 702 of the RF filter/shield drive 700 is described in more detail below. The shield drive 730 of the RF filter/shield drive 700 is also described below.

The input overvoltage protection circuitry 600 does not clamp the ablation signal; rather, the ablation signal is attenuated linearly (e.g., reduced in direct proportion by the input resistors RCable, 602, 604 and RF filter 702) so that it is not inadvertently altered. For example, if the ablation signal is clamped by the input overvoltage protection circuitry 600, there would be no further access to the contents of that signal above the clamping. Advantageously, linear attenuation of the ablation signal by the disclosed EP system can permit recording small cardiac signals of a few millivolts during ablation. A person of ordinary skill in the art will appreciate that the apparatus, systems, and methods disclosed herein apply similarly to other high-frequency signals that may need to be passed through the protection circuit (e.g., not clamped) to prevent generation of non-linearities that would affect the signals of interest.

FIG. 6B represents ESD input protection circuitry 620 at the final section of the analog input protection/filtering stage 530. The ESD input protection circuitry 620 is coupled to the RF filter/shield drive 700 at the node labeled (b) of FIG. 7. An ESD protection chip 622 can provide ESD protection up to 30 kV for data lines and can respond to overvoltage conditions in nanoseconds. Any number of off-the-shelf ESD protection devices can be used for this purpose.

Transient voltage suppressor (TVS) diodes 628, 630 can provide ESD protection exceeding 16 kV by shunting excess current when the induced voltage exceeds their breakdown voltage. TVS diodes 628, 630 can function as "clamping," or limiting, devices to suppress an overvoltage above their breakdown voltage and can automatically reset when the overvoltage subsides. TVS diodes 622, 630 can also respond to overvoltages faster than other common overvoltage protection components; e.g., "clamping" occurs in about one picosecond. TVS diodes generally can be advantageous for protection against very fast and potentially damaging voltage transients.

Figure 8A:
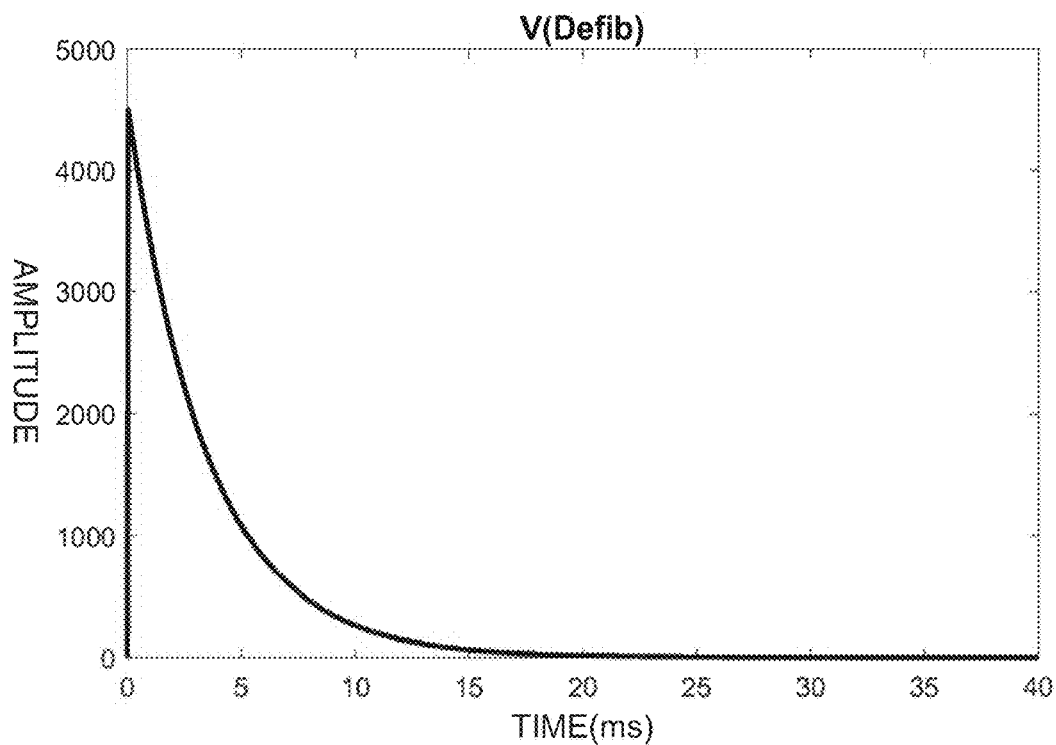
FIGS. 8A-8E illustrate voltage signal plots of a typical defibrillation signal at the input to the input protection circuit, according to an exemplary embodiment.

FIGS. 8A-8E and 9A-9E illustrate sample signal plots to demonstrate how the front-end input protection circuitry handles high voltage transients and ESD, according to an exemplary embodiment. FIG. 8A illustrates the voltage of a representative defibrillator signal, V(Defib), that is applied to the input of the input protection circuit labeled "EP signals" in FIG. 6A. In a laboratory setting, the defibrillator signal can be derived by applying 5000 volts to a 32 µF capacitor and then discharging the capacitor to the connected electrodes on the patient. Because of inductance and resistance, the amplitude received at the electrodes is approximately 4500 volts lasting some tens of milliseconds.

Figure 8B:
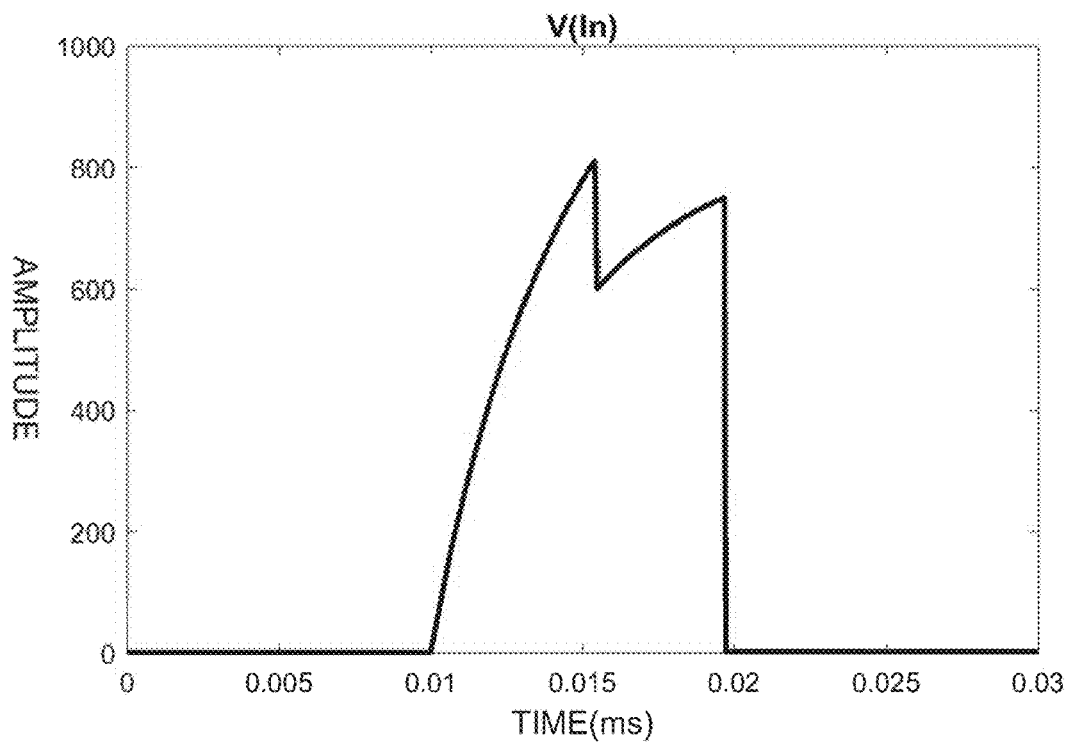
Figure 8C:
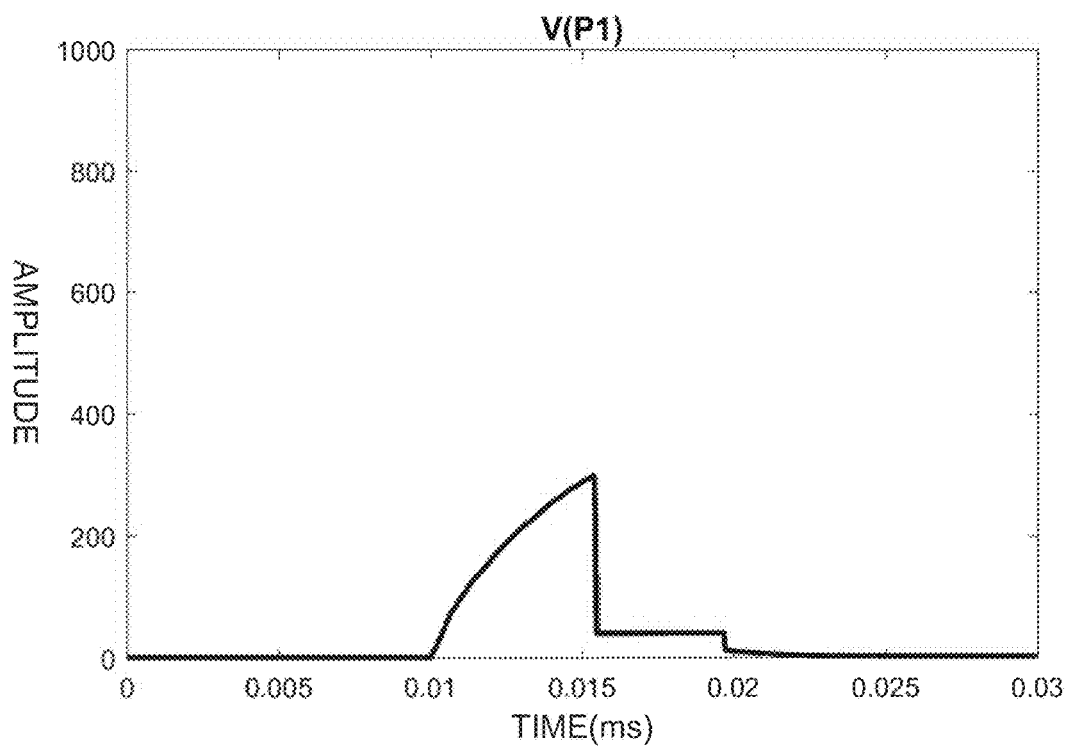

FIGS. 8B-8E illustrate the different voltage levels as the defibrillation signal proceeds through the circuit. V(In) of FIG. 8B is the voltage on GDT 608 of FIG. 6A. GDTs have very low capacitance (e.g., less than 1 pF) and high impedance (e.g., greater than 100 MOhms) in the off state. They function as a gap between two electrodes. When GDTs ionize and turn on, they may have very low resistance (e.g., a few Ohms) with large current carrying capability (e.g., carrying 10s of amperes); thus, they act as a short circuit. A disadvantage of GDTs is that they can take some time to turn on, as the plot for V(In) in FIG. 8B shows. GDTs should trigger at 230 V, but the voltage rises to a much higher level before they turn on effectively and start to conduct. Turn-on time can be several hundred nanoseconds. A resistor RCable in FIG. 6A limits the current going into the GDT 608. This can reduce the power that is dissipated in the system and can also ensure that the analog input protection/filtering stage 530 does not shunt any appreciable power meant for the patient.

The ESD voltage suppressor diodes 610 in FIG. 6A can turn on much faster, within a nanosecond, for example, but have a lower power/energy capacity such that they can activate quickly. They can hold the voltage at P1, as shown in the signal plot for V(P1) of FIG. 8C, to around 30 V while the GDT 608 turns on fully. When the GDT 608 is on fully, the ESD voltage suppressor diodes 610 are no longer active.

Figure 8D:
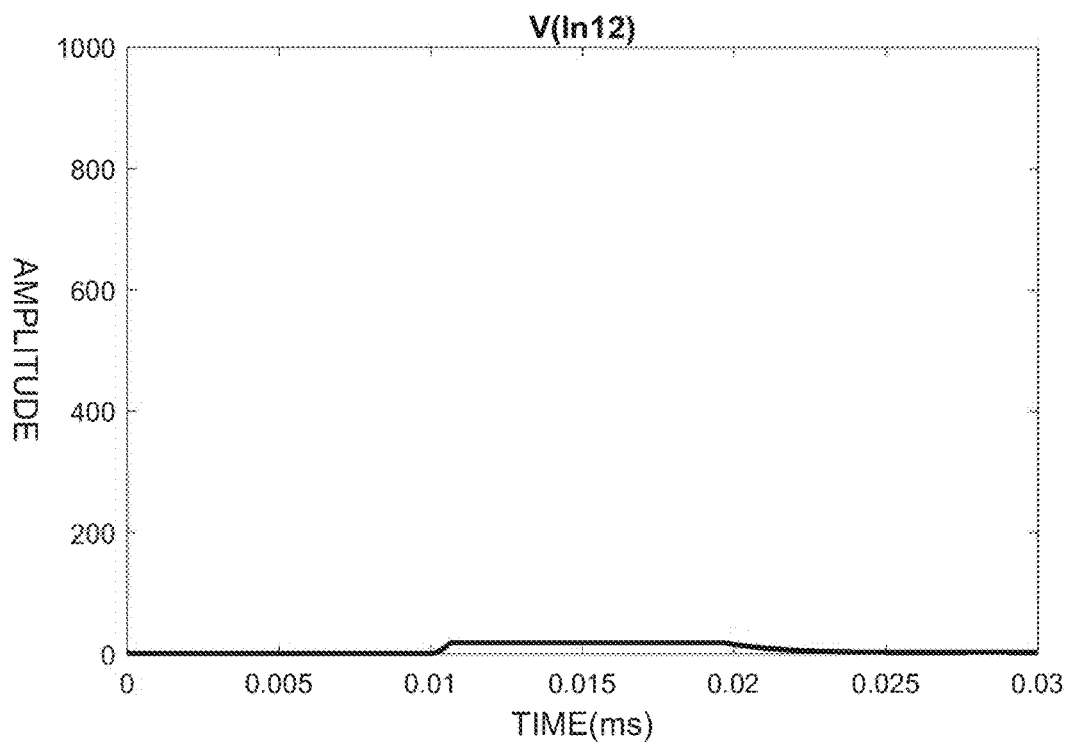

The next stage in FIG. 6A is a bidirectional pair of ESD protection diodes 612 that can limit the signal at In12, the input to the RF filter (Block 2), to approximately 18 V, as shown in the signal plot for V(In12) of FIG. 8D. The signal through the RF filter is further described below in the RF filter (Block 2) section.

Figure 8E:
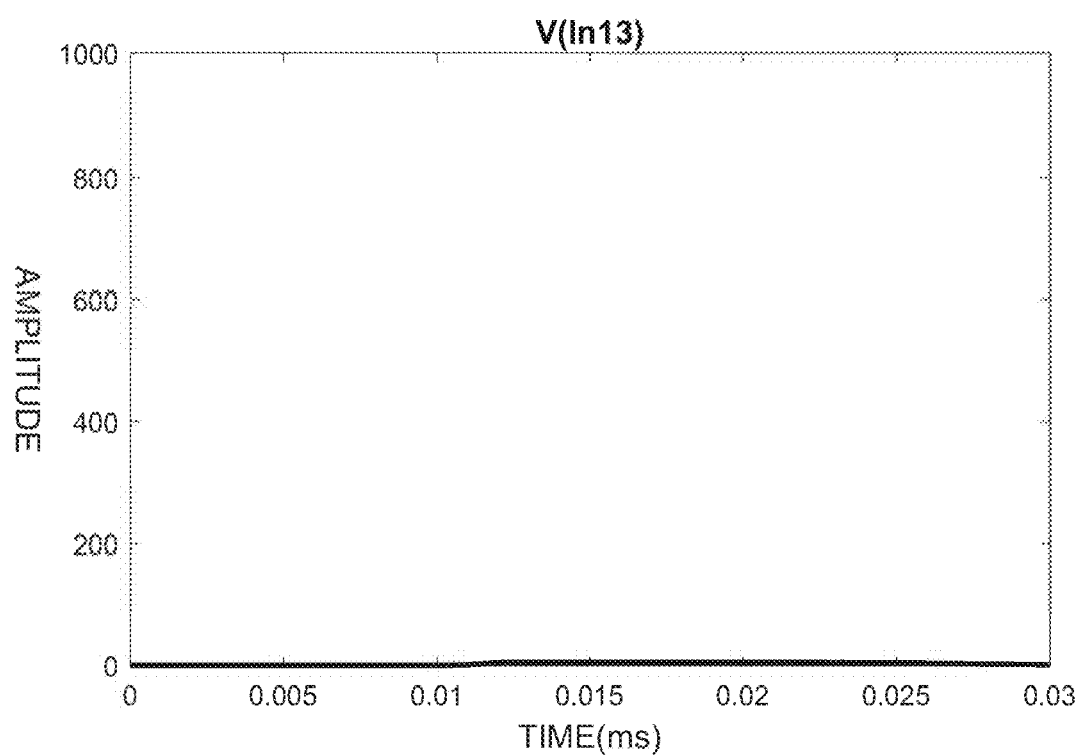

Finally, as shown in FIG. 6B, at In13, after the signal has been filtered by the RF filter of Block 1, an ESD protection chip 622 can clip the signal at VDD+/− a diode drop (e.g., +/−5.7 volts), as shown in the signal plot for V(In13) of FIG. 8E.

A person of ordinary skill in the art will understand that the combination of input protection circuitry shown in FIGS. 6A and 6B, including GDT 608, diodes 610, diodes 612, ESD protection chip 622, and TVS diodes 628, 630, protects the circuitry of an EP recording system. However, this circuitry by itself can be detrimental to achieving a quality EP recording during ablation. For example, if the ablation signals were clipped, the non-linearities produced may cause noise and mask the cardiac signals of interest. Because a medical team may want to see the cardiac signals during ablation, the integration of the Block 2 RF filter with the input protection circuitry is an improvement over conventional solutions. The disclosed embodiments allow unwanted and potentially disruptive or damaging signals to be attenuated while linearly filtering an ablation signal and monitoring ECG and IC signals.

Figure 9A:
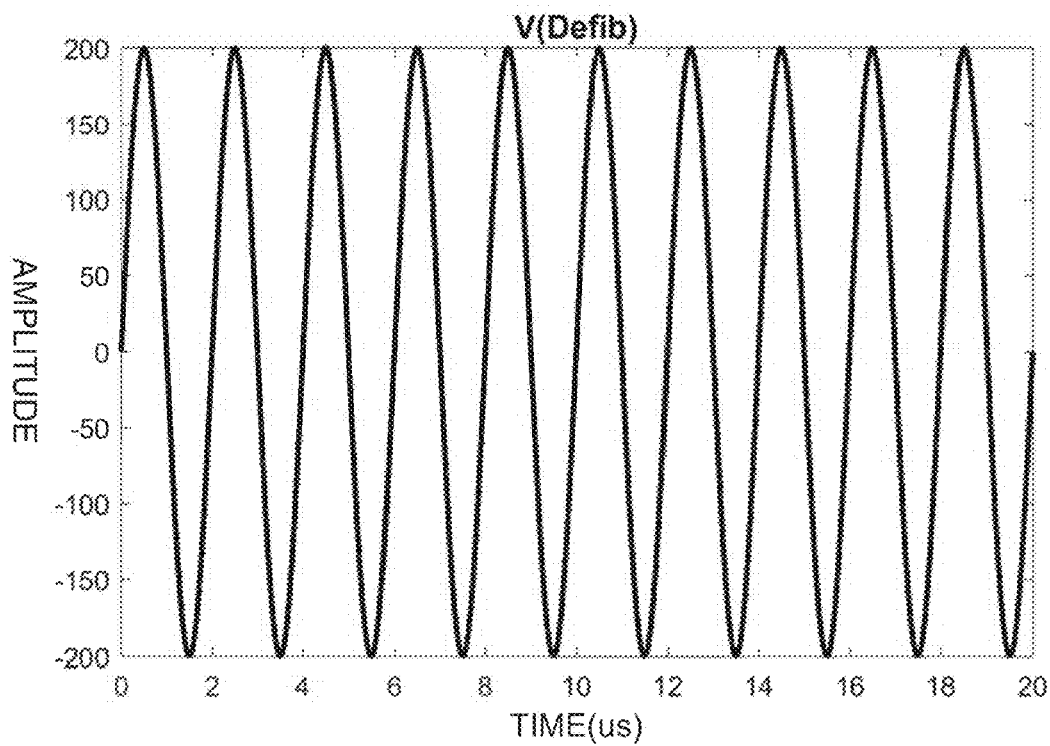
FIGS. 9A-9E illustrate voltage signal plots of a typical ablation signal at the input to the input protection circuit, according to an exemplary embodiment.
Figure 9B:
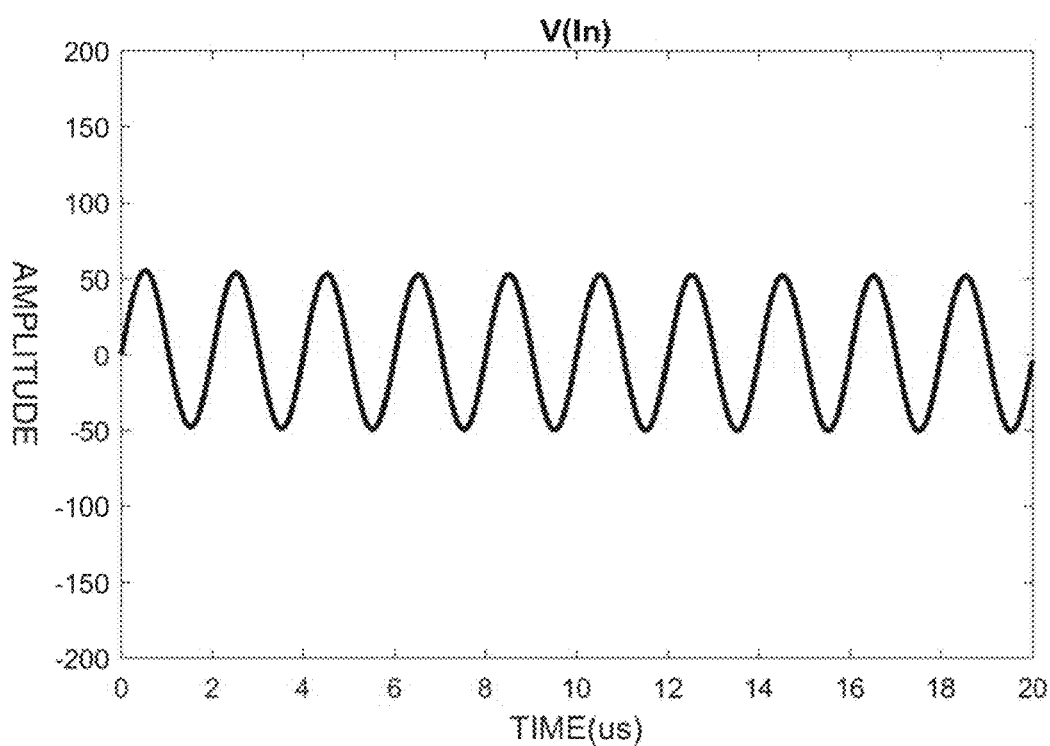
Figure 9C:
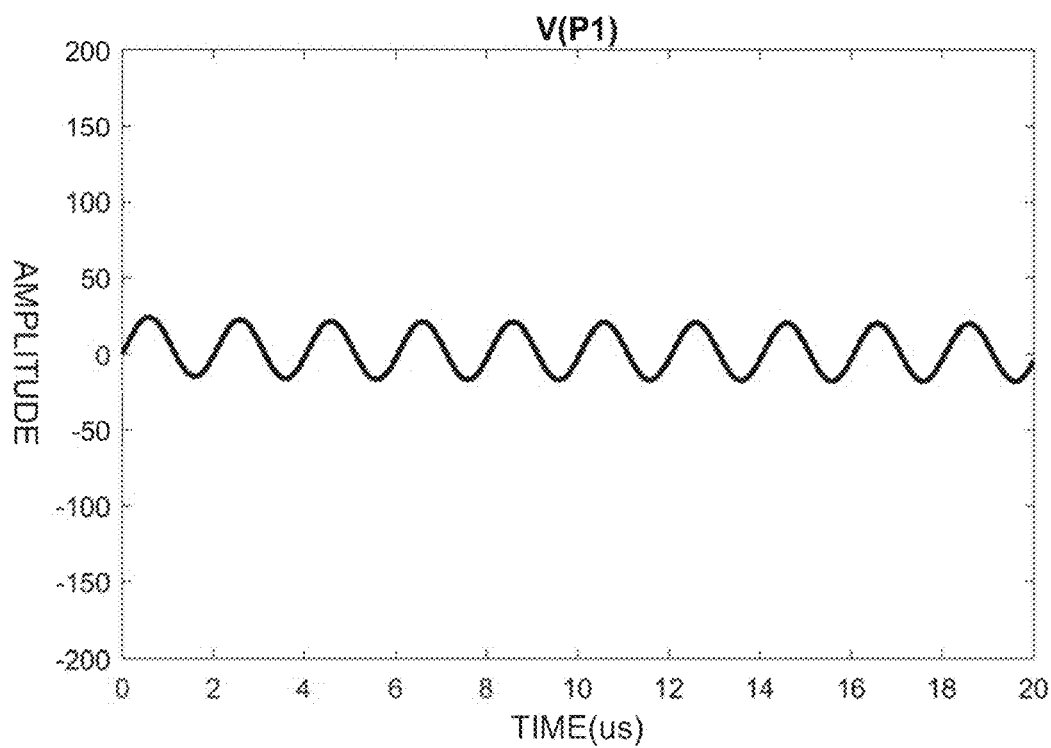
Figure 9D:
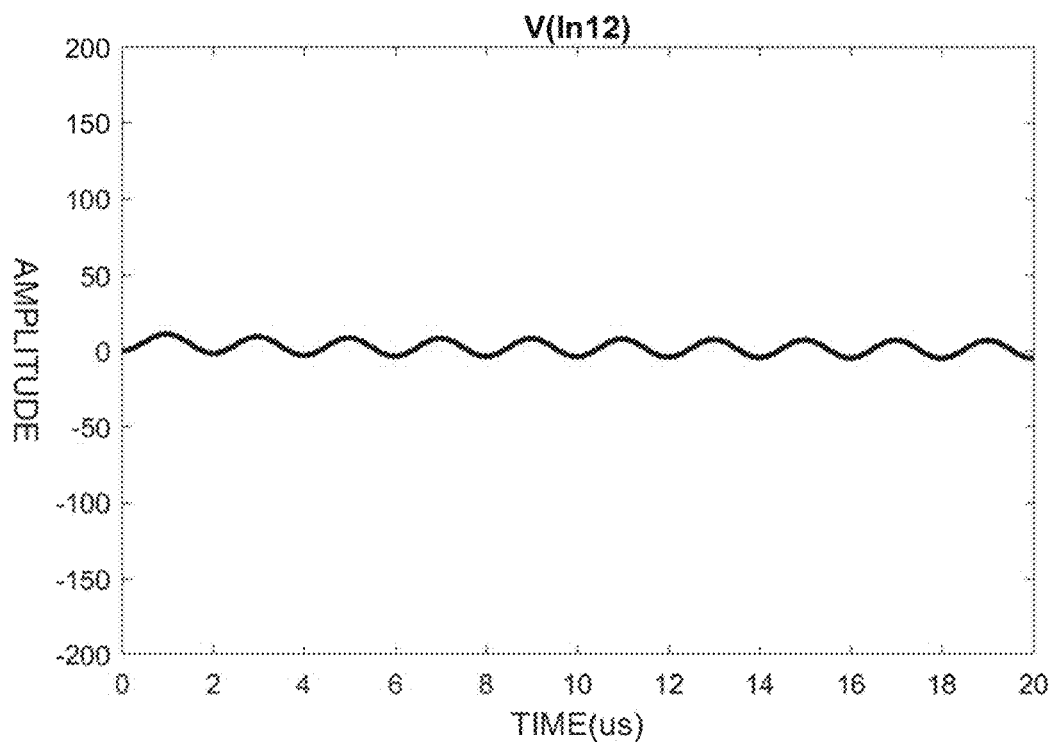
Figure 9E:
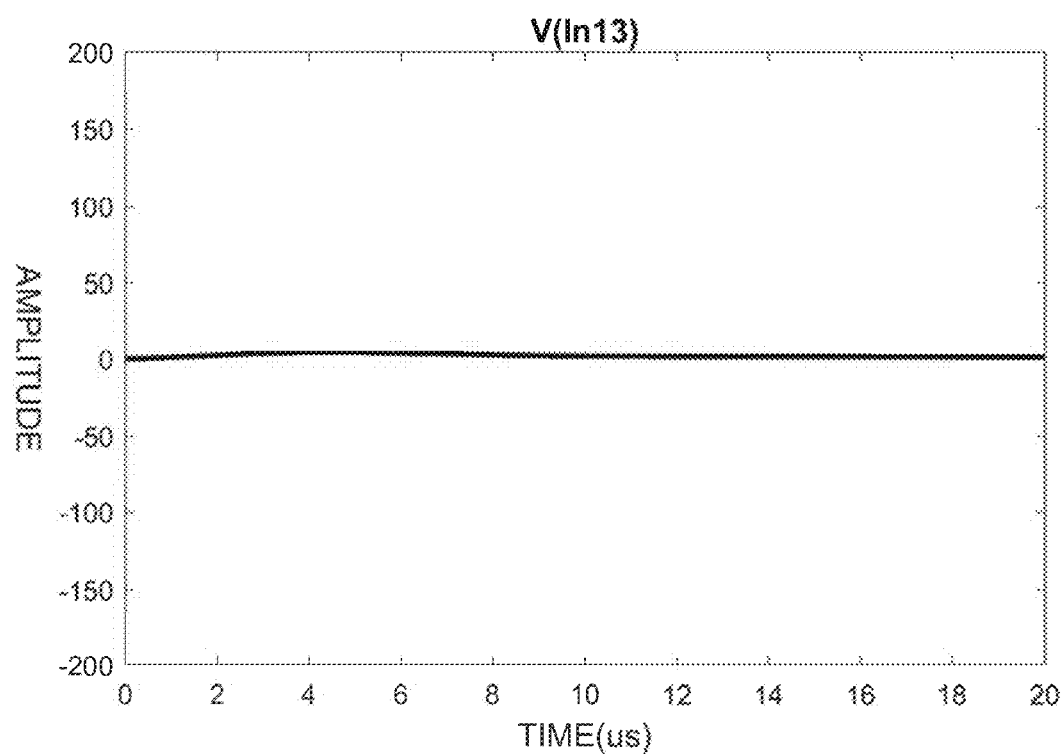

For example, FIGS. 9A-9E are signal plots that illustrate the progression of an ablation signal through the input protection circuit of FIGS. 6A, 7, and 6B. The ablation input is 400 Vpp at the sensor electrodes, as shown by plot V(Defib) in FIG. 9A. As the signal progresses through the stages of the input protection circuit, the signal is attenuated by the resistor RCable (shown as FIG. 9B plot V(In)), resistor 602 (shown as FIG. 9C plot V(P1)), resistor 604 (shown as FIG. 9D plot V(In12)), and capacitor 716 (shown as FIG. 9E plot V(In13)). The ablation signal voltage levels are 100 Vpp at node In of FIG. 6A, 12 Vpp at node In12 of FIG. 6A, and 60 mV at node In13, after the RF filter of FIG. 7. The ablation signal does not trigger the protection devices, but is attenuated linearly, permitting observation and/or recording of the cardiac signals during ablation. The ablation signal can be further filtered at each of the Block 5, 6, and 7 of the signal amplification stage 532 (see FIGS. 4, 5B, and FIG. 10), and at the A/D converter (Block 8 in FIG. 4) that has a 100 dB low-pass filter at 950 Hz.

RF Filter Circuitry with Low-Frequency Feedback and Shield Drive

In addition to its contribution to the input protection circuitry to filter and linearly attenuate ablation signals at the EP system input, RF filter 702 can function in concert with the low-frequency feedback circuit of Block 10 (see FIGS. 4, 420a and 420b, and FIG. 16, 1600) to enable the overall circuit to continue linear attenuation of ablation signals (e.g., with voltage amplitude of about 200 V in the frequency range of about 300 kHz to about 600 kHz) during cardiac monitoring, in near real-time, while passing small cardiac signals (e.g., having a frequency range of about 0.01 Hz to about 500 Hz), for example.

The RF filter 702 can be designed to linearly attenuate the amplitude of the ablation signal by at least 75% in some embodiments, or even by at least 90% in other embodiments, for example. The RF filter 702 can be designed to provide substantially no attenuation to an input signal having a frequency less than 5 kHz, for example. This RF filter 702 can also function in concert with the shield drive 730 of Block 11 (see FIGS. 4, 422a and 422b, and FIG. 7), which can work with input capacitors 706, 714, 716 of RF filter 702 to help maintain high input impedance of the overall circuit. This high input impedance can help minimize the input losses of the cardiac signal of interest. The shield drive 730 is further discussed below.

Low-Frequency Feedback Circuit

Block 10 (see FIGS. 4, 420a and 420b), a low-frequency feedback circuit 1600, can provide positive feedback to the Block 2 RF filter (see FIGS. 4, 404a and 404b, and FIG. 7, 702) to increase input impedance to the EP system, thus reducing signal attenuation. This is advantageous because the input impedance of the EP system in the frequency range of the cardiac signals can be compromised by the RF filter 702.

Figure 10:
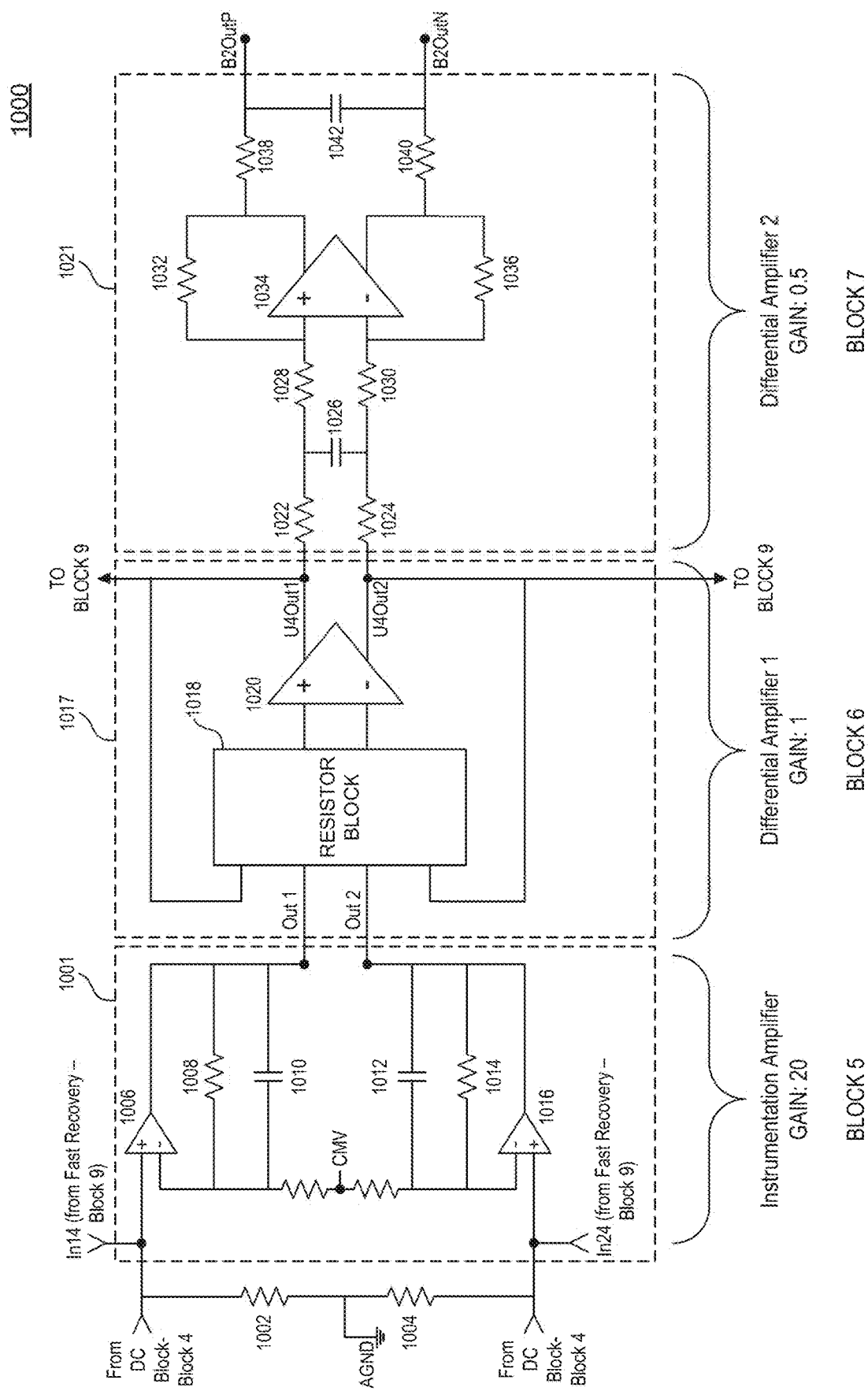
FIG. 10 illustrates a schematic diagram of the instrumentation and gain stages of the EP hardware system, according to some embodiments.

Specifically, high input impedance at the instrumentation amplifier 1001 of FIG. 10 can be greatly reduced depending on the frequency of the input signal (e.g., by a factor of 100 at 60 Hz) by the presence of the RLC network elements 706, 708, 714, 716 of the RF filter 702. Although the RF filter 702 is advantageous at ablation frequencies, reduction of impedance at low frequencies can reduce the amplitude of the cardiac signals and affect common mode rejection. Without mitigating the effect of the RF filter 702, the advantages of the instrumentation amplifier 1001 would otherwise be lost.

To mitigate that loss and maintain high common mode rejection (e.g., on the order of 100 dB), it is desirable to maintain high impedances at the power line frequencies so that variations in source impedance do not convert common mode signals into differential signals. The Block 10 low-frequency feedback circuit 1600 illustrated in FIG. 16 receives the buffered version of the signal of interest from the Block 3 buffer 406a, 406b as Buf1 1602. The low-frequency feedback circuit 1600 then applies operational amplifier 1606 to drive Shield1 728 at the base (that is, bottom plate) of the capacitors 706, 714, 716 in RF filter 702. Specifically, the operational amplifier 1606 serves as a driver to eliminate loading effects and maintain the high input impedance of the analog input protection/filtering stage 530 into the signal amplification stage 532.

When the Block 10 low-frequency feedback circuit 1600 drives the RF filter 702 at low frequencies, there is little or no voltage variation across the capacitors 714, 716. Thus, at low frequencies, capacitors 706, 714, 716 act as open circuits and the high input impedance is maintained. But at higher frequencies, the feedback from the Block 10 low-frequency feedback circuit 1600 is reduced due to the low-pass filtering functionality of Block 10.

Specifically, the combination of a capacitor 1666 and a resistor 1693 at the inverting input to the operational amplifier 1606 filters high frequencies. The output of this circuit no longer tracks the input and holds the Shield1 728 (also the reference node of the RF filter 702) to a fixed level with respect to high frequency signals. This enables the RF filter's 702 passive RLC network 706, 708, 710, 712, 714, 716 to attenuate the high frequency signals.

Specifically, the Block 10 low-frequency feedback circuit 1600 (see also FIGS. 4, 420a and 420b) takes the buffered signal from the Block 3 Buffer circuit (see FIGS. 4, 406a and 406b) and produces a correcting signal to Shield1 728 of FIG. 7, that is, the equivalent of the input as a feedback signal at the capacitors 706, 714, 716 of the Block 2 (see FIGS. 4, 404a and 404b) RF filter 702. This feedback to the capacitors 706, 714, 716 is provided as a dynamic current source for the circuit.

The RF filter 702 of Block 2 404a, 404b is enabled for filtering at high frequencies, but the RF filter 702 is disabled at low frequencies when receiving feedback from the low-frequency feedback circuit 1600 of Block 10 420a, 420b. At high frequencies, the capacitors 706, 714, 716 in the RF filter 702 function as shunting capacitors that effectively short circuit signals at RF frequencies. The impedance of the capacitors 706, 714, 716 decreases linearly as the frequency becomes higher. The low-frequency feedback circuit 1600 does not affect the EP system at high frequencies.

At low frequencies, the low-frequency feedback correcting signal, Shield1 728 from Block 10 (see FIG. 16) to Block 11 (shield drive 730 of FIG. 7), drives the bottom plates of the capacitors 706, 714, 716, such that these capacitors mimic the input signal. This controls the reference node of the RF filter 702. Specifically, the voltage at the plates of the capacitors 706, 714, 716 vary in sync with each other, and the low-frequency feedback circuit 1600 drives the bottom plate of the capacitors 706, 714, 716 of the RF filter 702 to be the same voltage as the upper plate, such that the voltage difference at the plates of the capacitors 706, 714, 716 becomes zero and the capacitors 706, 714, 716 act as open circuits.

The goal of the low-frequency feedback is to drive the difference between Shield1 728 and Buf1 1602 to zero, such that Shield1 728 equals Buf1 1602. When this occurs, input capacitance can be eliminated. At high frequencies, the positive feedback from operational amplifier 1606 is reduced to zero. In addition, at high frequencies capacitor 722 (which is 30 times larger than other capacitors in the circuit, for example) acts as a short circuit between Shield1 728 and ground. This effectively grounds the reference node of the RF filter 702, fully enabling it to attenuate RF frequencies. Thus, the Block 10 low-frequency feedback circuit 1600 works in concert with a unique arrangement of the Block 2 RF filter 702 elements to remove the loading effect of the RF filter 702 before passing signals to the Block 5 instrumentation amplifier 1001.

In this manner, the instrumentation amplifier 1001 can condition cardiac signals without the overlying ablation signal. The result is that the input to the overall circuit at low frequencies still sees a very high input impedance (e.g., on the order of 10s of MOhms) that is advantageous to visualizing high-fidelity cardiac signals in an EP environment. Additionally, Block 10 is a symmetric (e.g., mirrored) circuit, so that common mode noise is subtracted as the signal propagates through the circuit. Another advantage of the low-frequency feedback circuit 1600 is that its output Shield1 728 can be used to drive the outer shields of the input cables, for example, at OutS1 of the shield drive 730 of FIG. 7.

Shield Drive Circuit

Block 11 (see FIGS. 4, 422a and 422b), specifically the shield drive 730, shown in FIG. 7, receives the output of the low-frequency feedback circuit 1600 (Shield1 728 of FIG. 16) of Block 10 (see FIGS. 4, 420a and 420b) and provides positive feedback to the cable shields at OutS1, thus reducing the effective input capacitance of the input cables. Therefore, the path from the bottom plate of the input capacitors 714, 716 in the RF filter 702 of Block 2 (see FIGS. 4, 404a and 404b), to the shields of the input cables, further contributes to making the input impedance as large as possible. This high input impedance minimizes the input losses of the cardiac signal of interest. In some embodiments, the shield drive connections are grounded if a shield drive is not desired.

Signal Buffering and DC Blocking Circuitry

Block 3 (see FIGS. 4, 406a and 406b) is a low-noise unity gain driver that aids in minimizing the input losses of cardiac signals. Specifically, it can provide the high input impedance to minimize the load of the input stage to the cardiac signals and to drive the signal amplification stage 532. In Block 3, two operational amplifiers (circuit not shown) form two buffers that serve as a unity gain follower that buffers the input and gives the input a high input impedance.

Block 4, the DC Block (see FIGS. 4, 408a and 408b), is a high-pass module (circuit not shown) that prevents input offsets from the sensor/tissue interface of the patient's body from entering the amplifier gain stages. In Block 4, two DC blocking capacitors (not shown) immunize the input from the large offsets from catheters.

Signal Amplification Stage

The signal amplification stage 532 (see FIG. 5B) of the EP system includes differential circuitry: Block 5—Instrumentation Amplifier/Filter 410, Block 6—Differential Amplifier 1/Filter 412, Block 7—Differential Amplifier 2/Filter 414, and Block 9—Large Signal Detection/Fast Recovery Circuit 418. These circuits are described in more detail in the following paragraphs.

Instrumentation Amplifier/Filter Circuitry

Block 5 (see FIG. 4, 410) is an instrumentation amplifier/filter that provides amplification to the differential signal and common mode rejection of unwanted signals, specifically, power line noise and related harmonics, from the equipment laboratory or medical environment. Block 5, detailed in FIG. 10, has a gain stage 1001 with a differential gain of about 20 at its output, and it provides additional filtering for RF attenuation through its RC network 1008, 1010, 1012, 1014. Two operational amplifiers 1006, 1016, for example, are low-noise devices, designed to receive cardiac signals at the input to the instrumentation amplifier 1001, before the cardiac signals have been amplified. The differential signal from the Block 5 instrumentation amplifier 1001 then enters the precision resistor block 1018 of the Block 6 differential amplifier #1 1017.

Differential Amplifier/Filter Circuitry

Block 6 (see FIG. 4, 412) has a differential amplifier 1020 that produces a fully differential output with a unity gain, as referenced to common mode voltage. Block 6 differential amplifier #1 1017 can provide additional filtering for RF attenuation. Maintaining a fully differential signal path helps reduce noise from entering from the digital part of the system. Such noise would appear mainly as common mode noise and get rejected. This part of the signal amplification stage 532 also shifts the DC bias of the cardiac signal from 0 up to 2.5 V and limits its output from 0 to 5 V.

At an output of Block 6, having a first fully differential amplifier 1020 referenced to common mode, the common mode level is set to 2.5 V as the signals enter Block 7 differential amplifier #2 1021. The circuit continues the low-pass filtering of the ablation signal to the outputs (B2OutP, B2OutN) of Block 7. Block 7, having a second fully differential amplifier 1034 similar to Block 6's differential amplifier 1020, has a gain of about 0.5, with additional filtering for RF attenuation provided by circuit elements 1022, 1024, 1026, 1028, 1030, 1032, 1036, 1038, 1040, 1042. This part of the signal amplification stage 532 maintains the fully differential signal path to continue rejection of noise.

The gain introduced by Block 7 allows the circuit to clip the signal at the input limits of the A/D converter, Block 8 (see FIG. 4, 416), which can be a delta-sigma converter (not shown), for example. As previously mentioned, the Block 6 differential amplifier #1 1017 clips each output signal to +/−2.5 volts relative to the bias level of 2.5 volts. With gain of 0.5, the outputs of the Block 7 differential amplifier #2 1021 produce signals biased at 2.5 volts with a range of +/−1.25 volts for each output, or 2.5 volts peak-to-peak differential. This represents the limits of a 24-bit A/D converter 416, for example, in some embodiments. By clipping and matching the output limits, the input of the A/D converter 416 is prevented from being overdriven. Because a delta-sigma converter can behave erratically when overdriven, potentially causing spurious results, it is advantageous that the embodiments allow the full range of inputs to the A/D converter, but no more.

The overall gain of the signal amplification stage 532 of the disclosed EP system can be less than or equal to 20 in some embodiments, or can be less than or equal to 50 in other embodiments, for example. For example, in some embodiments, a gain of about 20 at the output of the instrumentation amplifier 1001, a unity gain at the output of differential amplifier #1 1017, and a gain of about 0.5 at the output of differential amplifier #2 1021 produce a system gain of about 10 at the inputs of the A/D converter 416. Generally, the signal amplification stage 532 can include an instrumentation amplifier 1001 with a gain greater than one (1) at its output, a differential amplifier #1 1017 with a gain of about one (1) at its output, and a differential amplifier #2 1021 with a gain of less than one (1) at its output.

The overall low gain of the system, due to its improved ability to remove noise, provides further improvement over conventional systems. Conventional systems that have a 16-bit A/D converter require high gain in order to visualize small signals that are obscured in the presence of higher-amplitude signals. Conventional systems can have gain of up to 5000, for example, causing saturation of signals to occur quickly. Further, if lower gain is used with a 16-bit converter, quantization noise can adversely affect the output results. With the disclosed system having a low gain of about 10, coupled to a 24-bit A/D converter, saturation is prevented until at least 250 mV, for example, of small-signal input, and quantization noise is avoided.

Fast Recovery/Large-Signal Detection/Fast Recovery Circuitry

Figure 11:
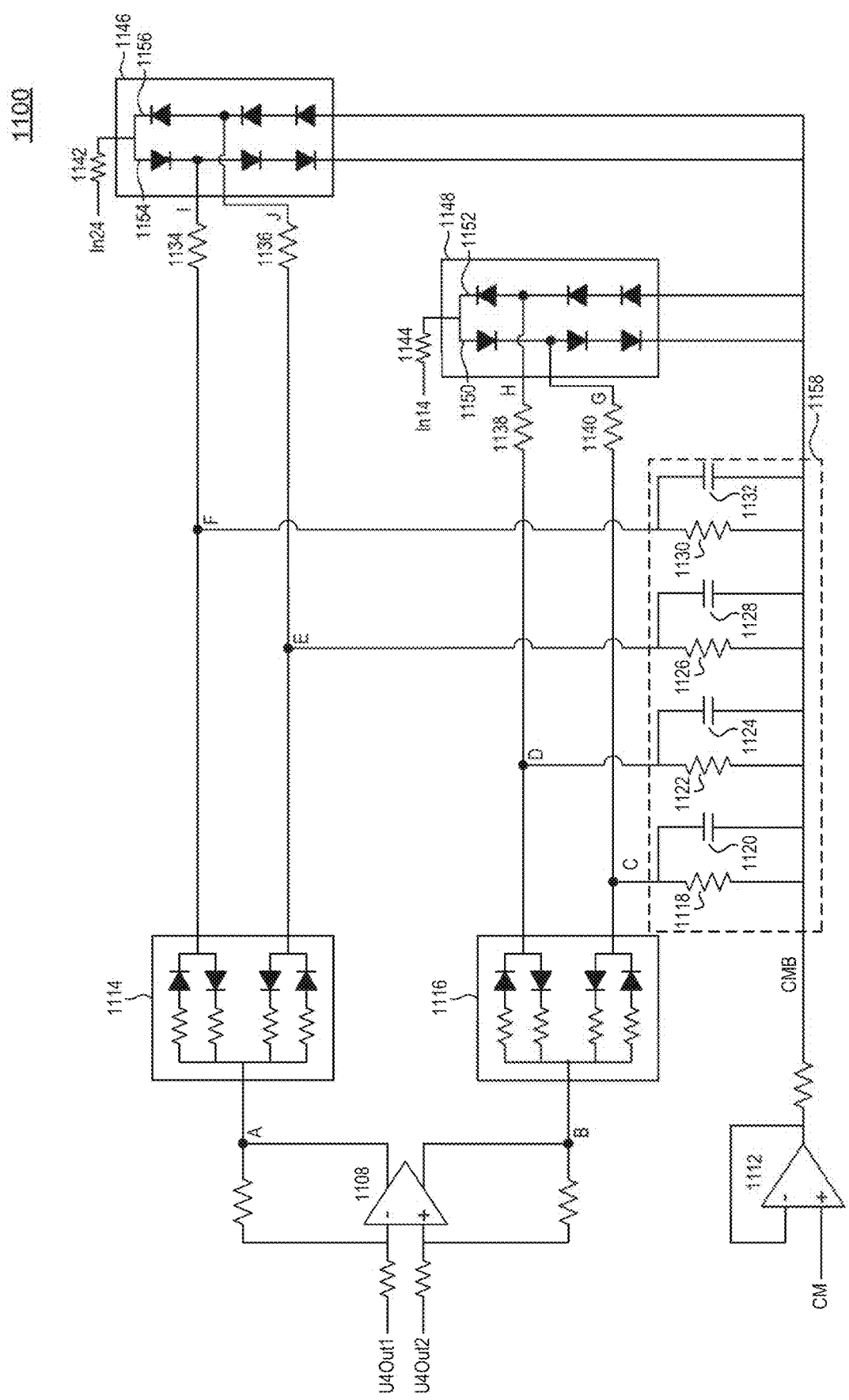
FIG. 11 illustrates a schematic diagram of a large-signal detection/fast recovery circuit of the EP hardware system, according to some embodiments.

The outputs from the Block 6 differential amplifier #1 1017, in addition to being passed to the Block 7 differential amplifier #2 1021, also are passed to Block 9 (see FIG. 4, 418 and FIG. 10), the large-signal detection/fast recovery circuit 1100 of FIG. 11. The large-signal detection/fast recovery circuit 1100 can remove large signals and recover quickly from large transients. This circuit is thus called a "fast recovery" circuit because of its improved ability to recover from saturation much faster than conventionally achieved.

Specifically, the large-signal detection/fast recovery circuit 1100 can detect that the differential input signal has been in excess of 100 mV, for example, for a duration of at least 10 milliseconds, which is identified as an abnormal operating range. On detection of this state, the large-signal detection/fast recovery circuit 1100 can reduce the time constant after the Block 4 DC blocking stage (see FIGS. 4, 408a and 408b) to ensure that the cardiac signal does not remain in saturation. But, the large-signal detection/fast recovery circuit 1100 can have negligible effect under normal operation. For example, the large-signal detection/fast recovery circuit 1100 can have no effect on fast transients produced by pacing, which can be a signal of interest to monitor and record in an EP environment, and which can have transients that last generally less than 10 milliseconds.

In an embodiment, the first stage of the large-signal detection/fast recovery circuit 1100 has two operational amplifiers 1108, 1112, for example. The gain of the operational amplifier 1108 (e.g., about 40) determines the activation threshold, that is, at which signal amplitude the large-signal detection/fast recovery circuit 1100 can operate to limit (or "soft clamp") a signal. The activation threshold determines how large the signal must be before the large-signal detection/fast recovery circuit 1100 becomes active and begins to pull the voltages at nodes In14 and In24 toward the common mode level. For example, operational amplifier 1108, with a gain of about 80, can activate the large-signal detection/fast recovery circuit 1100 at about 50 mV; with a gain of about 40, can activate the large-signal detection/fast recovery circuit 1100 at about 100 mV; and with a gain of about 20, can activate the large-signal detection/fast recovery circuit 1100 at about 200 mV. When the signal amplitude reaches the set amplitude level determined by the gain, the voltage will be enough to overcome the activation threshold of a first pair of diode stages 1114, 1116 to activate the large-signal detection/fast recovery circuit 1100.

Operational amplifier 1112 produces a unity gain to buffer the common mode (CM) signal, which provides a common mode reference for the signals through operational amplifier 1108. Operational amplifier 1108 receives U4Out1 and U4Out2 signals from Block 6 (see FIG. 10). Accordingly, the average of the U4Out1 and U4Out2 signals is referenced to the common mode node (CMB of FIG. 11). The signals out of operational amplifier 1108 pass through the first pair of diode stages 1114, 1116 that limit the charging of the subsequent capacitors 1120, 1124, 1128, 1132. These capacitors 1120, 1124, 1128, 1132, which accumulate a charge from the buffered U4Out1 and U4Out2 signals, produce the maximum positive (+) and negative (−) charges for both the inverting and non-inverting version of signals U4Out1 and U4Out2.

The capacitors 1120, 1124, 1128, 1132 form an RC network at nodes C, D, E, and F with resistors 1118, 1122, 1126, 1130, which together serves as a timing network that determines a time constant. The time constant determines how long the signals can be at their maximum amplitude before the large-signal detection/fast recovery circuit 1100 pulls the voltages at nodes In14 and In24 toward CM. This RC network is hereinafter referred to as "timing banks" 1158. Some embodiments of the timing banks 1158 may be designed to produce a time constant of at least 10 milliseconds, for example, to prevent activation of the large-signal detection/fast recovery circuit 1100 during pacing signals of 2-milliseconds to 10-milliseconds duration, for example. Other embodiments may be designed to produce a time constant of at least five (5) milliseconds.

When the capacitors 1120, 1124, 1128, 1132 charge up, a difference is detected, and the signal passes through a second pair of diode stages 1146, 1148, which limits (or "soft clamps") the input to between about +/−100 mV, for example. This prevents the system from saturating for any appreciable amount of time (e.g., less than 100 milliseconds). The second pair of diode stages 1146, 1148 also ensures that there is no interaction between the large-signal detection/fast recovery circuit 1100 and the EP system if a signal is not large/long enough to require limiting. In other words, when it is not advantageous to activate the large-signal detection/fast recovery circuit 1100, the second pair of diode stages 1146, 1148 disconnects the large-signal detection/fast recovery circuit 1100. The Block 9 large-signal detection/fast recovery circuit 1100 ensures that the EP system is not affected by large signal spikes, and allows a steady-state response where the difference between the inverting and non-inverting U4Out1 and U4Out2 signals is about 100 mV, for example, where operational amplifier 1108 has a gain of about 40, for example.

The Block 9 large-signal detection/fast recovery circuit 1100 is situated in the EP system at a location to remove a large-signal voltage offset. A person of ordinary skill in the art will appreciate that the large signal detection/fast recovery circuit 1100 could be located elsewhere in the EP system where potential large signal spikes may occur and are unwanted. A person of ordinary skill in the art will also appreciate that electronic components, such as the capacitors 1120, 1124, 1128, 1132 and the resistors 1118, 1122, 1126, 1130 of the timing banks 1158, can be substituted within the large signal detection/fast recovery circuit 1100 to change circuit activation levels and times. The large-signal detection/fast recovery circuit 1100 can be used in various embodiments of other signal acquisition and processing systems to remove a large-signal voltage offset from other types of electrical signals, as would be appreciated by a personal of ordinary skill in the art.

In some embodiments, the outputs In14, In24 of the Block 9 large-signal detection/fast recovery circuit 1100 (see FIG. 4, 418) are fed back into Block 4, the DC Block (see FIGS. 4, 408*a* and 408*b*). The DC blocking capacitors of Block 4 (not shown) add an additional bias (e.g., a correcting bias) back to the input signals. Accordingly, a signal from the Block 9 large-signal detection/fast recovery circuit 1100 is not fed back into the Block 4 DC Block unless the signal fed into Block 9 is large (e.g., with an amplitude on the order of 100 mV or greater). In other words, the output signal of Block 9 does not pass into Block 4 unless a large signal event occurs. Nodes In14 and In24 are normally disconnected.

The exemplary embodiment of the large-signal detection/fast recovery circuit 1100 of FIG. 11 is described in detail relative to the signal plots of FIGS. 12, 13A-13C, 14A-14D, and 15A-15B. A sample signal is applied at the inputs to the EP system, and described at various points through the circuit. In this example, the signals shown to demonstrate the large-signal detection/fast recovery circuit 1100 are generated by applying a 20 mVpp signal at node In12 of FIG. 6A and FIG. 7, and zero input at node In22 (the symmetric negative node, not shown), specifically, the inputs to the RF filter 702. At time 10 msec, a 200 mV step is added to the signal at node In12. This becomes a 200 mV differential signal as it traverses through the EP system, which can make the signal move out of the display range of most conventional monitoring devices. Such 200 mV signals should generally be removed so that the signals can be viewed in an EP environment.

Figure 12:
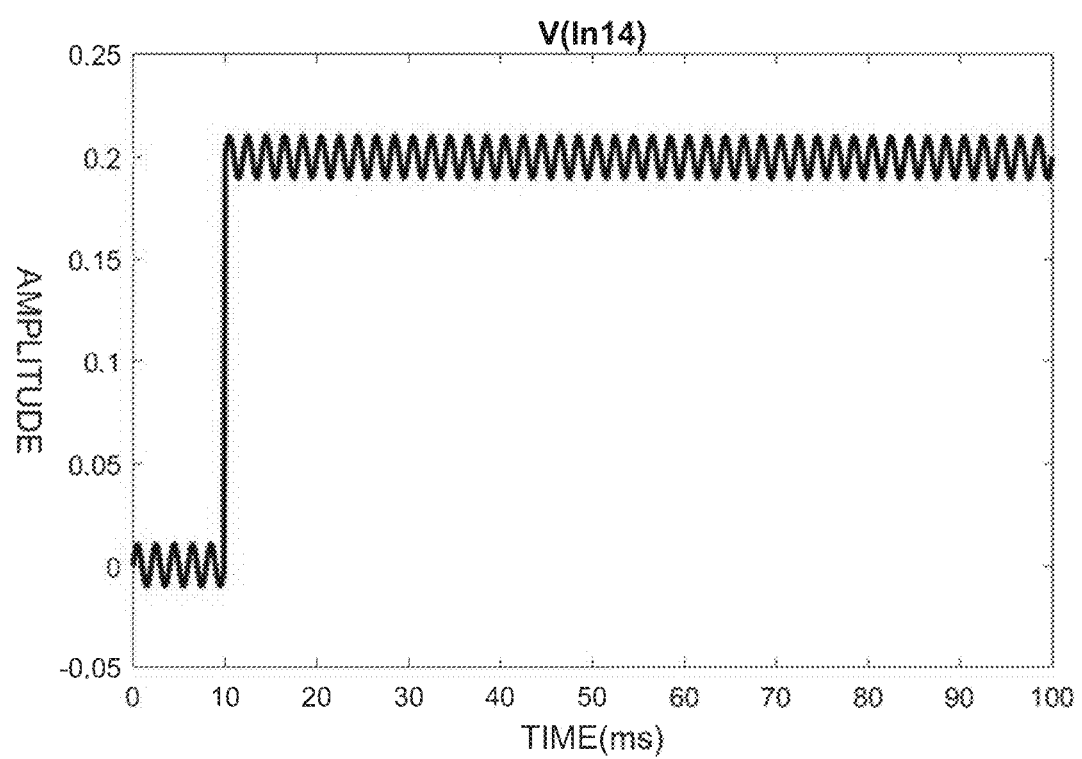
FIG. 12 illustrates a voltage signal plot showing the slow recovery that occurs after a large unwanted signal survives the input protection, instrumentation, and gain stages of the EP hardware system circuitry when the large-signal detection/fast recovery circuit is disconnected, according to an exemplary embodiment.

FIG. 12 illustrates what happens to such an input signal if the large-signal detection/fast recovery circuit 1100 is not connected. After the sample input 20 mVpp signal with an unwanted 200 mV step-up gets through the analog input protection/filtering stage 530, instrumentation amplifier 1001, and differential amplifier #1 1017 to reach the large-signal detection/fast recovery circuit 1100, if the large-signal detection/fast recovery circuit 1100 is not connected, the EP hardware system cannot recover quickly from the 200 mV step signal. Such slow recovery complicates the identification of cardiac signals.

Resistors 1002 and 1004, located before the instrumentation amplifier 1001 of FIG. 10, pull the offset signals back to a ground level eventually, but a time constant of about 2.7 seconds is produced by the product of the DC blocking capacitor (not shown) of Block 4 and resistor 1002. This introduced delay is too long to recover an off-screen or saturated signal. FIG. 12 illustrates that the signal on the input node In14 moves down inappreciably in about 100 msec and only a few millivolts in about 400 msec (not shown). Such a large-transient signal will likely have an adverse impact on the operation of the EP system without the large-signal detection/fast recovery circuit 1100, because the large transient would push the monitored signal to saturation and the waveform details of the signal would be lost.

Figure 13A:
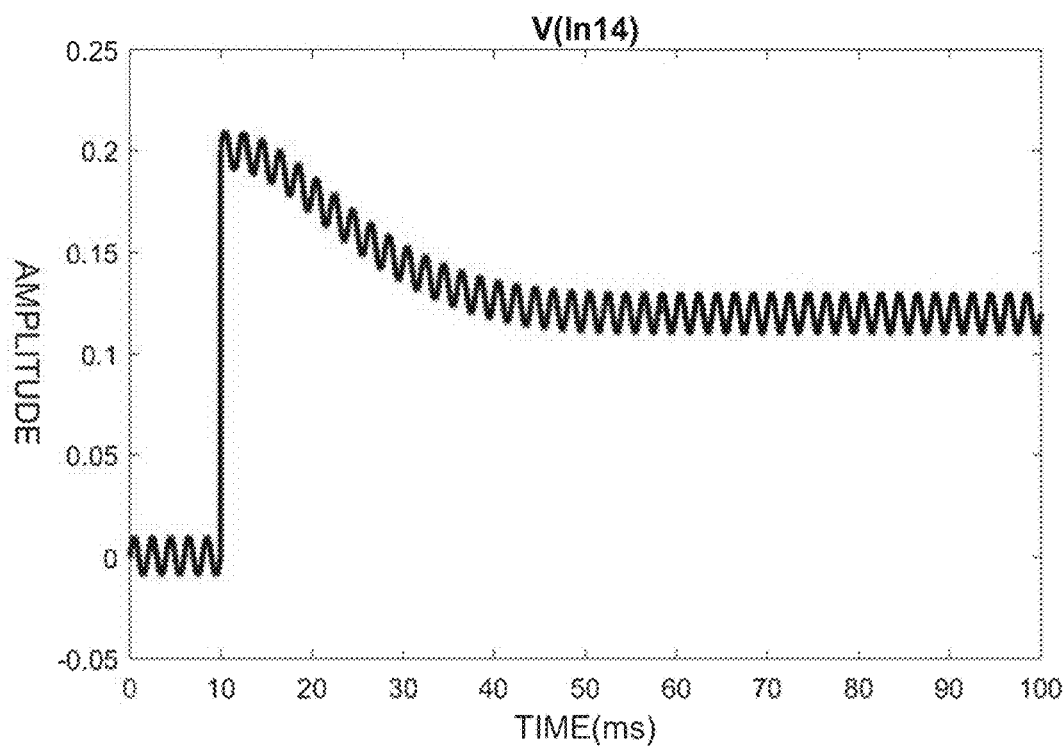
FIGS. 13A-13C illustrate voltage signal plots showing the fast recovery that occurs after a large unwanted signal is presented to the input protection, instrumentation, and gain stages of the EP hardware system circuitry when the large-signal detection/fast recovery circuit is connected, according to an exemplary embodiment.
Figure 13B:
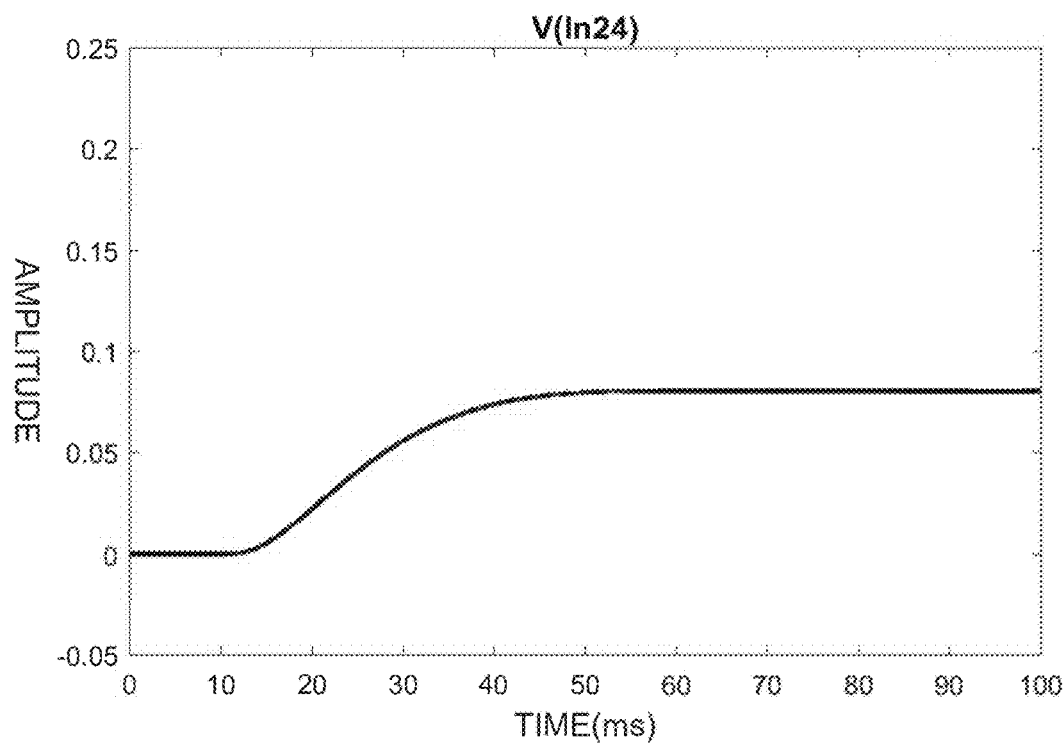
Figure 13C:
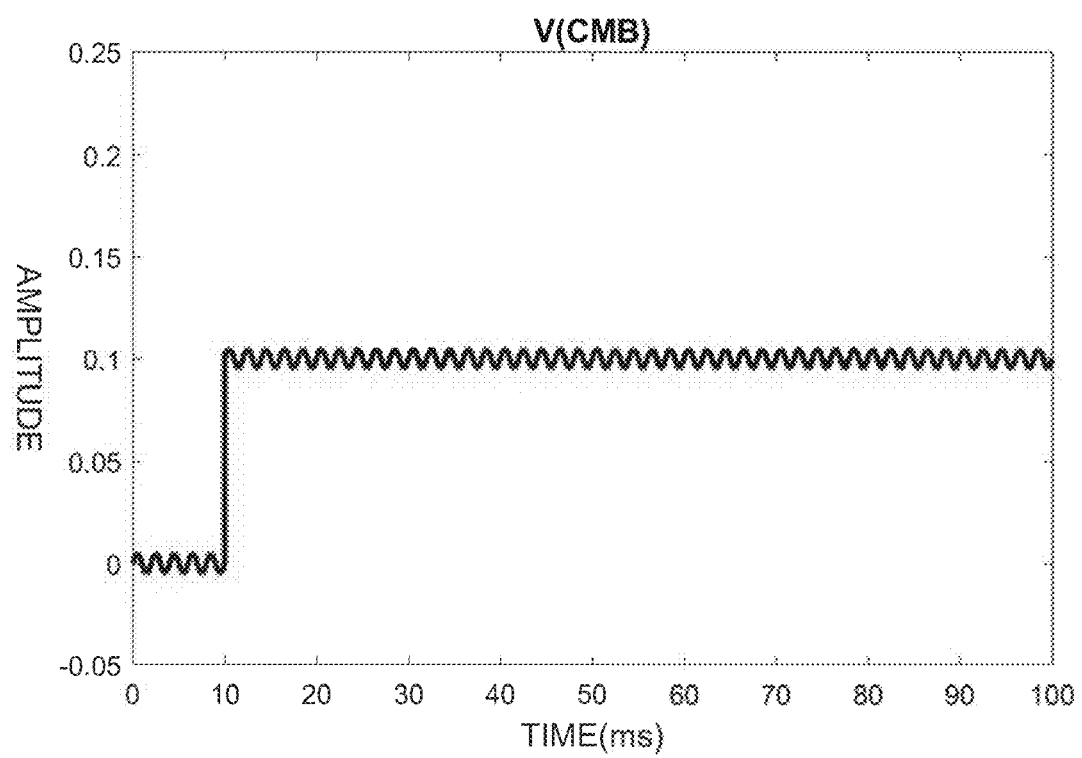

FIGS. 13A-13C illustrate the same 200 mV large-transient signal when using a connected large-signal detection/fast recovery circuit 1100. In this example, as shown in FIGS. 13A and 13B, both input nodes of the large-signal detection/fast recovery circuit 1100, In14 and In24 (shown in FIG. 11), are pulled (biased) toward the common mode signal V(CMB), which is at an amplitude of about 100 mV (see FIG. 13C). In14, the positive input node of the large-signal detection/fast recovery circuit 1100, is pulled down, and In24, the negative input node of the large-signal detection/fast recovery circuit 1100, is pulled up. V(CMB) is the average of the voltage at nodes In14 and In22 (the symmetric negative input to the overall circuit). The actual common mode level of nodes In14 and In24 has no impact because the desired bias level is applied directly to the differential amplifiers of Blocks 6 and 7 (1020 and 1034, respectively), which sets the common mode voltage at those differential amplifiers 1020, 1034.

The plots in FIGS. 13A and 13B illustrate that the voltages of nodes In14 and In24 are pulled into monitoring range after about 50 milliseconds. The limiting, or "soft clamping," is thus performed gradually to avoid discontinuity in the signal acquisition and visualization. Other embodiments may allow for a gradual "clamping" in about 100 milliseconds.

Figure 14A:
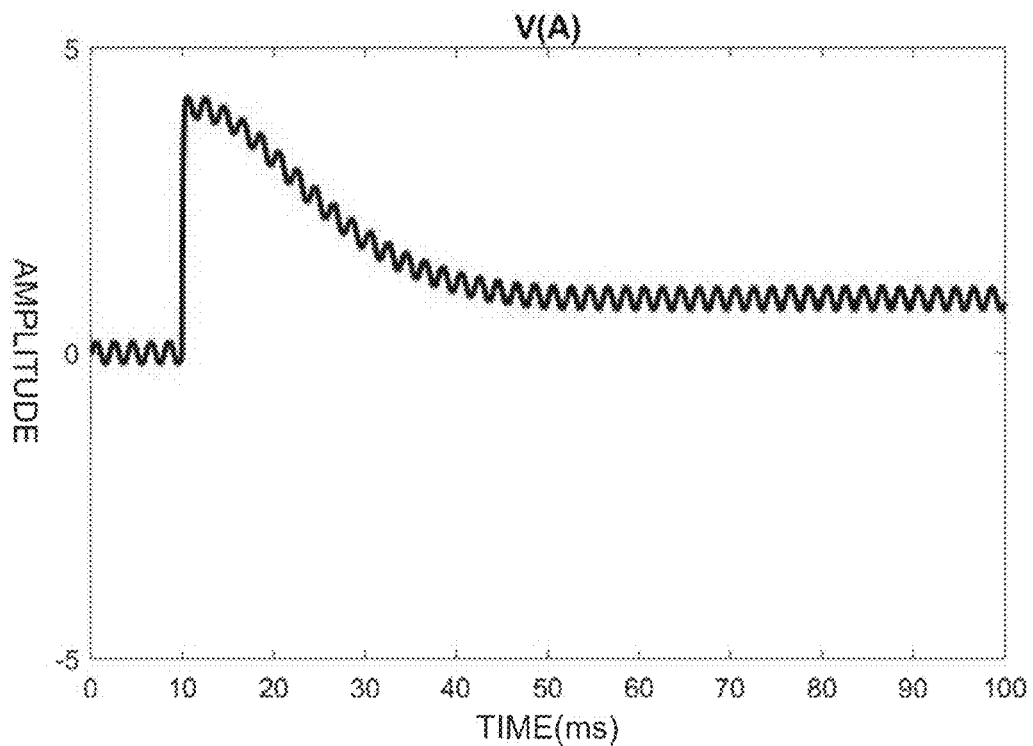
FIGS. 14A-14D illustrate signal plots for voltage signals at various internal nodes through the large-signal detection/fast recovery circuit when it is connected, according to an exemplary embodiment.
Figure 14B:
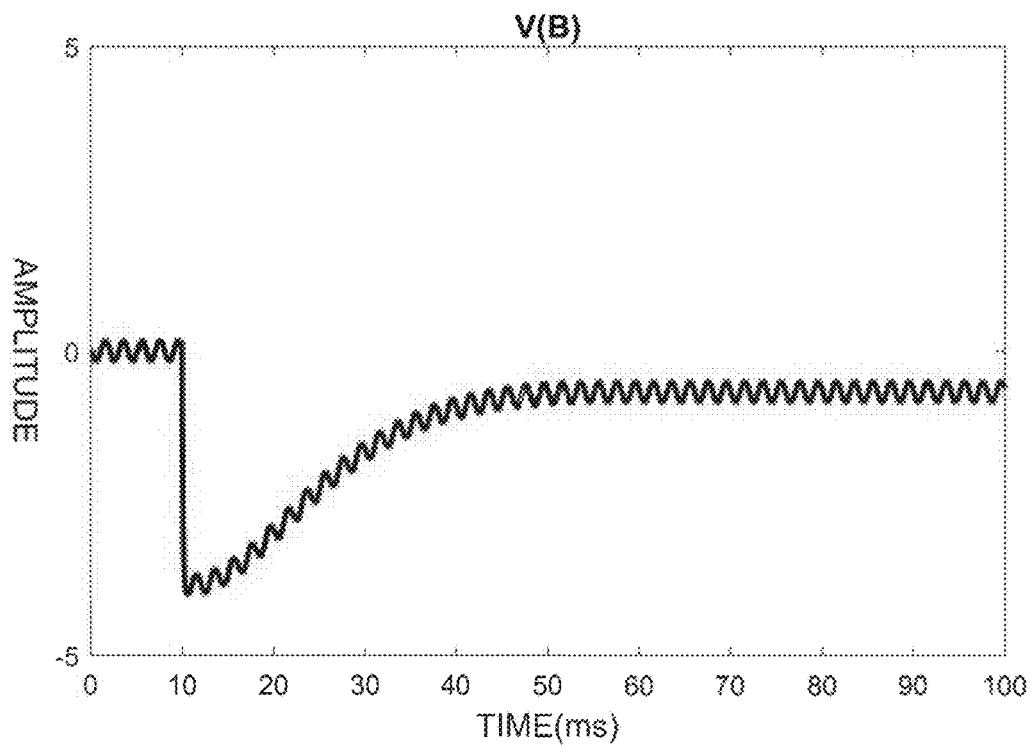

FIGS. 14A-14D demonstrate how a large-transient signal is conditioned as it traverses the various internal nodes of the large-signal detection/fast recovery circuit 1100. Signal plots V(A) of FIG. 14A and V(B) of FIG. 14B represent the outputs of the operational amplifier 1108 of the large-signal detection/fast recovery circuit 1100 in FIG. 11. In this example, operational amplifier 1108 has a gain of about 40, relative to the input, and produces a (40×200 mV=) 8-volt differential signal across nodes A and B in FIG. 11.

Figure 14C:
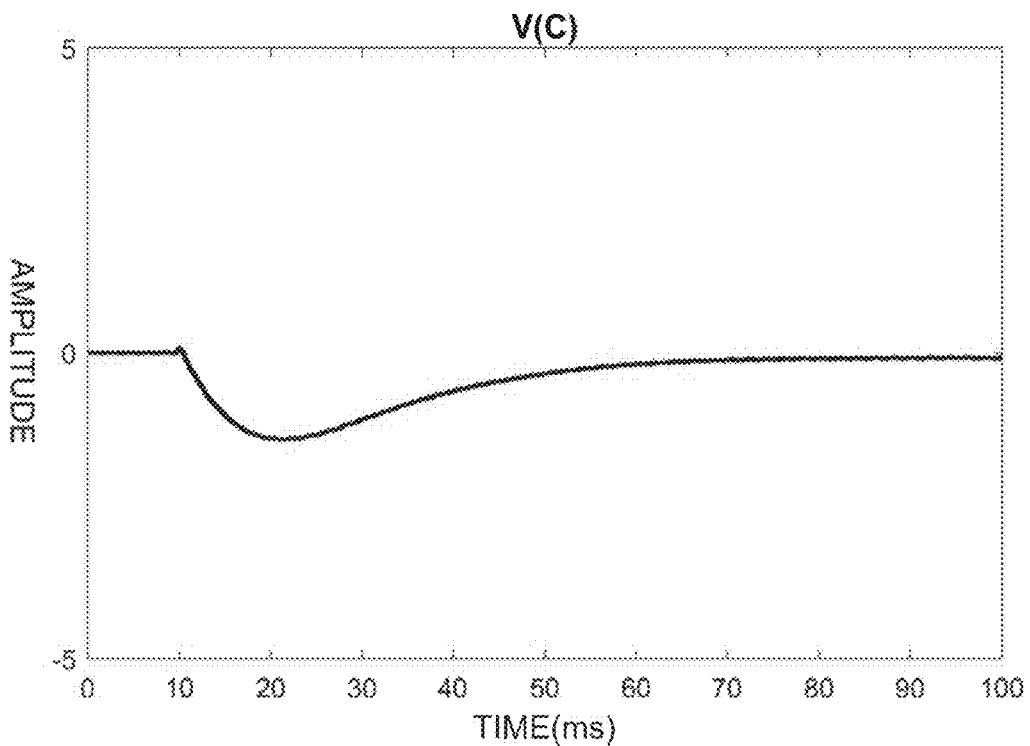
Figure 14D:
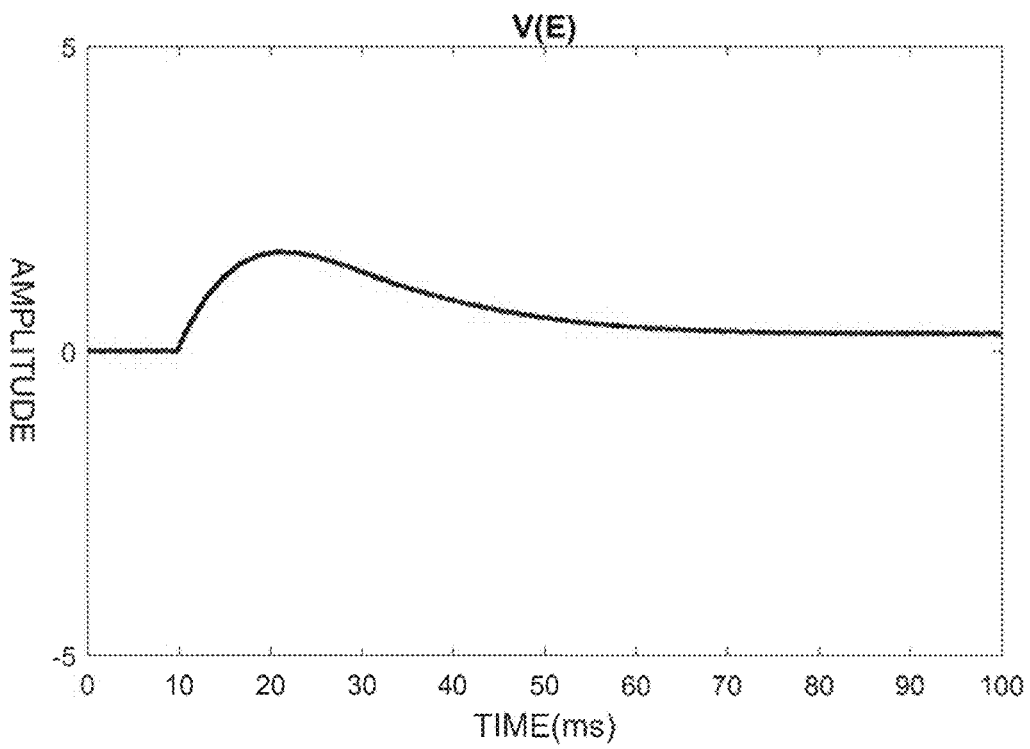

As shown in plot V(C) of FIG. 14C, following node B of FIG. 11, the negative signal pulls down the voltage at node C of FIG. 11. Here, the signal has been filtered to remove the in-band signal that occurs at node B, leaving a low-frequency control voltage at node C. The negative voltage at node C is connected to In14 through resistor 1140, diode 1150, and resistor 1144. This produces a current that pulls In14 down toward the common mode voltage, such as illustrated in FIG. 13A. Similarly, as shown in plot V(E) of FIG. 14D, node A pulls up In24 toward the common mode voltage through node E and J of FIG. 11.

The diodes in the large-signal detection/fast recovery circuit 1100 of FIG. 11 control the direction of current flow. The first pair of diode stages 1114, 1116 (limiting diodes) allows different time constants for charging and discharging nodes C, D, E, and F. They also provide a non-operating range where the nodes C, D, E, and F are not charged when the outputs A and B are less than the diode forward voltage drop. The "clamping" diodes 1150, 1152, 1154, 1156 of the second pair of diode stages 1146, 1148 ensure that input nodes In14 and In24 are pulled in the correct direction.

Figure 15A:
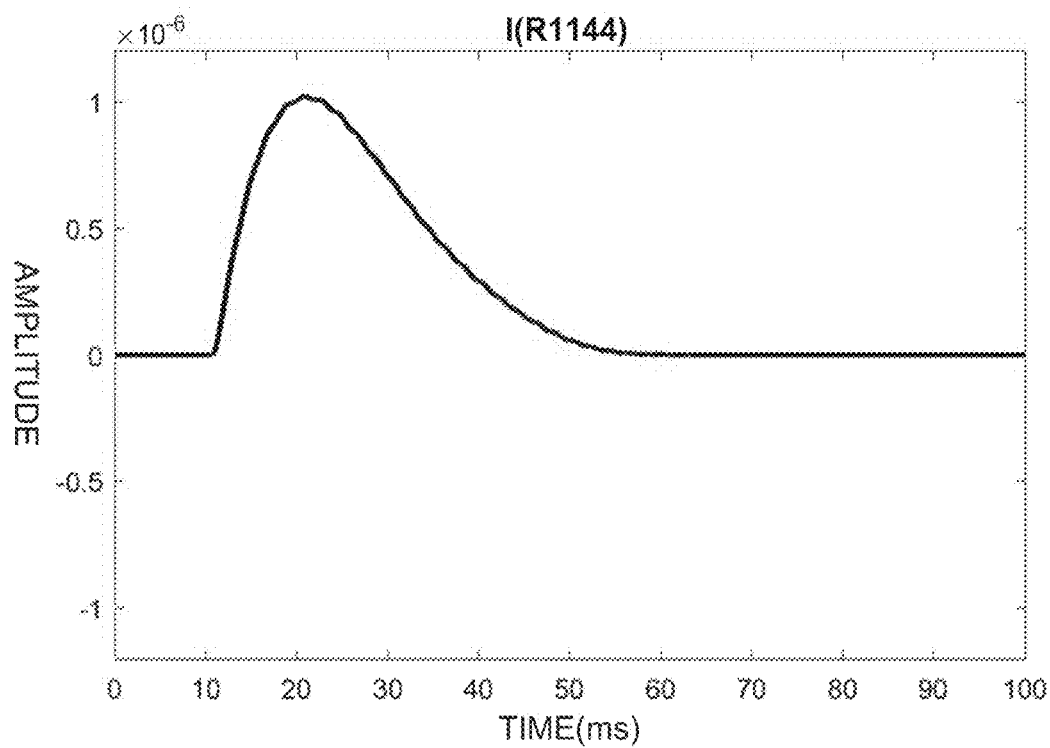
FIGS. 15A-15B illustrate signal plots for current signals over the resistors at the output of the connected large-signal detection/fast recovery circuit, according to an exemplary embodiment.
Figure 15B:
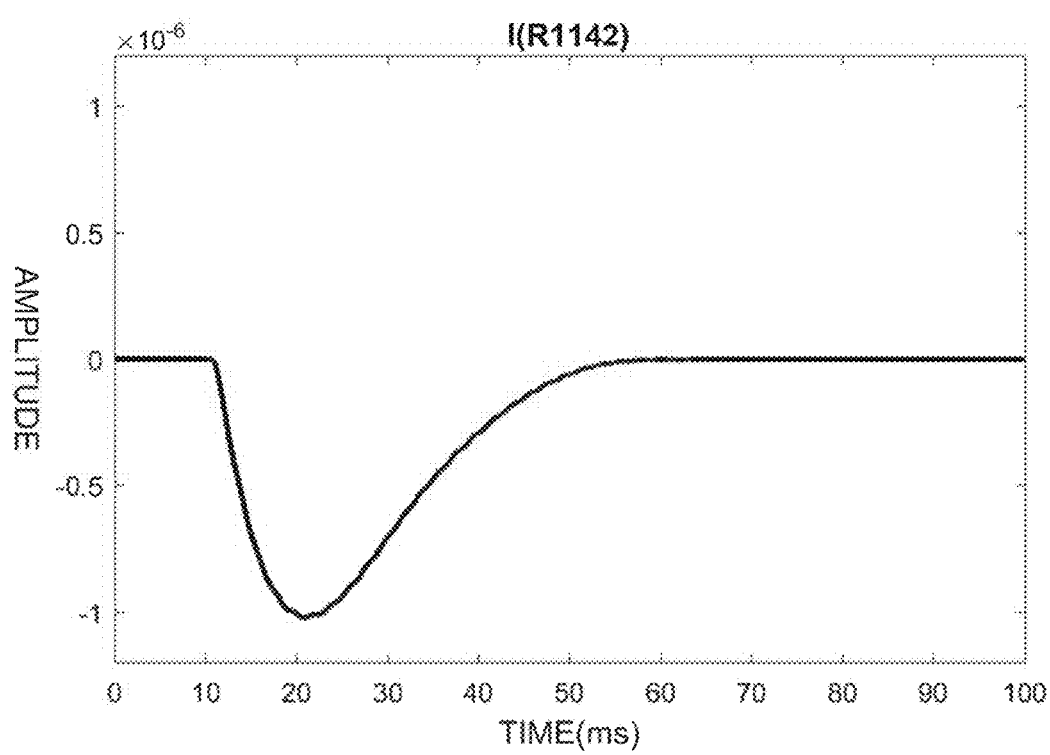
Figure 16:
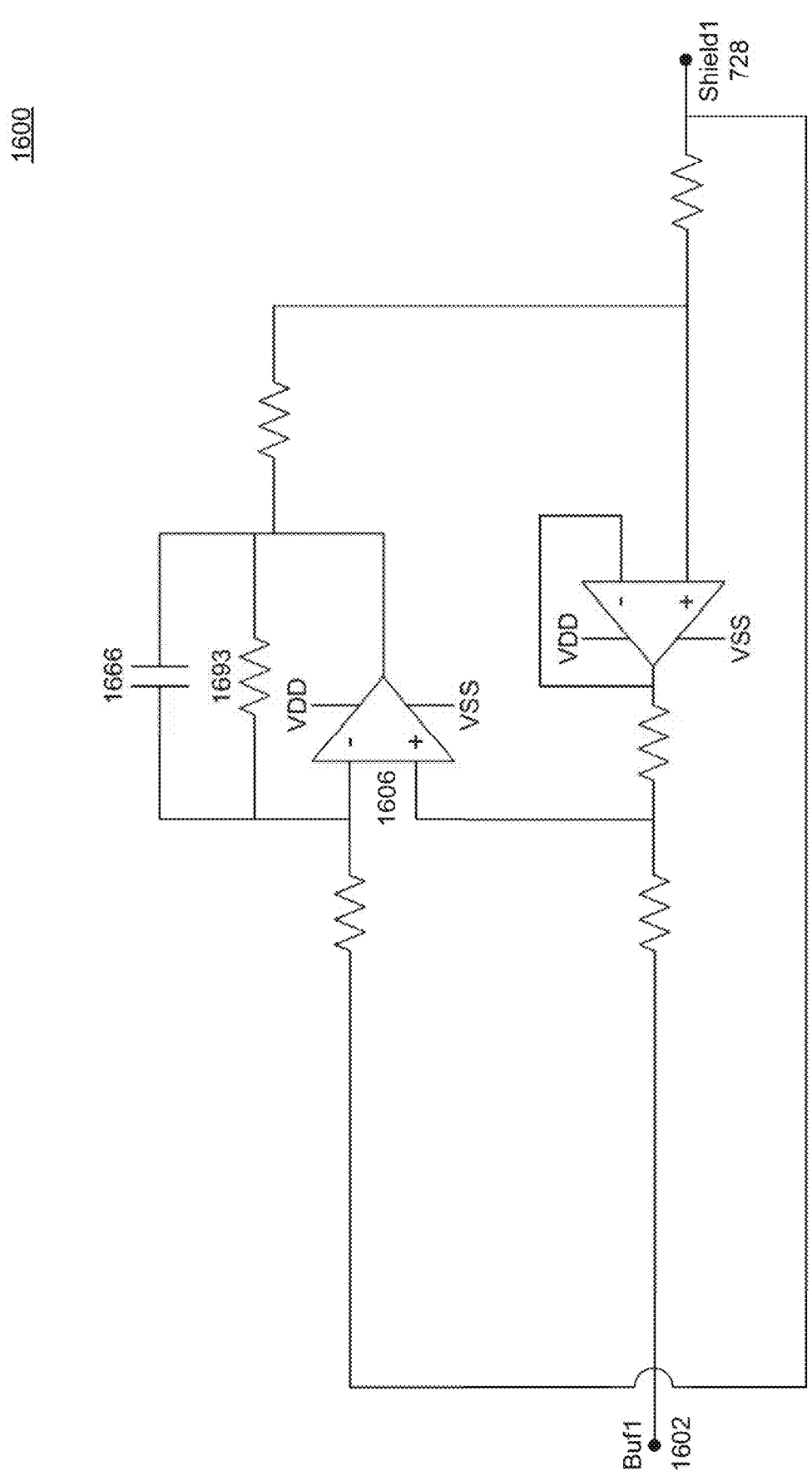
FIG. 16 illustrates a schematic diagram of a low-frequency feedback circuit that serves as a dynamic current source for the EP hardware system, according to some embodiments.

FIGS. 15A-15B show signal plots of the current through the resistors 1144, 1142 at the outputs In14 and In24, respectively, of the large-signal detection/fast recovery circuit 1100 of FIG. 11. During normal operation, the current is 0 and the instrumentation amplifier/filter 410 circuit is unaffected. When the differential level is too high (that is, when a large signal is detected, for example, in excess of 100 mV over several milliseconds), the current in those two resistors 1144, 1142 help pull the signals back toward the common mode voltage, V(CMB).

A/D Converter

The A/D Converter 416, Block 8 (see FIG. 4), is a fully differential A/D converter that is designed to accept differential signals from the rest of the circuit. In some embodiments, each of the EP system circuit modules is duplicated eight times so to feed as differential pairs into the eight separate channels of the A/D Converter 416. A TI ADS1278 24-bit, 8-channel delta-sigma converter can be used, for example. A person of ordinary skill in the art may choose other A/D converters of similar specifications.

In some embodiments, the A/D converter 416 is highly linear, a characteristic of delta-sigma converters. The high linearity allows accurate digital signal processing to be performed in the software, as described below. This configuration minimizes hardware filtering to that advantageous for RF attenuation and anti-aliasing, and allows more flexibility of filtering and signal processing in software. The advantage of choosing a fully differential A/D converter is that common mode noise signals from any digital circuitry (e.g., a digital clock signal) are rejected.

Wilson Central Terminal-Right Leg Drive (WCT-RLD) Circuit

Although input common mode signals can be at any frequency, the dominant signals are generally at the power line frequency: 60 Hz in the U.S., for example. In a conventional EP environment, ECG (and similar) equipment mitigates a large amount of 60 Hz noise that could be up to 100 times larger than the signal of interest. In addition, because of distortions in the power line signal, there is often a strong third harmonic at 180 Hz, which is generally the noisiest harmonic. Higher harmonics and other common mode signals are generally smaller and/or are above the frequency band of interest for the ECG and IC signals.

Figure 23:
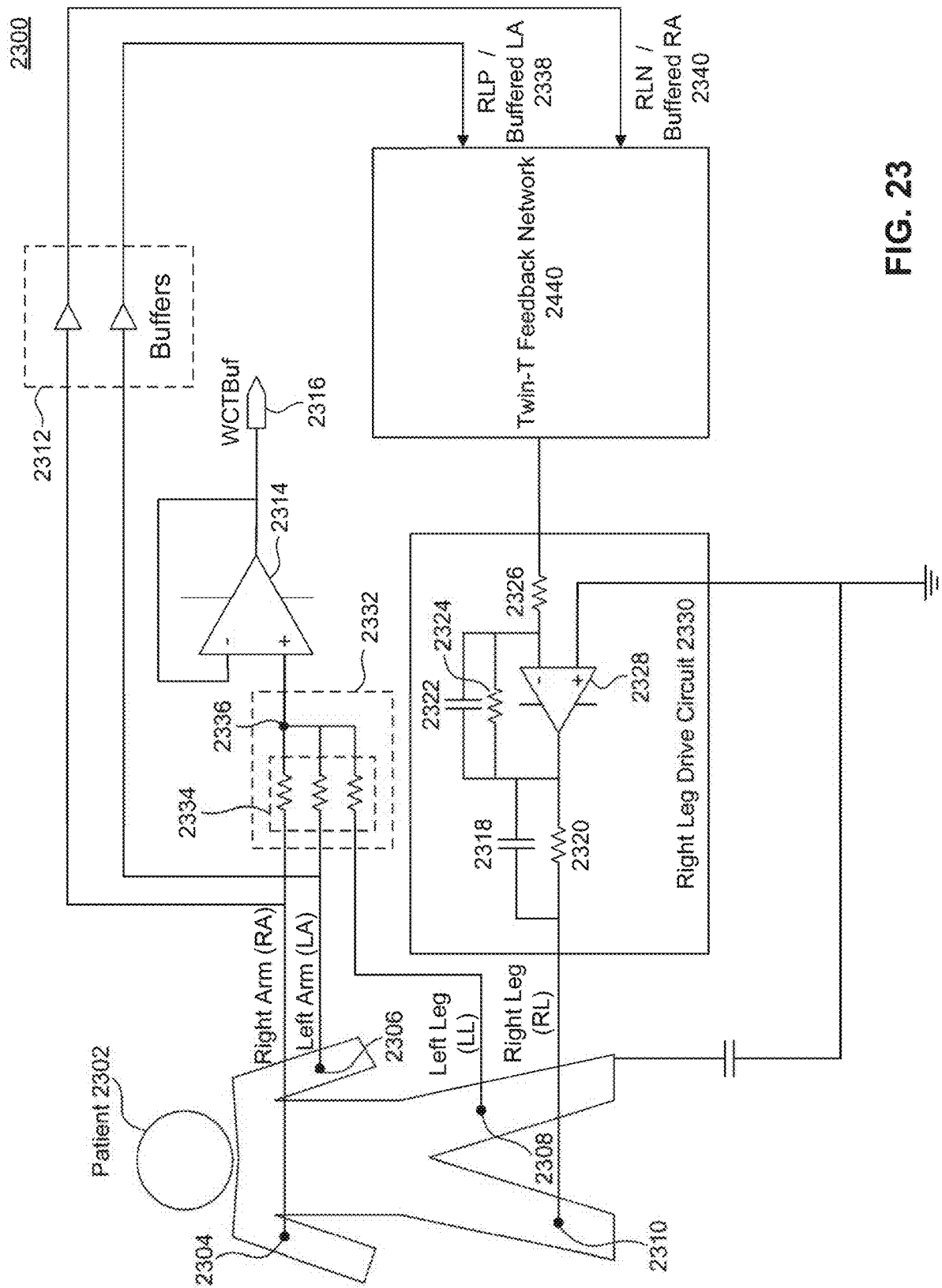
FIG. 23 illustrates a schematic diagram of an improved Wilson Central Terminal-Right Leg Drive (WCT-RLD) circuit, according to some embodiments.

In some embodiments, a Wilson Central Terminal-Right Leg Drive (WCT-RLD) circuit is used to remove particularly the 60 Hz and 180 Hz noise by common mode rejection, that is, by enhancing the first and third harmonic frequencies of the power line signals and selectively feeding those signals back to the patient to cancel them out. FIG. 23 illustrates a schematic diagram of an improved WCT-RLD circuit, according to some embodiments.

For example, a WCT circuit 2332 of FIG. 23 provides a virtual ground by summing and averaging two or three limb electrodes (e.g., right arm 2304 and left arm 2306, or the right arm 2304, left arm 2306, and left leg 2308) connected to a central terminal 2336 through two or three large resistors 2334 (e.g., 20 kOhms on each electrode). A person of ordinary skill in the art will understand that the average of the right arm (RA) 2304, left arm (LA) 2306, and left leg 2308 provides a more accurate estimate of the common mode signal on the patient 2302 than does the average of the right arm (RA) 2304 and left arm (LA) 2306. As also understood by a person of ordinary skill in the art, the RA and LA signals are alternatively buffered (see buffer 2312) versions of the RL positive (RLP) 2338 and RL negative (RLN) 2340 signals. A WCT is conventionally designed to reduce the overall 60 Hz common mode noise signal by bringing the net potential difference of these limb leads close to zero.

The addition of an active current via the right leg, the "right leg drive" (RLD) circuit 2330, to the WCT circuit 2332 allows the patient to be driven to the same voltage as the common amplifier, thus reducing the common mode voltage at the inputs of the ECG electrodes (LA, RA, LL, and V1 to V6). This can be done by generating the inverse of the common mode signal and applying that as an output to the right leg. Specifically, the right leg drive is represented by limb electrode RL. The patient 2302 receives, through the RL electrode, an RLD output 2310, a summed and inverted version of the other IC catheter signals or ECG electrode signals, canceling interference present in the patient's body. This, in combination with the common mode rejection properties of the signal amplification stage 532, can reduce common mode low-frequency interference to acceptable levels (specified by standard IEC 60601-2-25, for example).

However, because 60 Hz and 180 Hz noise is not equal in all parts of the body, common mode rejection alone cannot remove all of the noise. The WCT-RLD circuit 2300 of FIG. 23 provides a reference signal, approximately equal to the line frequency coming into the system, which further reduces the overall common mode signal. Thus, the combination of the disclosed WCT-RLD circuit 2300 and conventional common mode rejection provides an advantageous improvement in the reduction of the common mode signal.

In an exemplary embodiment using the WCT, the WCT input within the EP system can provide an optional unipolar input to replace the bipolar positive (+) or negative (−) catheter input to the Block 3 Buffer circuit (see FIGS. 4, 406a and 406b). Specifically, the WCT-RLD circuit 2300 averages the right arm 2304, left arm 2306, and left leg 2308 electrode signals. The result is buffered by the operational amplifier 2314, and the output WCTBuf 2316 is sent as a unipolar feedback signal wherever it is desired in the EP system, specifically used in embodiments whenever a patient is connected. The WCT-RLD disclosed herein enhances a conventional unipolar WCT solution with a novel approach for generating an RLD signal.

In some embodiments, a novel approach in the WCT-RLD circuit 2300 is to provide additional filter circuitry, called a "Twin-T" feedback network 2440 (see FIGS. 23 and 24), which can produce a stronger RLD at the 60 Hz power line frequency or at the 180 Hz third harmonic frequency. This is specifically helpful during ablation. The Twin-T feedback network 2440 resonates at both 60 Hz and 180 Hz, but advantageously prevents phase oscillations by reducing feedback at other frequencies.

Figure 24:
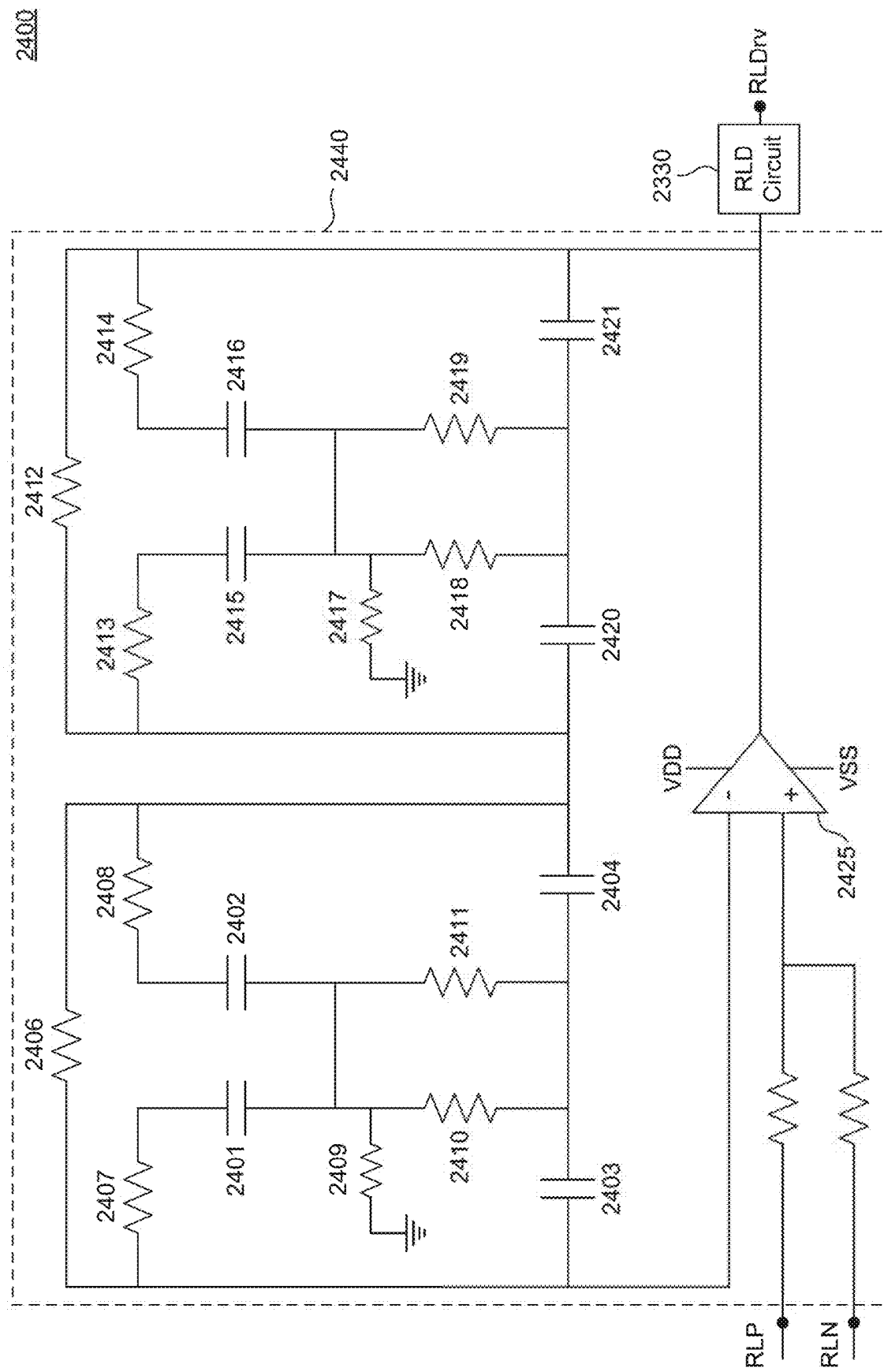
FIG. 24 illustrates a schematic diagram of a Twin-T feedback network interfaced with an RLD circuit of a WCT-RLD circuit, according to some embodiments.

FIG. 24 illustrates a schematic diagram of a Twin-T feedback network 2440 interfaced with the RLD circuit 2330 of the WCT-RLD circuit 2300, according to some embodiments. The Twin-T feedback network 2440 of FIG. 24 serves as an improved notch filter. Resistors 2406, 2407, 2408, 2409, 2410, 2411, and capacitors 2401, 2402, 2403, 2404 form a single Twin-T network that generates a notch at 60 Hz. The next stage, resistors 2412, 2413, 2414, 2417, 2418, 2419, and capacitors 2415, 2416, 2420, 2421, similarly generates a notch at 180 Hz. However, when the network is in an operational amplifier feedback path, the inverse function is obtained.

Figure 25:
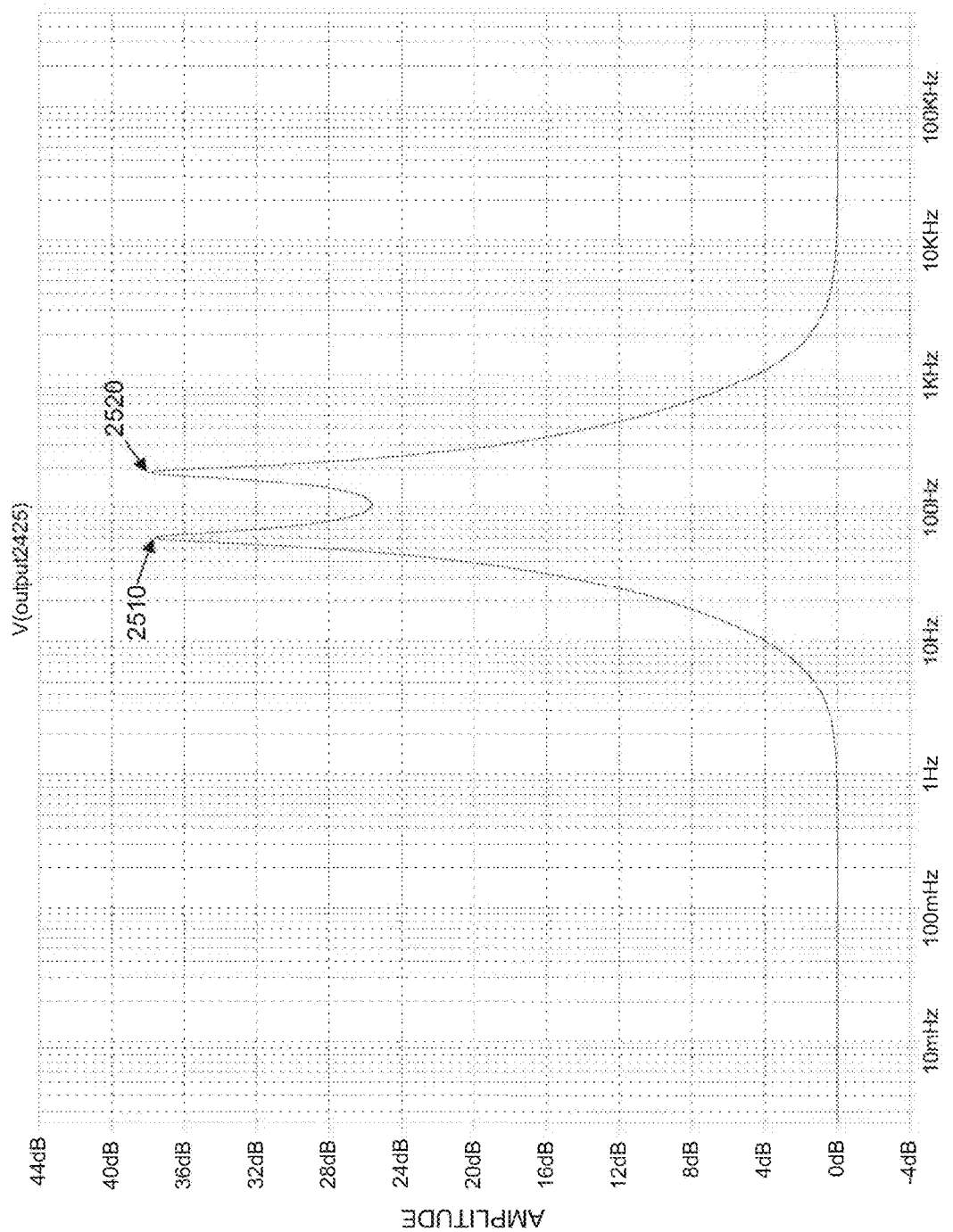
FIG. 25 illustrates a signal plot of the output of a Twin-T feedback network of a WCT-RLD circuit, according to an exemplary embodiment.

For example, as illustrated in the plot 2500 of FIG. 25, the RLD output of the Twin-T feedback network 2440 at operational amplifier 2425 produces two peaks, one at 60 Hz 2510 and one at 180 Hz 2520. At higher frequencies, such as 10 kHz or greater, the phase change goes to zero. This prevents phase changes in the RLD circuit 2330 at these higher frequencies that can cause oscillation. Minimal phase changes at these higher frequencies can prevent oscillations near the ablation frequencies, which would otherwise be more difficult to filter out.

Although Twin-T circuitry is used in electronic design, it has not been previously used in a WCT-RLD circuit as disclosed herein. The Twin-T feedback network 2440 removes power line signals conventionally passed by known circuits when generating a RLD signal, such that the power line signals do not affect phase response at higher frequencies. The Twin-T feedback network 2440 thus has an advantageous use for generating a RLD signal from electrode leads.

In the embodiment of FIG. 23, the RLD circuit 2330 follows the power line by feeding the RLD output 2310 as a separate signal back into the patient 2302. In the circuit, the right leg positive (+) (RLP) 2338 and right leg negative (−) (RLN) 2340 differential input signals, which can alternatively be the RA and LA signals, are buffered 2312. Then, the Twin-T feedback network 2440 emphasizes/amplifies the buffered right leg signal at 60 Hz and 180 Hz, which is inverted and buffered again by the RLD circuit 2330. This RLD circuit 2330 includes an operational amplifier 2328, resistors 2320, 2324, 2326, and capacitors 2318, 2322. After passing through the RLD circuit 2330, the signal is output as the RLD output 2310 (RLDrv) at a surface lead on the patient's right leg. The effect is that the entire circuit tracks the power line, and the common mode of the circuit rejects the power line noise. Additionally, the circuit of the right leg drive protects against any signal going back into the patient that is greater than approximately one (1) microampere.

The following cases illustrate how the disclosed hardware circuitry conditions signals found in an EP environment, allowing improved cardiac monitoring in the midst of equipment and environment noise, and during procedures that introduce large, potentially interfering signals into the monitoring environment.

Signal Case #1—Common Mode 60 Hz and in-Band 500 Hz Differential Signal

Signal case #1 presents a typical common mode 60 Hz noise signal with an in-band (less than 1000 Hz) differential signal as found from conventional IC leads. In this example, a series of signal plots representing the signal at exemplary nodes of the disclosed circuit is shown. The circuit amplifies the differential signal and rejects the common mode signal.

Figure 17A:
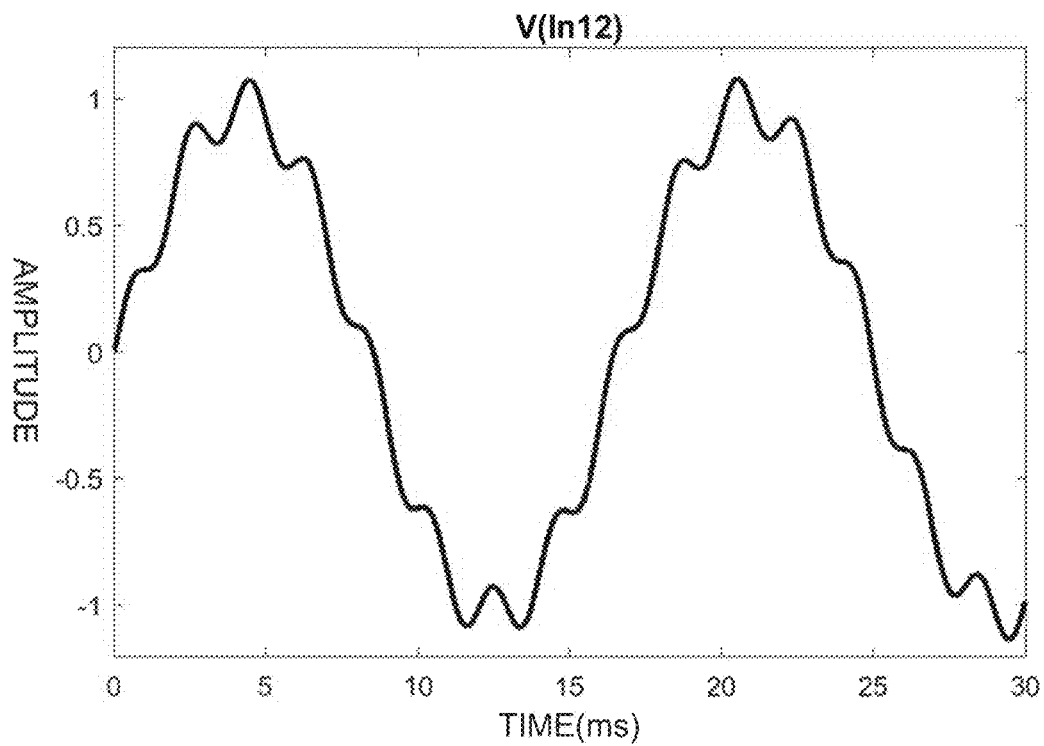
FIGS. 17A-17D illustrate signal plots for typical in-band voltage differential input signals that are affected by 60 Hz common-mode noise into the EP hardware system, according to an exemplary embodiment.
Figure 17B:
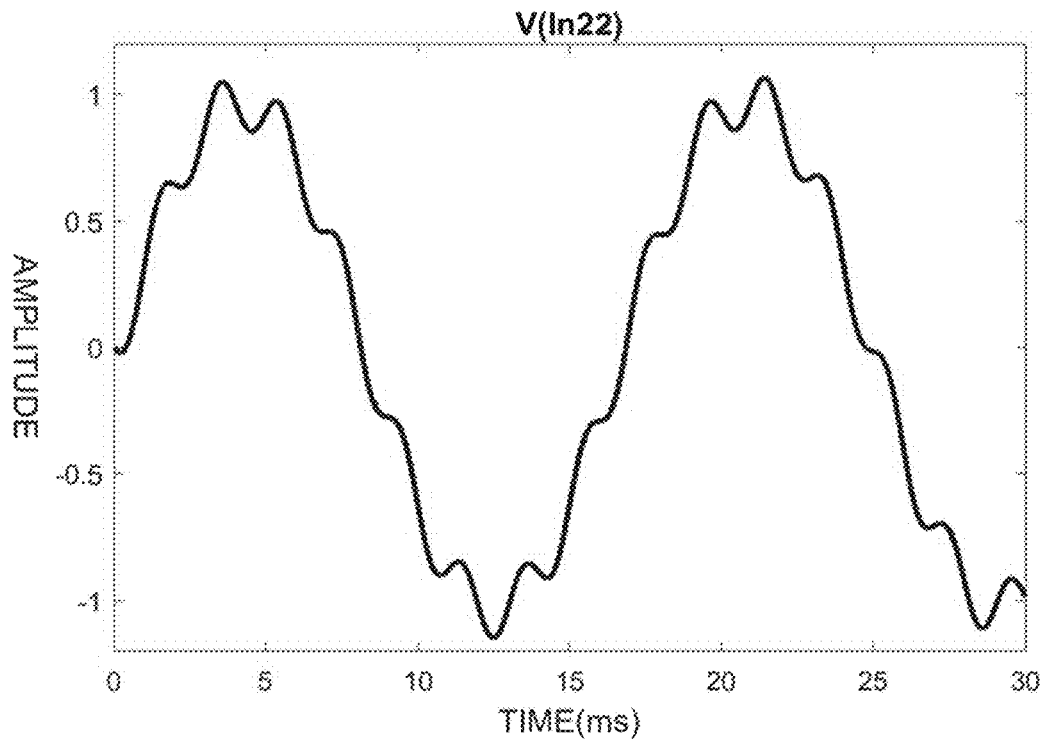

FIGS. 17A-17B illustrate an input signal of 2 Vpp 60 Hz sine (power line) signal applied to input nodes In12 (see FIG. 6A) and In22 (the negative, lower branch of the circuit, not shown), respectively. Superimposed on In12 is a 0.2 Vpp, 500 Hz sine wave signal (see plot V(In12) of FIG. 17A) and on In22 is a −0.2 V, 500 Hz sine wave signal (see plot V(In22) of FIG. 17B). This results in a 2 Vpp, 60 Hz common mode signal and a 0.4 V, 500 Hz differential signal. These signals may be too low in frequency to be affected by the RF filter 702 of Block 2, so the same signals appear at the output of Block 3 (Buffer 406a, 406b) and after Block 4 (DC Block 408a, 408b).

Figure 17C:
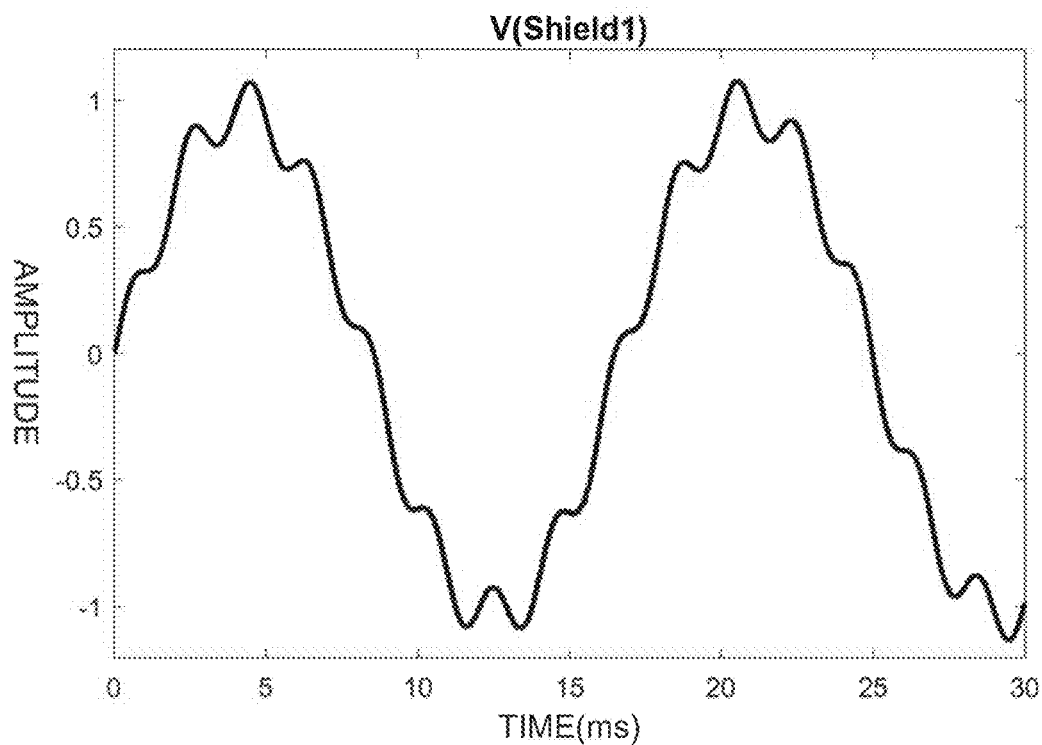
Figure 17D:
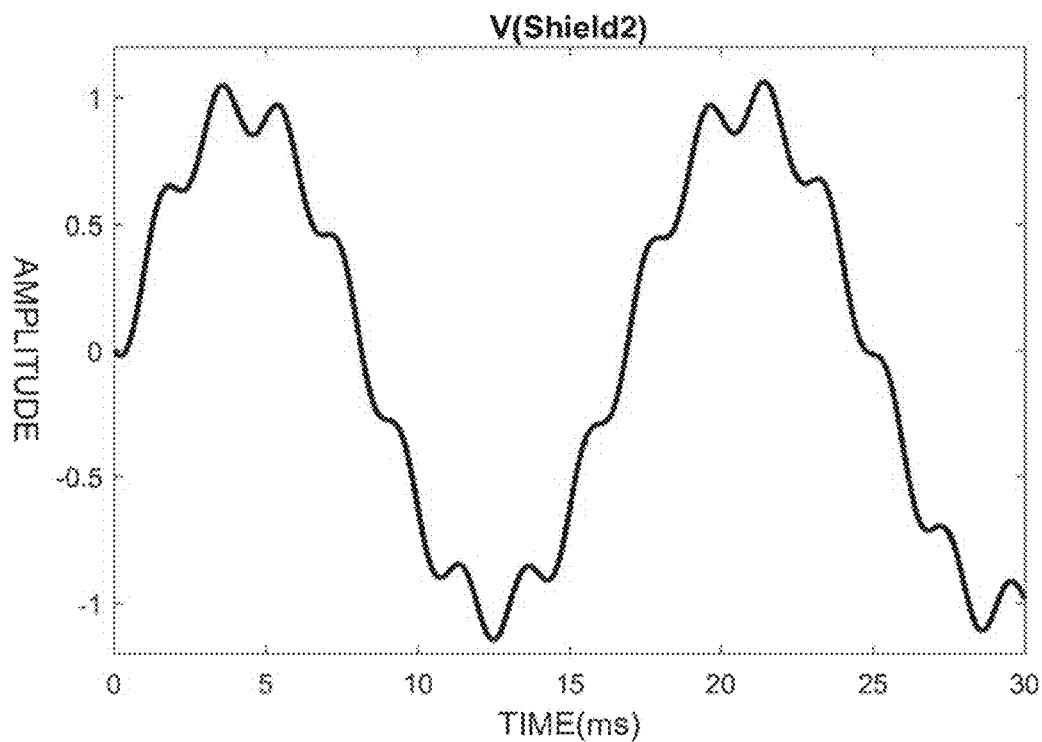

FIGS. 17C-17D illustrate shield input signals (Shield1, Shield2) that are also the same as the corresponding input signals shown in FIGS. 17A-17B. These signals are fed back from Block 10 (low-frequency feedback circuit 1600) to the RF filter 702 to eliminate loading from the RF filter 702. (See Shield1, 728 of FIG. 7. Shield2, the negative, lower branch of the circuit, is not shown.) The voltage change on capacitors 714, 716, 706 of the upper branch of the RF filter 702 in FIG. 7, as well as on the corresponding capacitors on the symmetrical lower branch of the RF filter (not shown) is close to 0, effectively removing them from the circuit at low frequencies.

Figure 18A:
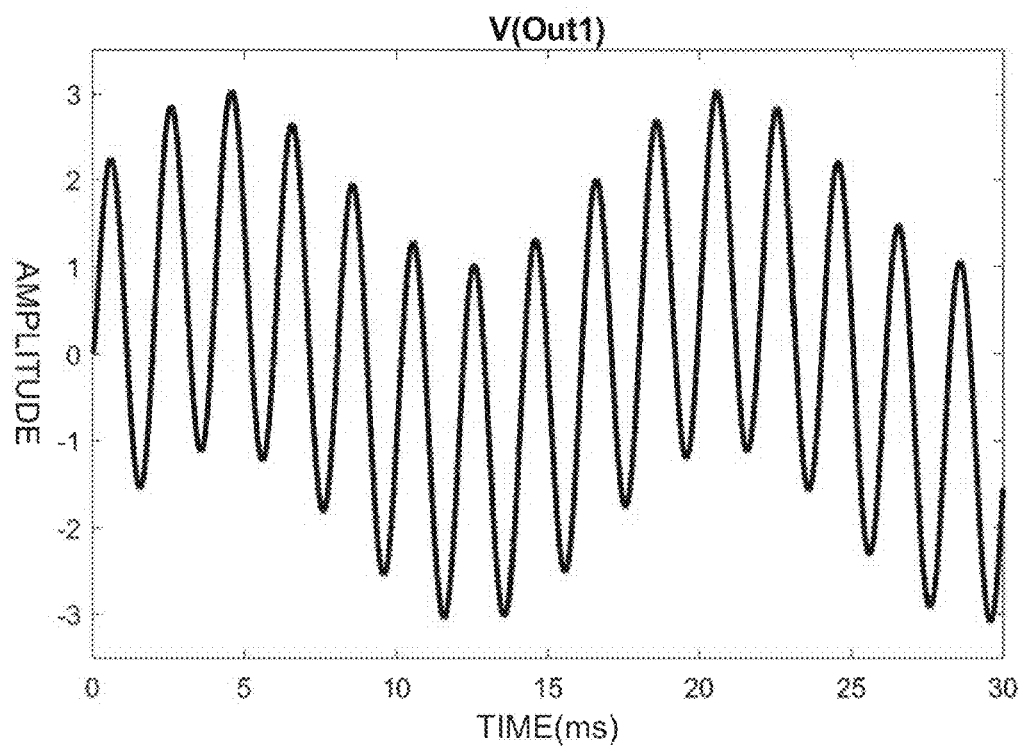
FIGS. 18A-D illustrate signal plots of a typical differential voltage signal affected by 60 Hz common-mode noise as it travels through the EP hardware system, according to an exemplary embodiment.
Figure 18B:
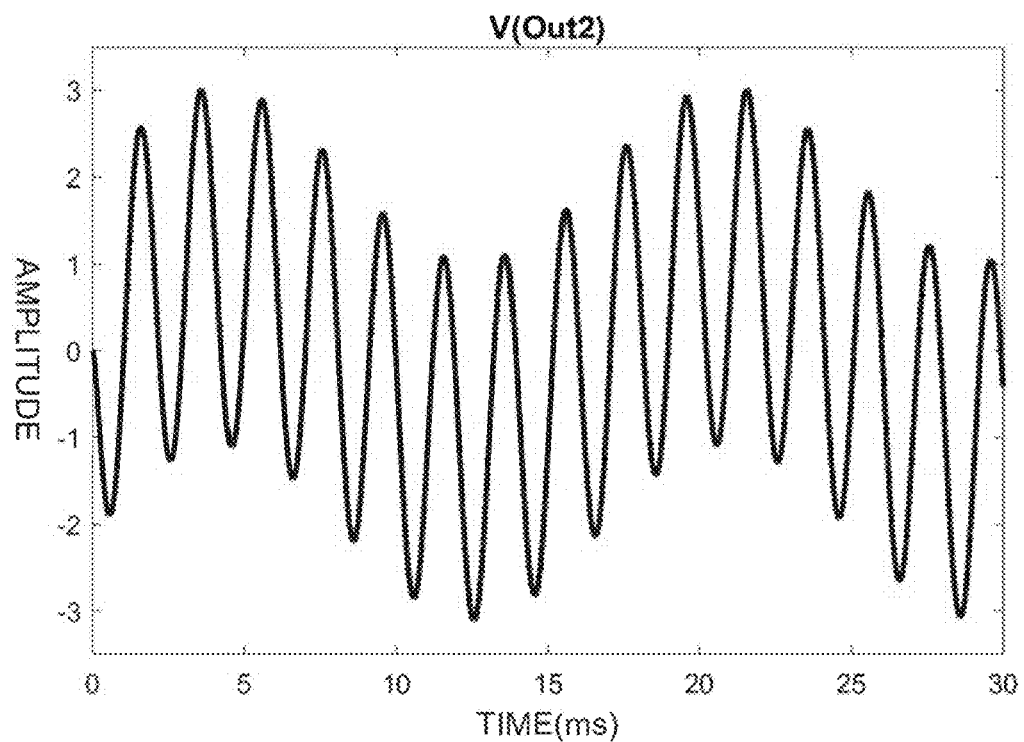

FIGS. 18A-18B illustrate Out1 and Out2, the outputs of Block 5 (instrumentation amplifier 1001 of FIG. 10) with a differential gain of 20. The common mode signal has a gain of 1 and the differential signals have a gain of 20. The signal at this point becomes a 2 Vpp, 60 Hz sine wave at each output with a superimposed 4 Vpp, 500 Hz signal at Out1 (see FIG. 18A) and a −4 Vpp, 500 Hz signal at Out2 (see FIG. 18B), creating a 8 Vpp differential signal.

Figure 18C:
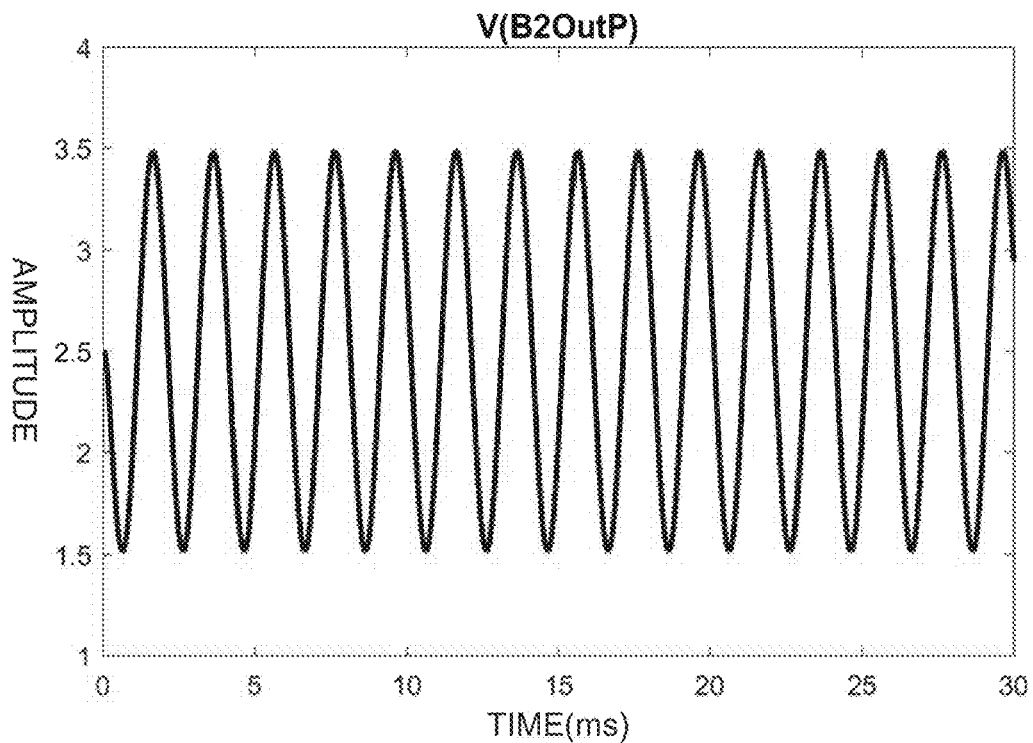
Figure 18D:
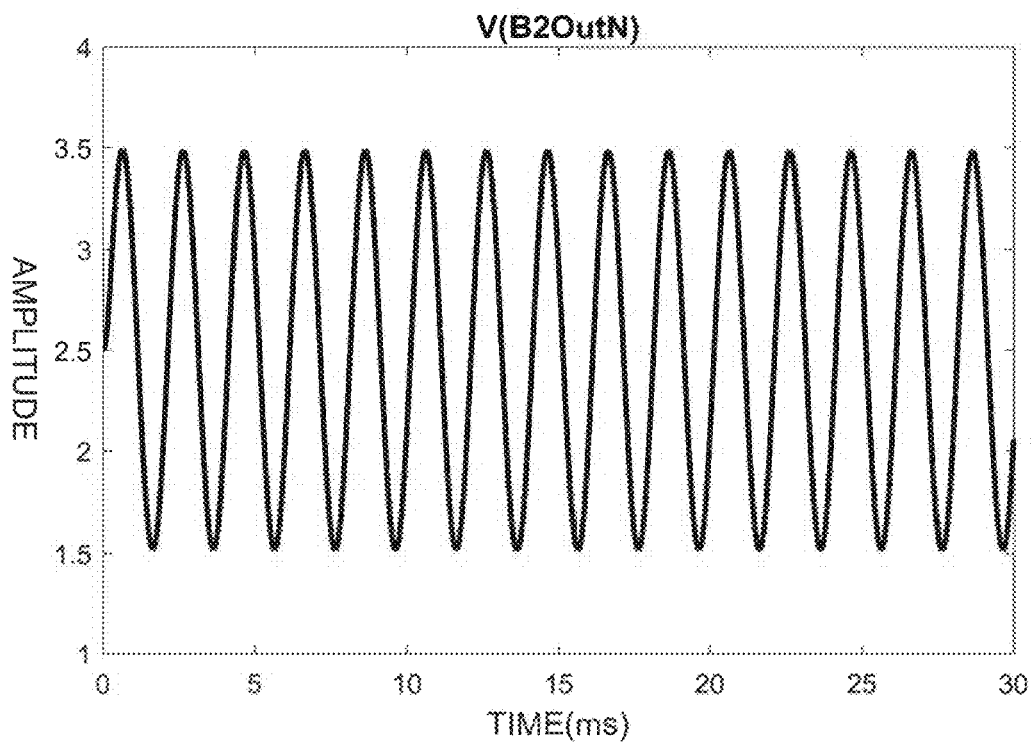

FIGS. 18C-18D illustrate the outputs B2OutP and B2OutN of FIG. 10, respectively. At B2OutP and B2OutN, the signals have passed through the fully differential operational amplifiers (Blocks 6 and 7, 1017, 1021) of FIG. 10, have eliminated the common mode signal, and have referred the outputs to the common-mode output voltage, VOCM (2.5V bias level). The gain of 0.5 at amplifier 1034 of Block 7 results in a final set of 500 Hz signals of 2 Vpp at B2OutP (see FIG. 18C) and −2 Vpp at B2OutN (see FIG. 18D), which is equivalent to a 4 Vpp differential 500 Hz signal. From the input to the output, the common mode gain is 0 and the differential gain is 10. The common mode signal can thus be eliminated through the combined responses of the instrumentation amplifier (Block 5) and the fully differential operational amplifiers (Blocks 6 and 7).

Signal Case #2—500 kHz Ablation Signal

Signal case #2 presents a typical 500 kHz ablation signal applied to the EP system inputs during an ablation procedure as cardiac monitoring continues. The unwanted ablation signal is filtered and attenuated before reaching the A/D converter (see FIG. 4, Block 8, 416) of the disclosed circuit.

Figure 19A:
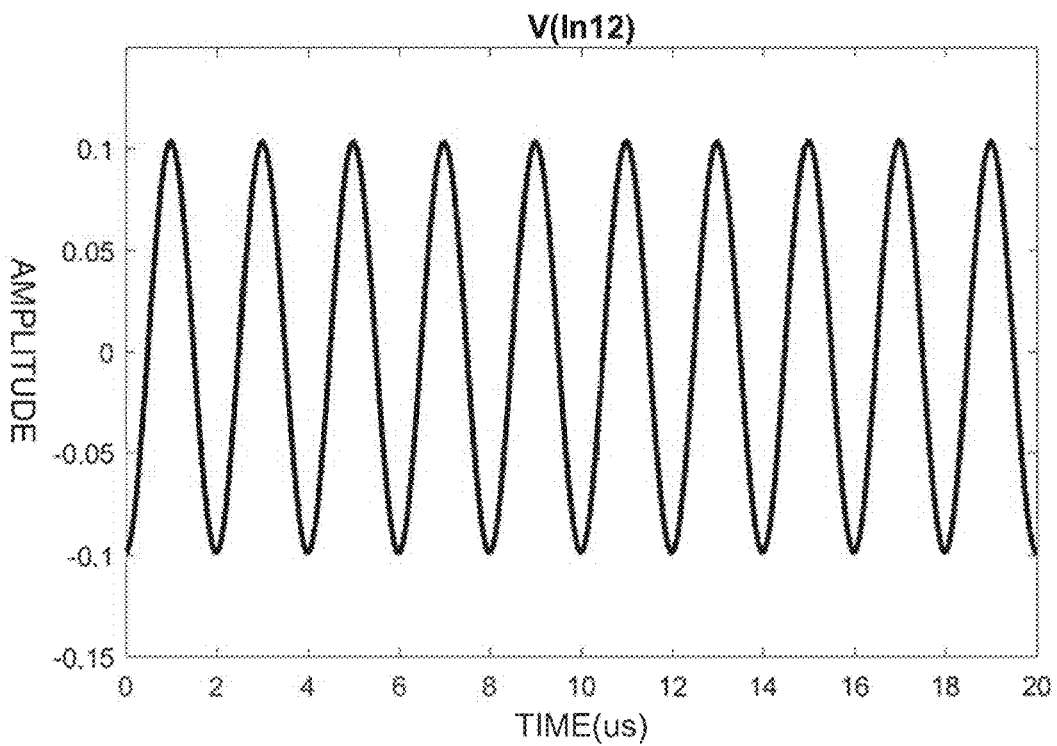
FIGS. 19A-D illustrate signal plots of a typical 500 kHz ablation input signal that is in a frequency range to be attenuated by the RF filter of the EP hardware system, according to an exemplary embodiment.
Figure 19B:
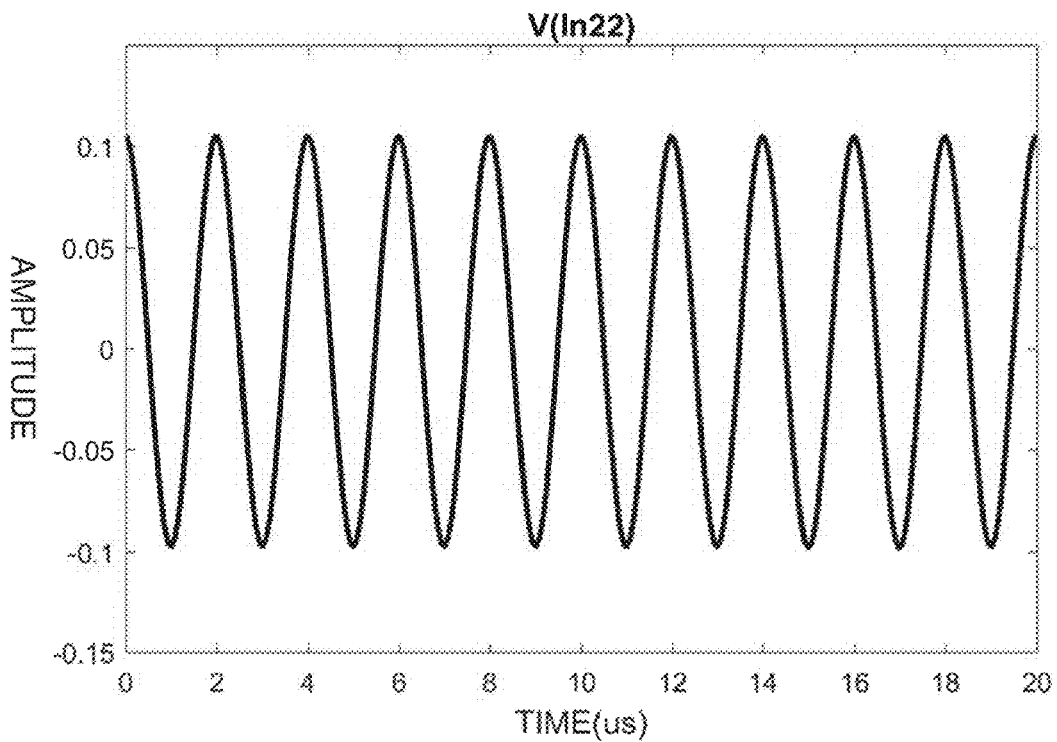

As seen in FIGS. 19A-19B, the ablation signal input is a 0.2 Vpp, 500 kHz sine wave applied to In12 (FIG. 19A) and −0.2 Vpp, 500 kHz sine applied to In22 (FIG. 19B). This results in a 0.4 V, 500 kHz differential signal. This signal is in the frequency range to be attenuated by the RF filter 702 of Block 2 (FIGS. 4, 404a and 404b).

Figure 19C:
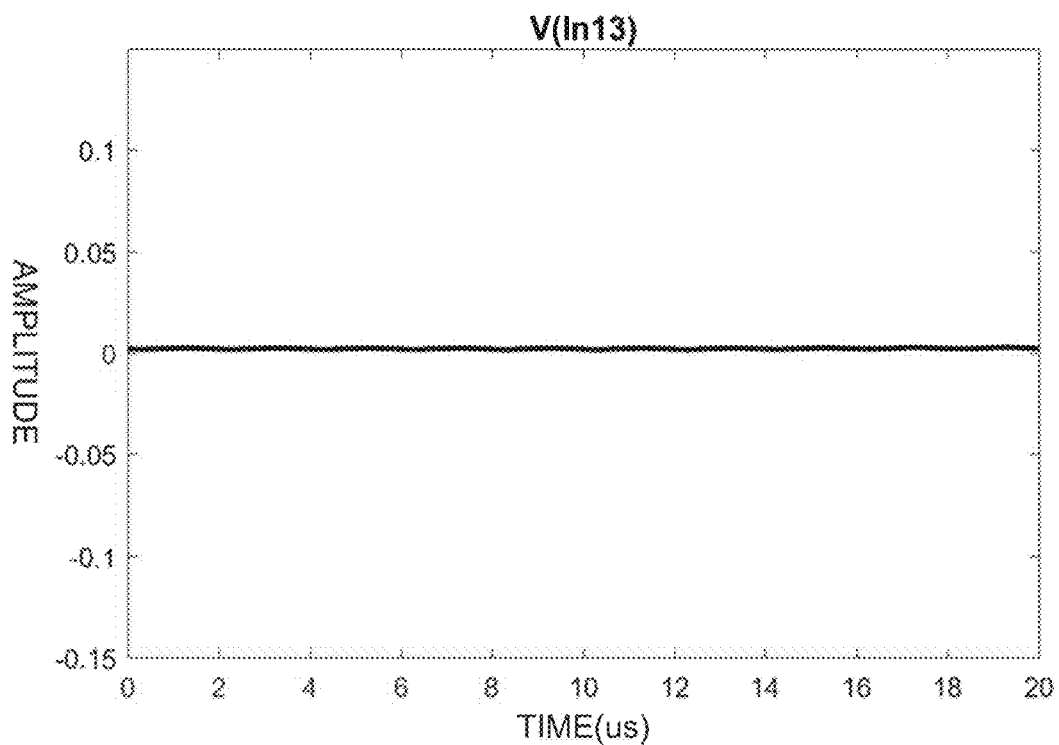
Figure 19D:
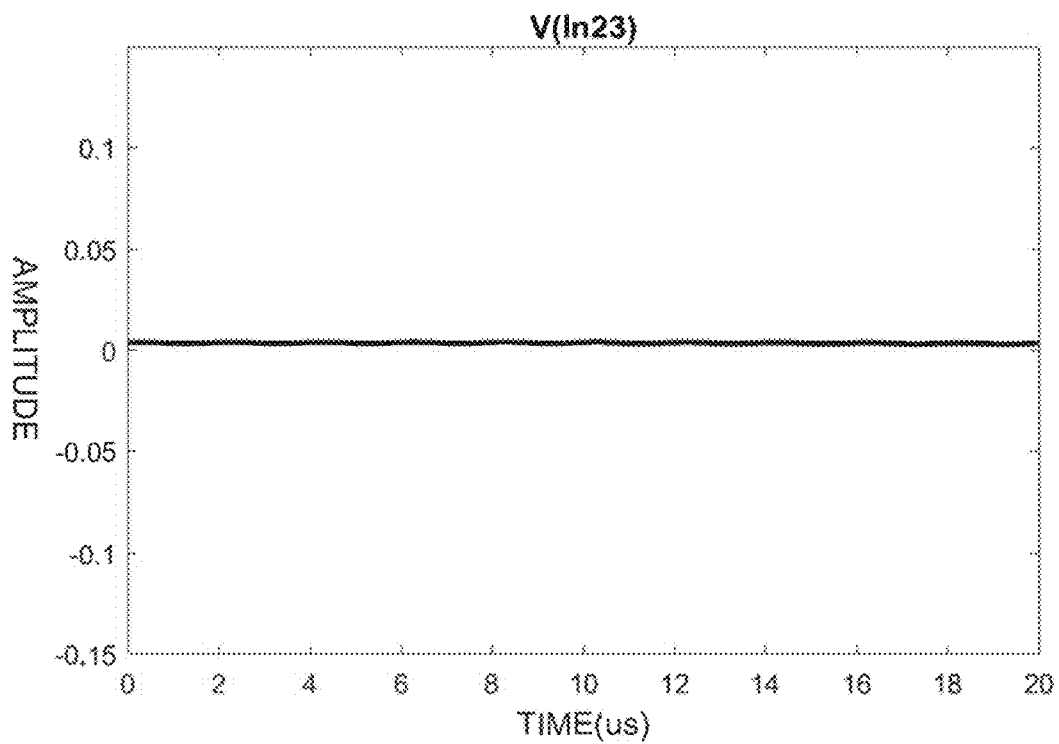

FIGS. 19C-19D illustrate plots of the output of the RF filter 702 (Block 2) In13 (and the symmetric lower branch RF filter output In23) when the circuit receives an ablation signal. The plots V(In13) of FIG. 19C and V(In23) of FIG. 19D are shown at the same scale as the input. The signal can be seen to be attenuated to a few millivolts.

Figure 20A:
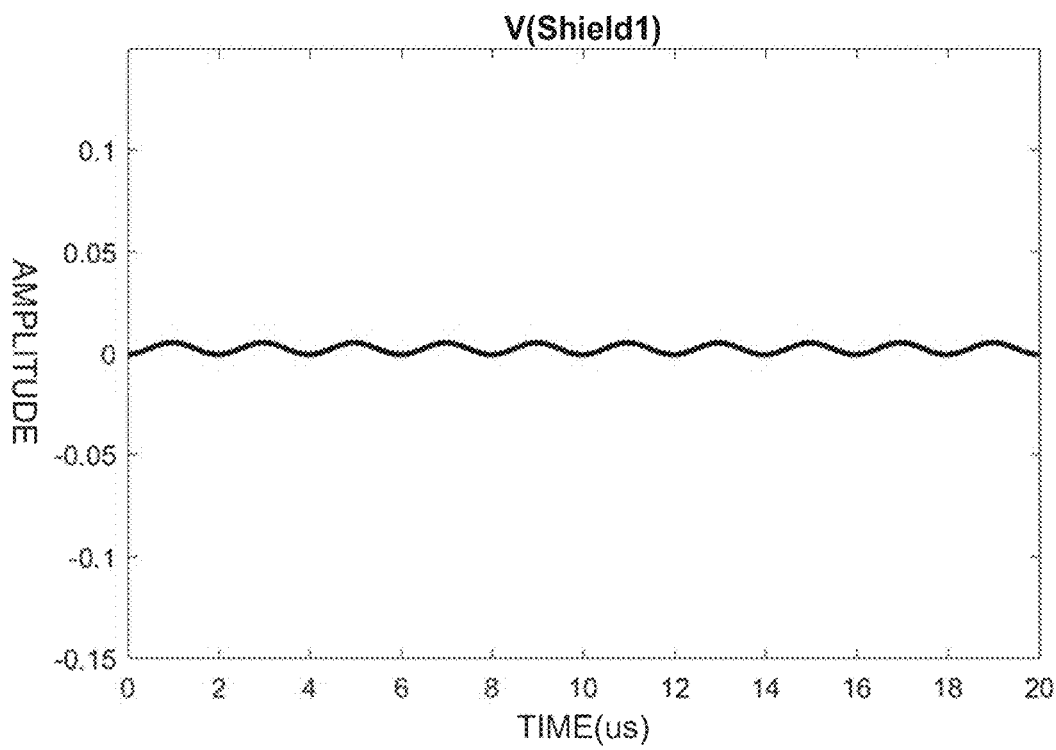
FIGS. 20A-20B illustrate signal plots of a typical 500 kHz ablation input signal at the shield inputs that enable the RF filter to attenuate the input signal to the EP hardware system, according to an exemplary embodiment.
Figure 20B:
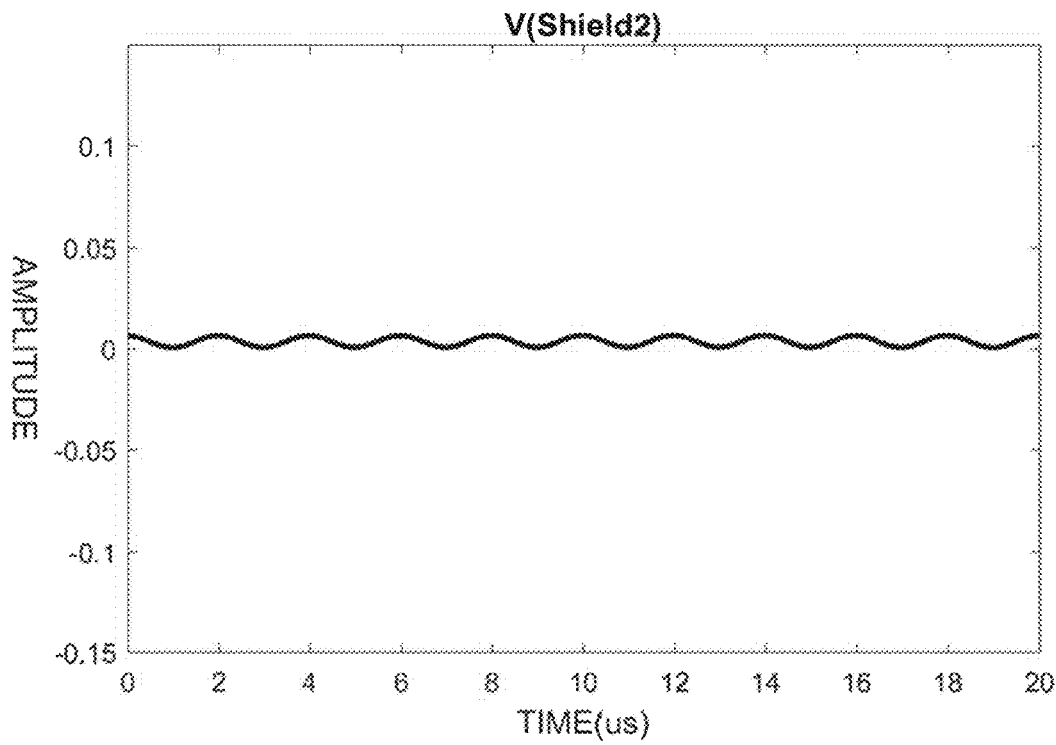

The plots of V(Shield1) and V(Shield2) shown in FIGS. 20A and 20B, respectively, illustrate that the same signals over the shield input (see Shield1 of FIG. 7, for example) are also greatly attenuated, effectively grounding the lower plates of capacitors 714, 716, 706 of the upper branch of the RF filter 702 in FIG. 7, and the corresponding capacitors on the symmetrical lower branch of the RF filter (not shown), to enable the RF filter to attenuate the 500 kHz ablation signal.

Figure 21A:
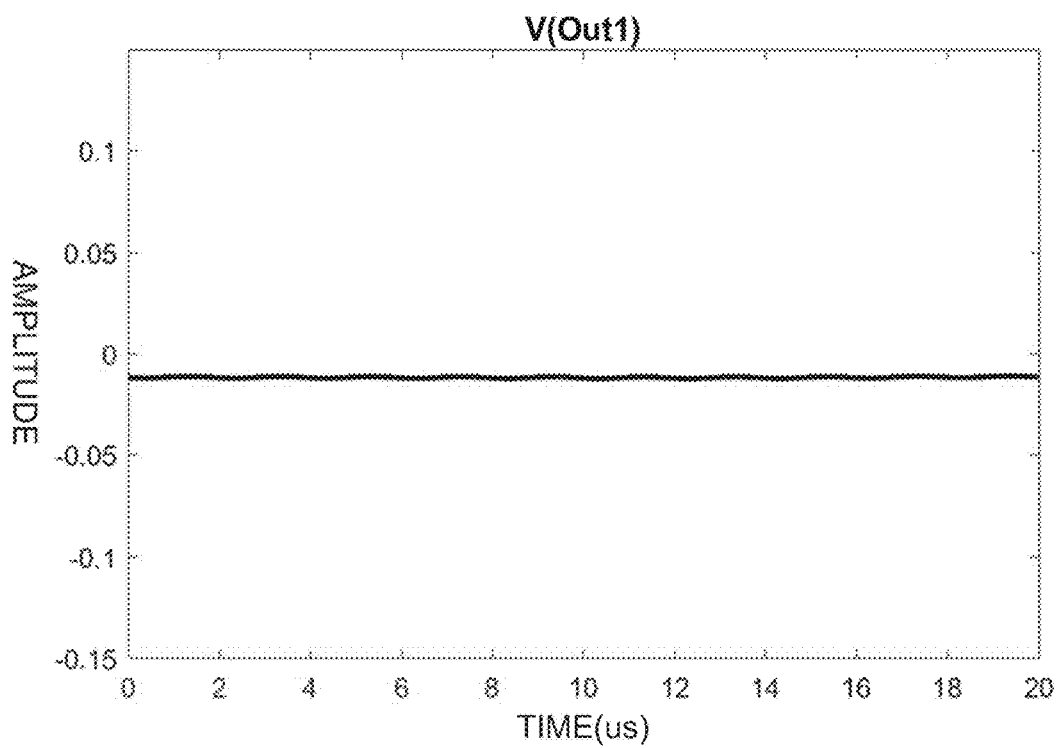
FIGS. 21A-21D illustrate signal plots of a typical 500 kHz ablation input signal that has been attenuated after it has traveled through the instrumentation amplifier and after it has traveled through the fully differential op amps of the EP hardware system, according to an exemplary embodiment.
Figure 21B:
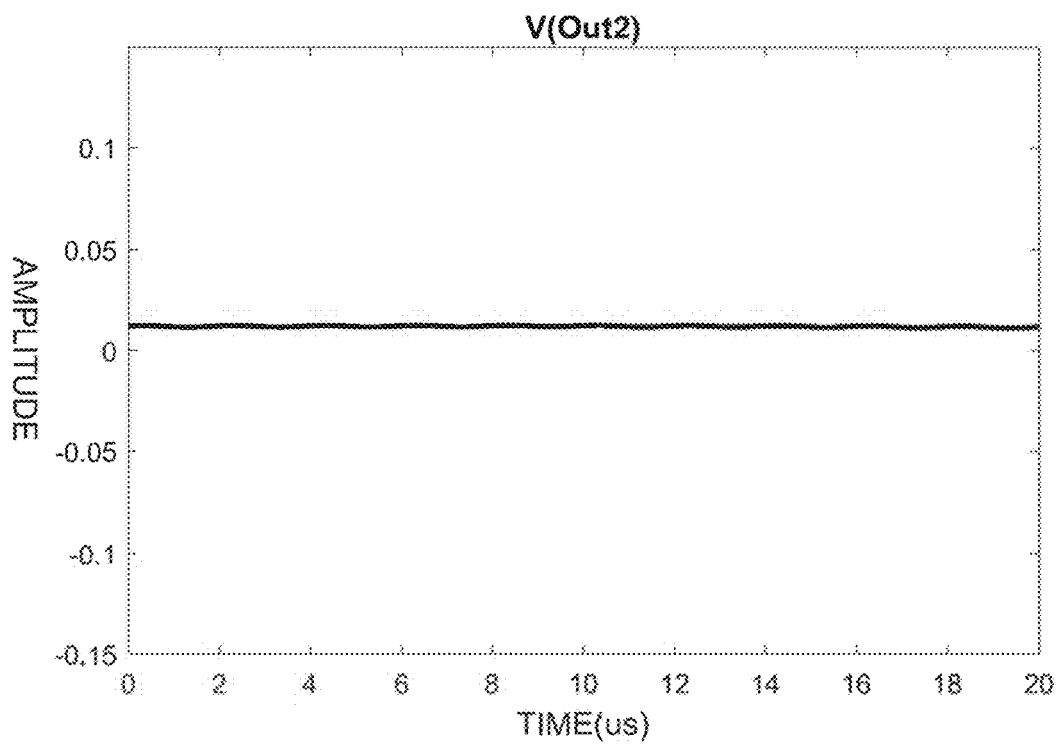

FIGS. 21A and 21B illustrate plots of the signals V(Out1) and V(Out2), respectively, at the outputs of the Block 5 (instrumentation amplifier 1001 of FIG. 10), with a gain of 20. The remaining 500 kHz signal goes through this 20× gain stage, but the filtering on this stage (from capacitors 1010 and 1012) limits the gain at 500 kHz to approximately 1×.

Figure 21C:
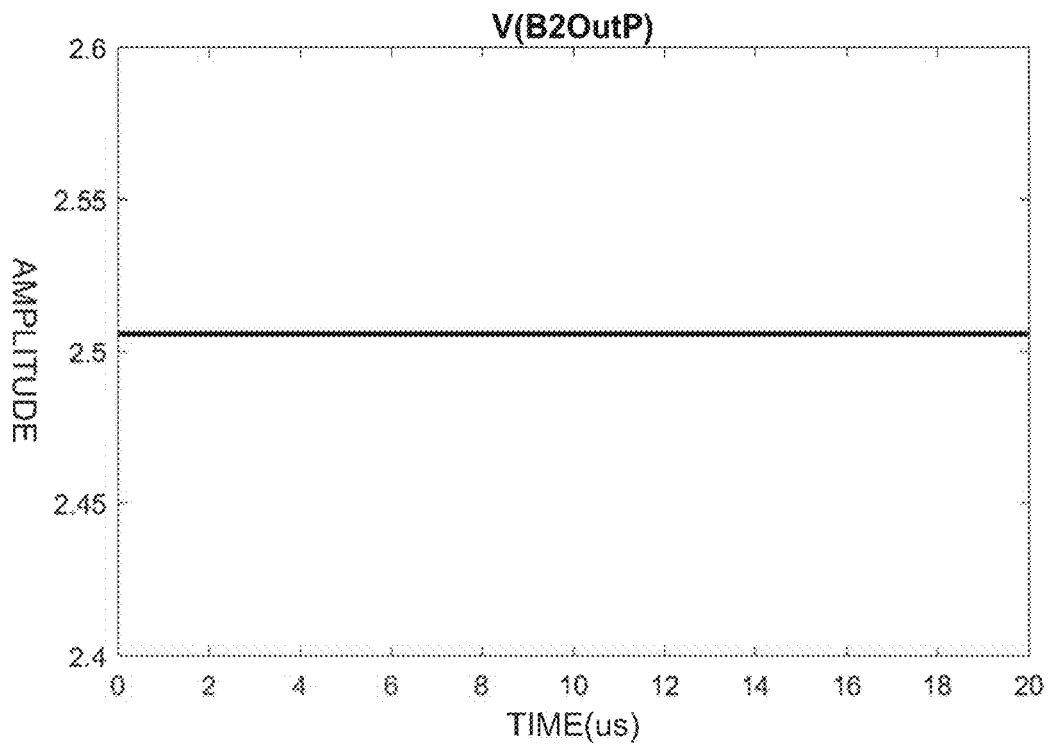
Figure 21D:
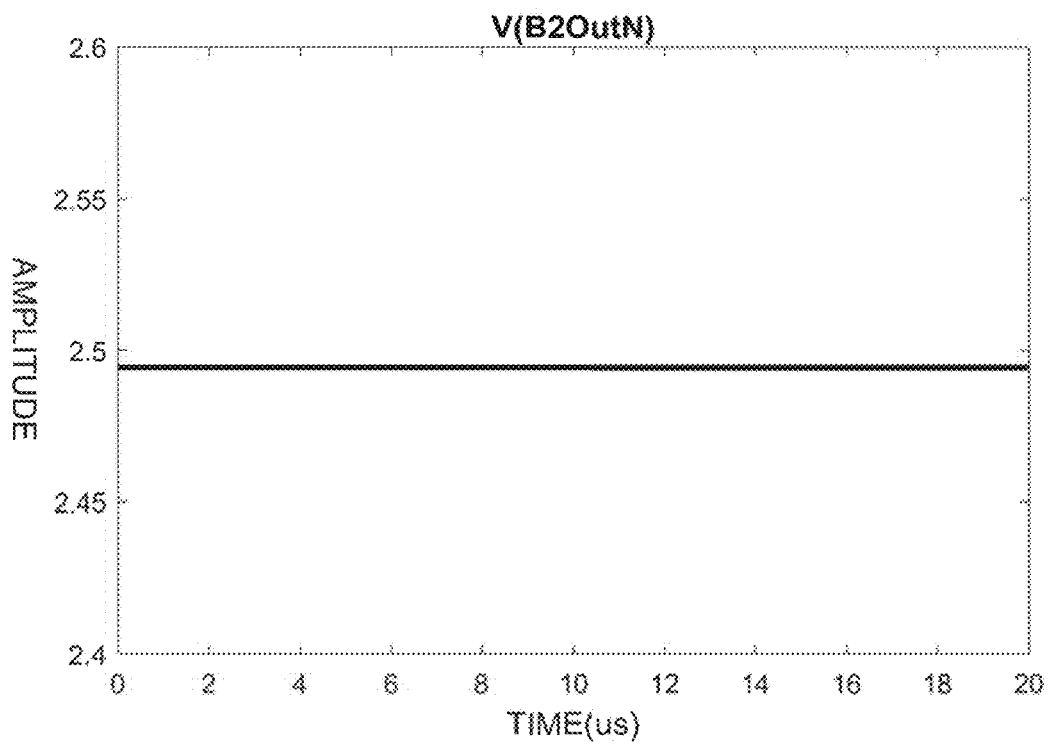

As shown in FIGS. 21C-21D, the successive fully differential operational amplifiers 1017, 1021 in Blocks 6 and 7 of FIG. 10 (and their negative, lower branch circuit equivalents) continue to filter the 500 kHz signal until it is less than 0.5 mV at B2OutP (FIG. 21C) and B2OutN (FIG. 21D). The remaining signal is removed by the filter on the Block 8 A/D converter (see FIG. 4, 416), which provides 100 dB attenuation above 1000 Hz. The ablation signal is thus eliminated through the combined responses of the RF filter (Block 2), the instrumentation amplifier (Block 5), and the fully differential operational amplifiers (Blocks 6 and 7).

Hardware/Software Interface

FIG. 5A illustrates the relationship between the hardware and software of the disclosed EP recording system, according to some embodiments. The Main System Unit (MSU) 504 contains the hardware circuitry of the EP recording system. In FIG. 5A, the ECG board 506 with WCT 507 corresponds to the ECG board 302 and WCT 314 shown in FIG. 3. (For cross-reference, the ECG board 302, 506 digital signal outputs are V1-V6 310 and I-II 312.) Similarly, the IC board 508 corresponds to the IC board 316 in FIG. 3. (For cross-reference, the IC board 316, 508 digital signal outputs IC1..ICN are ICUniWCT1-ICUniWCT2 326, ICUniIN-DIF1-ICUniINDIF2 328, and ICDiff1..ICDiffN 330.) To communicate the digital signal outputs from the ECG board 506 and IC board 508 to the software of the Main Processing Unit (MPU) 514, a Communication Module 510, and a fiber optic link 512 are provided.

According to some embodiments, the Communication Module 510 of the MSU 504 transmits the independent digital signals from the A/D converter 416, 534 of the ECG board 506 and IC board 508 to the MPU 514 over a fiber optic link 512 for digital signal processing. The Communication Module 510 samples the output channels from the A/D converter 416, 534, converts them to serial format, and transmits the data over the fiber optic link 512. The signals are converted back to a parallel format at the receiving end of the fiber optic link 512 in the MPU 514.

In this specification, the ECG board 302, 506 and IC board 316, 508 are named thusly for sake of convenience. As would be understood by a person of ordinary skill in the art, the circuitry of the ECG board 302, 506 and IC board 316, 508 can accept other physiologic signals from various types of electrodes other than ECG and IC electrodes.

EP Recording System Software Description

Provided herein are system, apparatus, device, method and/or computer program product embodiments, and/or combinations and sub-combinations thereof, for processing and displaying multiple signals in near real-time. For example, the embodiments may involve processing and display multiple biomedical signals (e.g., EP signals) in near real-time. Before describing further details of these embodiments, a brief overview of digital signal processing is provided.

At a high level, digital signal processing is the use of digital processing to identify particular features in a signal, or producing a signal that is of higher quality than the original signal (e.g., by removing noise from the signal). Digital signal processing may be performed on a digitized electrocardiography (ECG) or intracardiac (IC) signal representing the electrical activity of a heart over a period of time.

To perform digital signal processing on an analog signal, the analog signal needs to be converted to digital form. An analog-to-digital (AD) converter such as A/D converter 416 can convert the analog signal to digital form, as is well known to a person of ordinary skill in the art.

Digital signal processing may involve applying a digital signal processing function to one or more signal samples in a sequence of signal samples for a signal. A digital signal processing function can be a sequence of mathematical operations and computational algorithms. A digital signal processing function can measure, filter, compress, or optimize a signal sample, for example.

Digital signal processing can use different digital signal processing functions depending on the type of analysis and the type of signal being processed. For example, digital signal processing can use a different digital signal processing function to identify particular words in a speech signal or to remove motion blur from a video signal.

Digital signal processing systems have many applications such as audio signal processing, audio compression, digital image processing, video compression, speech processing, speech recognition, digital communications, digital synthesizers, radar, sonar, financial signal processing, and seismology. But conventional digital signal processing systems often cannot be used in certain applications such as biomedical signal processing. This is because conventional digital signal processing systems, including current EP solutions, are often unable to simultaneously display multiple signals in near real-time. Moreover, conventional solutions do not enable a user to dynamically apply a new digital signal processing function to a base signal. And, conventional solutions are often unable to synchronize the processing and display of multiple signals in near real-time. This is often problematic in clinical settings because the ability of a physician to make an effective clinical diagnosis may depend on comparing multiple signals at the same point in time. Finally, conventional EP systems that use analog filters are often unable to take full advantage of digital signal processing. This is because when functions are implemented in hardware, the options are greatly restricted. For example, the functions cannot be removed and therefore the full potential of digital signal processing cannot be obtained.

Figure 26:
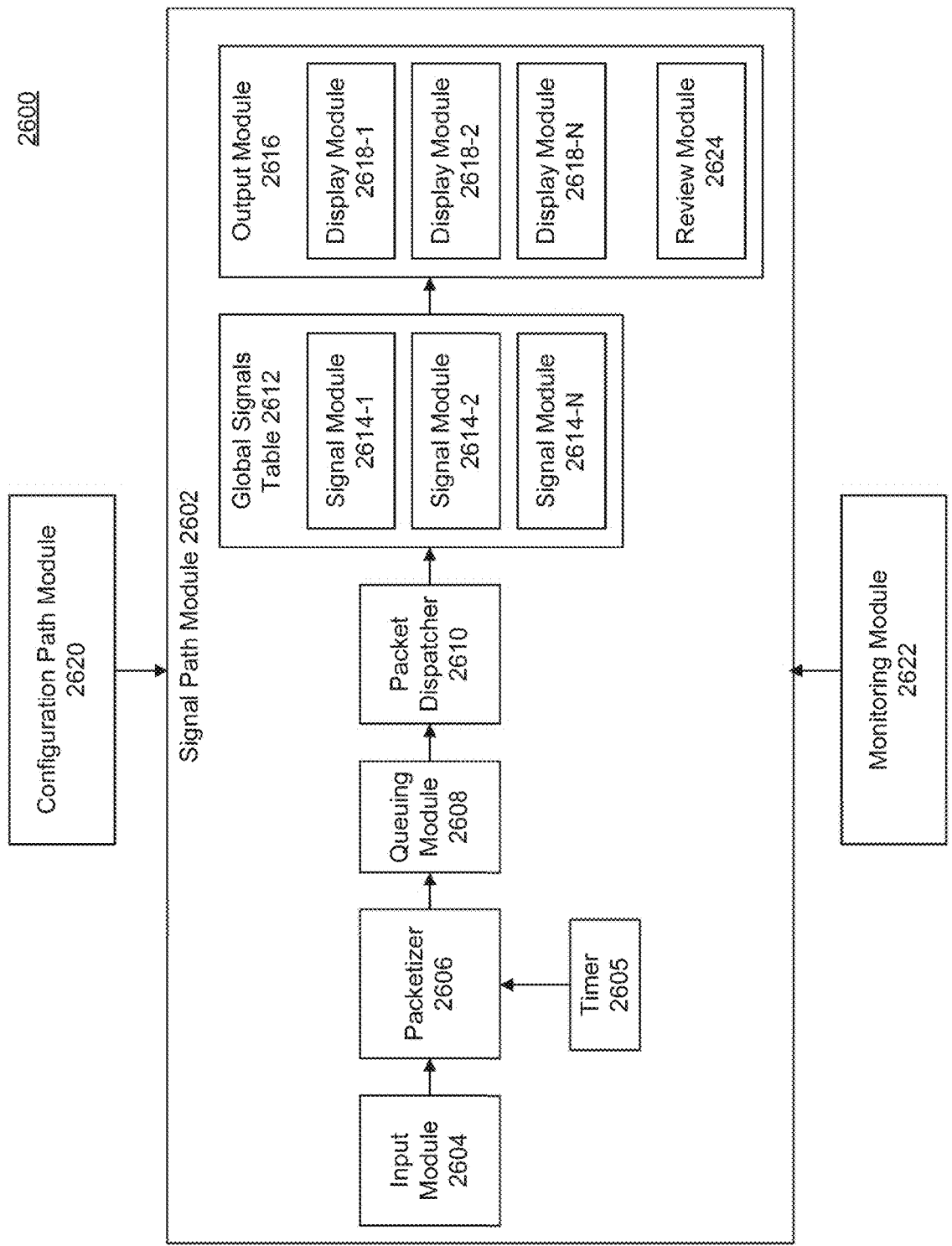
FIG. 26 is a block diagram of a system for processing and displaying multiple signals in near real-time, according to some embodiments.

FIG. 26 is a block diagram of a system 2600 for processing and displaying multiple signals in near real-time, according to some embodiments. System 2600 can represent MPU (Software) 514 in FIG. 5A, and implement digital processing stage 528 of FIG. 5B. System 2600 includes signal path module 2602, configuration path module 2620, and monitoring module 2622. Signal path module 2602, configuration path module 2620, and monitoring module 2622 can be software modules capable of being executed by a processor (or processors) such as processor 5004 in FIG. 50. Alternatively, a plurality of processors can be used.

Signal path module 2602 includes input module 2604, timer 2605, packetizer 2606, queuing module 2608, packet dispatcher 2610, global signals table 2612, and output module 2616. Input module 2604, timer 2605, packetizer 2606, queuing module 2608, packet dispatcher 2610, global signals table 2612, and output module 2616 can be software modules capable of being executed by a processor (or processors) such as processor 5004. Signal path module 2602 solves at least the technological problem of how to synchronize the processing and display of multiple signals in near real-time. Signal path module 2602 solves this technological problem using a novel multistage process involving packetization, queuing, and processing delay equalization, as described below.

In a first stage, input module 2604 can receive signal samples for one or more base signals. A base signal can be a signal before any digital signal processing is applied. For example, a base signal can be a biomedical signal such as an ECG or IC signal. As would be appreciated by a person of ordinary skill in the art, a base signal can be various other types of signals. Input module 2604 can receive signal samples for multiple base signals. For example, input module 2604 can receive signal samples of an IC signal and signal samples of an ECG signal.

Input module 2604 can receive signal samples of a base signal from a hardware device associated with MSU (Hardware) 504 in FIG. 5. For example, input module 2604 can receive signal samples from a hardware device such as EGG board 302 or IC board 316 in FIG. 3. Input module 2604 can also receive signal samples from data stored in a computer file. For example, the computer file can contain previously recorded signal samples received from a hardware device.

Input module 2604 can receive signal samples from a hardware device via A/D converter stage 534. For example, input module 2604 can receive signal samples of a base signal from EGG board 302.

Input module 2604 can receive signal samples of a base signal from an electrode attached to a hardware device. For example, input module 2604 can receive signal samples for each of eight (8) electrodes attached to ECG board 302. As would be appreciated by a person of ordinary skill in the art, input module 2604 can receive more or fewer signal samples depending on the number of hardware devices connected to input module 2604, and the number of electrodes attached to each hardware device.

Input module 2604 can store the one or more signal samples for each base signal in a computer storage device for later analysis by review module 2624. For example, input module 2604 can store the one or more signal samples in main memory 5008 or hard disk drive 5012 in FIG. 50. This enables a user (e.g., a physician) to review the one or more signal samples for each base signal after having been acquired.

Input module 2604 can dispatch the one or more signal samples for each base signal to packetizer 2606. Packetizer 2606 can perform preprocessing on the received signal samples. Packetizer 2606 can perform preprocessing on the received signal samples to ensure that the resulting signal is compatible with later stages in signal path module 2602. As would be appreciated by a person of ordinary skill in the art, the type of preprocessing that packetizer 2606 performs can depend on the type of base signal. For example, packetizer 2606 can convert the binary values of the received signal samples to their corresponding physical values, e.g., for display of the base signal.

After preprocessing the received signal samples, packetizer 2606 can store the one or more signal samples of a base signal into a packet. A packet may be a consecutive sequence of N signal samples belonging to the same base signal. Packetizer 2606's storage of signal samples into packets can enable signal path module 2602 to synchronize the processing and displaying of multiple signals in near real-time, especially on a non-real-time operating system. In other words, a packet is the unit of processing in signal path module 2602.

Packetizer 2606 can store one or more signal samples in a packet based on timer 2605. Timer 2605 can be a high-resolution timer. For example, timer 2605 can be a Microsoft Windows® high-resolution timer having a 1-millisecond resolution. Timer 2605 can be set to an amount of time associated with receiving a fixed number of signal samples (e.g., N signal samples) from a hardware device or from a computer file. The fixed number of signal samples may correspond to the number of signal samples capable of being stored in a packet.

Packetizer 2606 can use timer 2605 to ensure that each packet contains the same number of signal samples. Specifically, packetizer 2606 can set timer 2605 to an amount of time associated with receiving a given number of signal samples of a base signal. In other words, packetizer 2606 can expect to receive a certain number of signal samples when timer 2605 is triggered.

Packetizer 2606 can start timer 2605. Packetizer 2606 can then store signal samples received from input module 2604 into a packet until timer 2605 is triggered. Packetizer can then dispatch the packet to queuing module 2608. Packetizer 2606 can then restart timer 2605. Packetizer 2606 can then store a new set of signal samples received from input module 2604 into a new packet until timer 2605 is triggered again.

Packetizer 2606 can assign a tag to each packet. Packetizer 2606 can assign the same tag to each packet associated with a different base signal for the same period of time. This assignment can enable signal path module 2602 to synchronize the processing and displaying of packets for different base signals for the same period of time. The assigned tag may be used by a display module 2618 to synchronize the output of different signals. In other words, the display module 2618 can work on the same tag at any given time.

The assigned tag can correspond to the time period in which signal samples in the corresponding packet were received. Specifically, the tag can correspond to the sample number of the first signal sample in the corresponding packet. For example, packetizer 2606 can store sixteen (16) signal samples in each packet. In this case, packetizer 2606 can store the first set of signal samples in a packet with a tag of 0. Packetizer 2606 can store the second set of signal samples in a packet with a tag of 15. Packetizer 2606 can store the subsequent sets of signal samples in packets with tags of 31, 47, 64, etc. As would be appreciated by a person of ordinary skill in the art, other tag assignment conventions can be employed.

After packetization, packetizer 2606 can store each generated packet associated with a given base signal in queuing module 2608. Queueing module 2608 is shown in FIG. 27.

Figure 27:
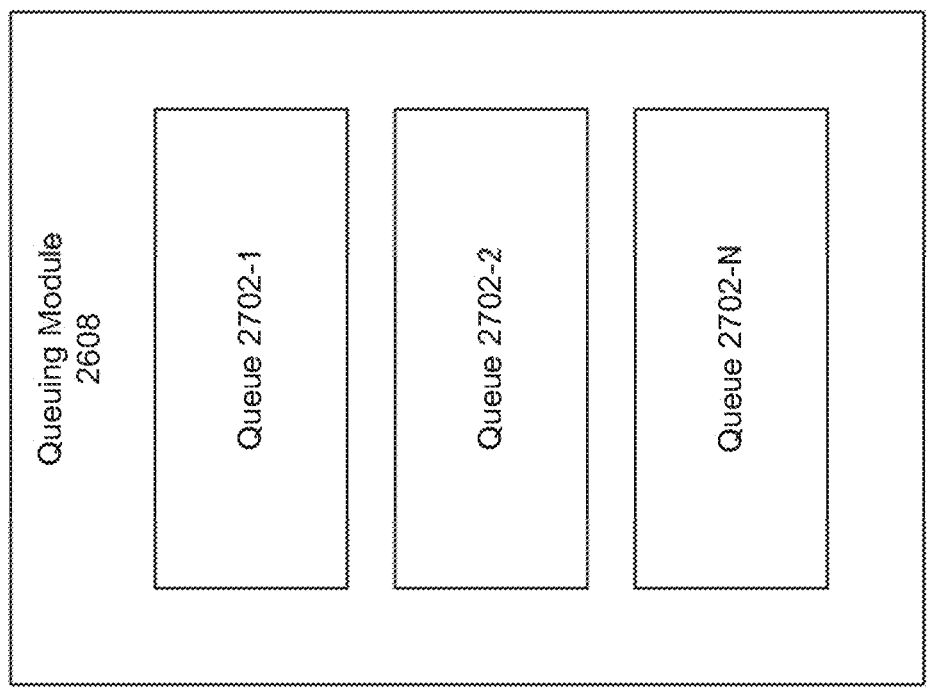
FIG. 27 is a block diagram of a queuing module for the storage of generated packets associated with different base signals, according to some embodiments.

FIG. 27 is a block diagram of queuing module 2608 for the storage of each generated packet associated with a different base signal, according to some embodiments. Queueing module 2608 solves at least the technological problem of how to dynamically apply multiple different digital signal processing functions to the same base signal. Queueing module 2608 solves this technological problem by storing generated packets associated with each base signal in separate queues that can be dynamically processed by different signal modules 2614. FIG. 27 is discussed with reference to FIG. 26.

Queuing module 2608 includes one or more queues 2702. For example, in FIG. 27, queuing module 2608 includes queue 2702-1, queue 2702-2, and queue 2702-N. Each queue 2702 can be associated with a given base signal. Queue 2702 can be a queue data structure that stores items in the order they are inserted. For example, the first item inserted into queue 2702 is the first item removed from queue 2702. In other words, queue 2702 is a first-in-first-out (FIFO) data structure. As would be appreciated by a person of ordinary skill in the art, queue 2702 can be implemented using an array, linked list, or various other data structure.

Packetizer 2606 can store each generated packet associated with a given base signal in a corresponding queue 2702. For example, packetizer 2606 can store generated packets associated with an IC signal into queue 2702-1, and generated packets associated with an ECG signal into queue 2702-2.

Packetizer 2606 can store each packet in a queue 2702 in the order generated. This can ensure that the signal samples in the generated packets are processed in the order they are received from the hardware device or from the computer file.

Returning to FIG. 26, packet dispatcher 2610 can dispatch a generated packet from a queue 2702 in FIG. 27 to one or more signal modules 2614 in global signals table 2612 for digital signal processing. Packet dispatcher 2610 solves at least the technological problem of how to dynamically apply multiple different digital signal processing functions to the same base signal. Packet dispatcher 2610 solves this technological problem by dynamically dispatching generated packets associated with each base signal to the appropriate one or more signal modules 2614 for digital signal processing.

Packet dispatcher 2610 can continuously scan the one or more queues 2702 in queuing module 2608. Each time packet dispatcher 2610 detects a new packet available in a queue 2702 in queuing module 2608, packet dispatcher 2610 can remove the new packet from the queue 2702. Packet dispatcher 2610 can then dispatch the new packet to one or more signal modules 2614 in global signal tables 2612 for digital signal processing. Packet dispatcher 2610 can dispatch the same packet to multiple signal modules 2614 so that the base signal can be simultaneously processed using different digital processing functions. Moreover, because packet dispatcher 2610 can dispatch packets from different queues 2702 to different signal modules 2614, different base signals can be simultaneously processed using different digital signal processing functions.

Packet dispatcher 2610 can dispatch a new packet from a queue 2702 to one or more signal modules 2614. Packet dispatcher 2610 can dispatch the new packet to one or more signal modules 2614 using global signals table 2612. Global signals table 2612 can be a fixed size array. Each element of the array can be associated with a given base signal, and thus a given a queue 2702. For example, if there are 100 base signals, global signals table 2612 can be a fixed size array of 100 elements. Moreover, for each element of the array, there can be one or more signal modules 2614 designed to process the corresponding base signal. In some embodiments, each element of the array can be a fixed size array itself. Each element of this subarray can be associated with a given signal module 2614. For example, if there are 10 signal modules 2614, this subarray can contain 10 elements. Thus, by way of example and not limitation, global signals table 2612 can be a 100×10 array.

Packet dispatcher 2610 can dispatch the new packet to a signal module 2614 by checking the corresponding element in the subarray associated with the base signal of the new packet. Specifically, packet dispatcher 2610 can determine whether the corresponding element in the subarray indicates that the signal module 2614 is assigned to the base signal associated with the packet.

In some embodiments, global signals table 2612 can indicate whether a given signal module 2614 is assigned to a given base signal by storing a '0' or '1' at the corresponding element in the subarray associated with the given signal module 2614. For example, global signals table 2612 can indicate that the given signal module 2614 is not assigned to the given base signal by storing a '0' at the corresponding element in the subarray. In some other embodiments, global signals table 2612 can indicate whether a given signal module 2614 is assigned to a given base signal by storing a reference to the given signal module 2614 at the corresponding element in the subarray. As would be appreciated by a person of ordinary skill in the art, the reference can be a memory pointer, flag, handle, or other type of identifier.

Packet dispatcher 2610 can also dispatch the new packet to one or more signal modules 2614 using a lookup table. The lookup table may map a given queue 2702 to one or more signal modules 2614. Packet dispatcher 2610 can dynamically determine which one or more signal modules 2614 are associated with a given queue 2702 using the lookup table. Packet dispatcher 2610 can then dispatch the packet to the one or more determined signal modules 2614 for digital signal processing.

Before packet dispatcher 2610 can begin dispatching packets to one or more signal modules 2614 for digital signal processing, configuration path module 2620 can configure signal path module 2602. Configuration path module 2620 can perform this configuration during initialization of system 2600, or when a user applies a new configuration to signal path module 2602. Configuration path module 2620 is shown in FIG. 28.

Figure 28:
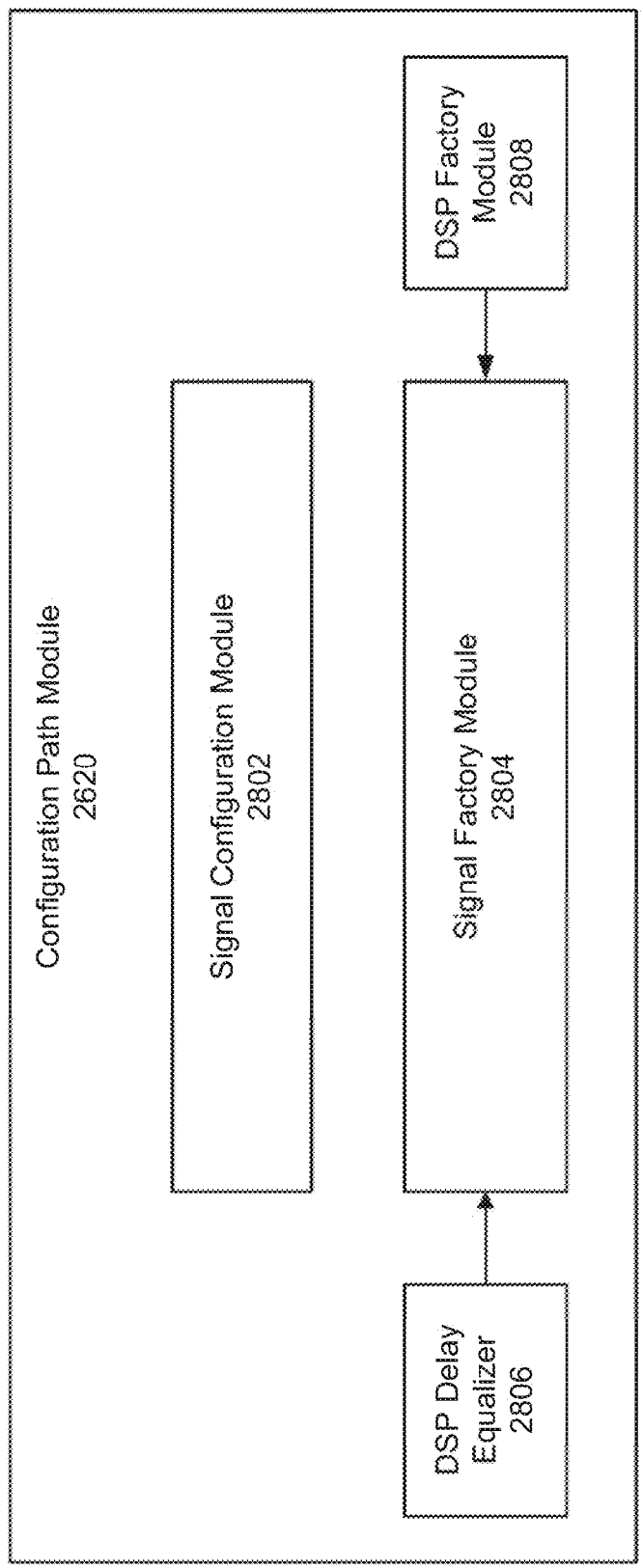
FIG. 28 is a block diagram of a configuration path module for generating at runtime time-aligned signals that are processed from a set of base signals, according to some embodiments.

FIG. 28 is a block diagram of configuration path module 2620 for configuring signal path module 2602 to synchronize the processing and display of multiple signals in near real-time, according to some embodiments. Configuration path module 2620 solves at least the technological problem of how to synchronize the processing and display of multiple signals associated with one or more base signals in near real-time. Configuration path module 2620 solves this technological problem by equalizing the processing delays of each signal module 2614 such that each signal module 2614 completes processing of the same corresponding packet at approximately the same time. FIG. 28 is discussed with reference to FIG. 26.

Configuration path module 2620 includes a signal configuration module 2802, a signal factory module 2804, a digital signal processor (DSP) equalizer 2806, and a DSP factory module 2808. Configuration path module 2620 is a software module capable of being executed by a processor (or processors) such as processor 5004. Configuration path module 2620 controls the execution of signal factory module 2804, DSP equalizer 2806, and DSP factory module 2808. Signal factory module 2804, DSP equalizer 2806, and DSP factory module 2808 can be software modules capable of being executed by a processor (or processors) such as processor 5004.

During initialization of system 2600, or in response to a user applying a new configuration to system 2600, configuration path module 2620 can generate and configure one or more signal modules 2614 in global signals table 2612. In some embodiments, the execution of signal path module 2602 and monitoring module 2622 can be paused during the execution of configuration path module 2620.

Configuration path module 2620 includes signal configuration module 2802. Signal configuration module 2802 can receive one or more signal processing specifications. A signal processing specification can be used to generate and configure a signal module 2614. A signal processing specification may specify a base signal to process, the lengths of input and output packet queues for a signal module 2614, and a digital signal processing function to use to process the base signal. Signal configuration module 2802 can receive the one or more signal processing specifications from a computer file. The file may contain one or more signal processing specifications previously specified by a user. Signal configuration module 2802 can also receive a signal processing specification via a graphical user interface (GUI) in which a user manually enters the signal processing specification using a series of computer mouse, touch, keyboard, and/or voice recognition data entry techniques, as would be appreciated by a person of ordinary skill in the art.

In response to receiving one or more signal processing specifications, signal configuration module 2802 can forward the one or more signal processing specifications to signal factory module 2804. Signal factory module 2804 can generate a signal module 2614 based on a signal processing specification. For example, signal factory module 2804 can generate a signal module 2614 as shown in FIG. 29.

Figure 29:
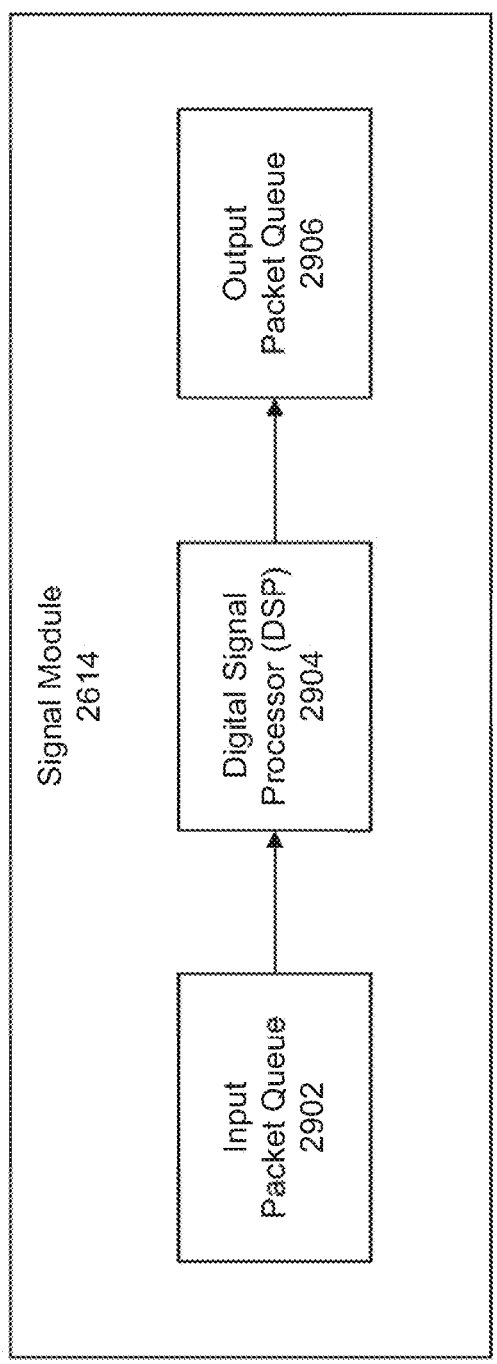
FIG. 29 is a block diagram of a signal module generated by a signal factory module, according to some embodiments.

FIG. 29 is a block diagram of a signal module 2614 generated by signal factory module 2804, according to some embodiments. Signal module 2614 can generate a processed signal from a base signal. Signal module 2614 includes an input packet queue 2902, a digital signal processor (DSP) 2904, and an output packet queue 2906. FIG. 29 can be discussed with reference to FIGS. 26 and 28.

Signal module 2614 includes input packet queue 2902, DSP 2904, and output packet queue 2906. Signal factory module 2804 can generate input packet queue 2902, DSP 2904, and output packet queue 2906 based on a signal processing specification from signal configuration module 2802. Input packet queue 2902 can store one or more packets from packet dispatcher 2610 for processing by DSP 2904. Input packet queue 2902 can be a queue data structure that stores items in the order that they are inserted. For example, the first item inserted into input packet queue 2902 is the first item removed from input packet queue 2902. In other words, input packet queue 2902 can be a first-in-first-out (FIFO) data structure. As would be appreciated by a person of ordinary skill in the art, input packet queue 2902 can be implemented using a linked list, an array, or various other data structure.

Output packet queue 2906 can store one or more packets processed by DSP 2904. Output packet queue 2906 can be a queue data structure that stores items in the order that they are inserted. For example, the first item inserted into output packet queue 2906 is the first item removed from output packet queue 2906. In other words, output packet queue 2906 can be a first-in-first-out (FIFO) data structure. As would be appreciated by a person of ordinary skill in the art, output packet queue 2906 can be implemented using a linked list, an array, or various other data structure.

Signal factory module 2804 can generate DSP 2904 based on a signal processing specification from signal configuration module 2802. Specifically, signal factory module 2804 can request DSP factory module 2808 to generate DSP 2904. DSP factory module 2808 can generate DSP 2904 based on a digital signal processing function specified in the signal processing specification. DSP factory module 2808 can further generate DSP 2904 based on one or more signal processing parameters associated with a digital processing function. For example, DSP factory module 2808 can generate DSP 2904 based on a low-pass filter function and a cutoff frequency specified in a signal processing specification.

Figure 50:
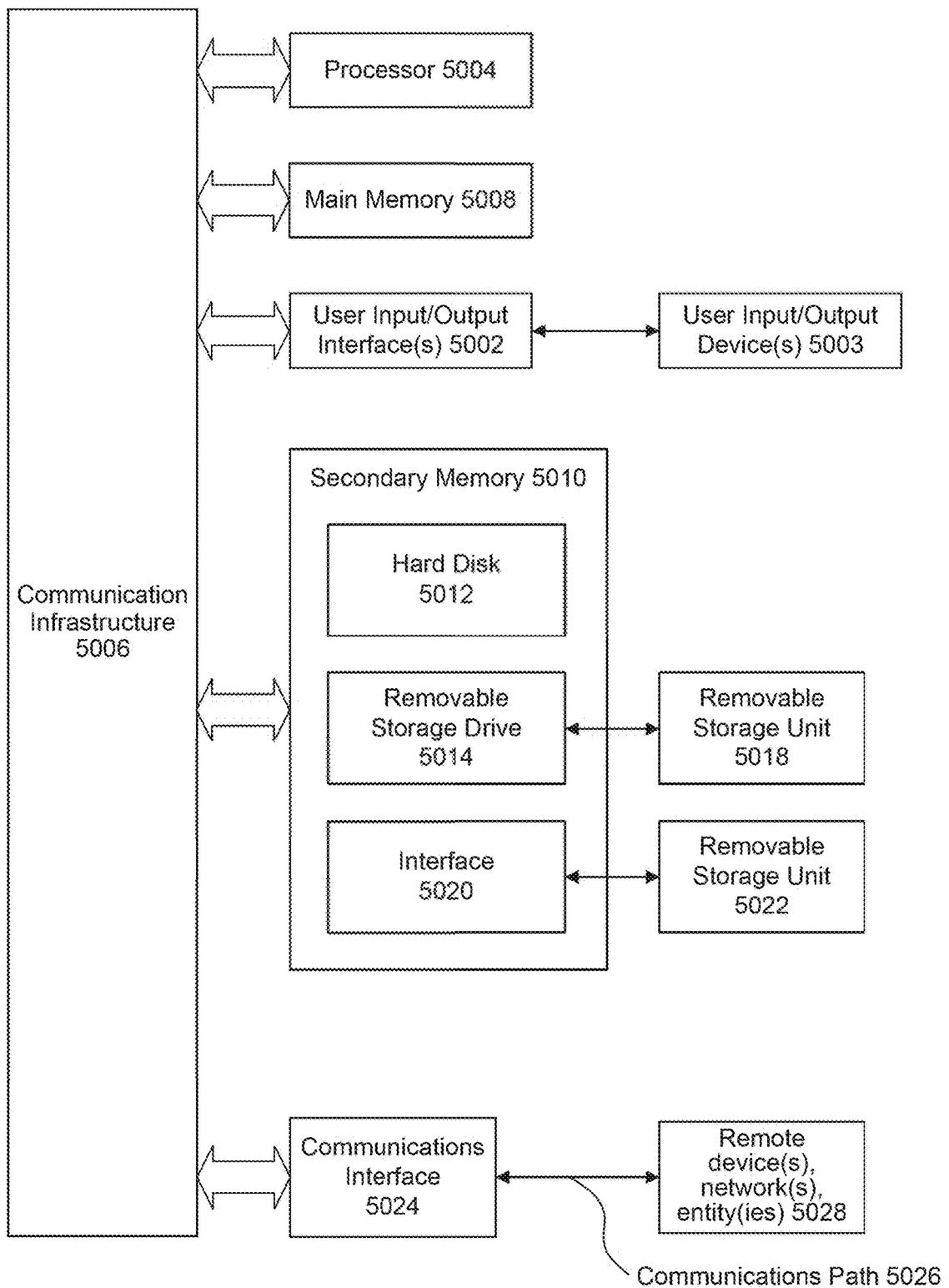
FIG. 50 illustrates an example computer system, according to some embodiments.

A DSP 2904 is a software module capable of being executed by a processor (or processors) such as processor 5004 in FIG. 50. DSP 2904 can apply a digital processing function to one or more packets, and therefore one or more signal samples. As would be appreciated by a person of ordinary skill in the art, a digital processing function may be a mathematical algorithm that takes one or more signal samples as input, processes them, and produces one or more potentially modified signal samples as output. A digital processing function may be implemented using one or more mathematical operations such as a fast Fourier transform. As would be appreciated by a person of ordinary skill in the art, DSP 2904 can apply various types of digital processing functions. For example, DSP 2904 can apply a low-pass filter, a high-pass filter, a band-pass filter, a band-stop filter, a notch filter, a comb filter, an all-pass filter, or various other filters as would be appreciated by a person of ordinary skill in the art.

DSP 2904 can also apply a digital processing function that analyzes a signal for various characteristics. For example, DSP 2904 can apply a digital processing function that determines whether a noise anomaly or signal pattern is present in a signal. DSP 2904 can also analyze a signal by detecting repeated patterns in the signal. This may involve comparing the signal to a previously detected (or recorded or synthesized) signal pattern.

For example, DSP 2904 can determine a late potential in a signal. Specifically, DSP 2904 can determine a noise anomaly followed by subsequent noise anomalies occurring at the same time relative to a matched beat. Each subsequent noise anomaly at the same relative position can increase a confidence level that a late potential has been located. A display module 2618 can then display an indication of the late potential.

Similarly, DSP 2904 can determine an early activation in a signal. Specifically, DSP 2904 can determine an earliest sharp intracardiac signal above a selected threshold occurring within a predetermined segment before a reference point of a matched beat. A display module 2618 can then display an indication of the early activation.

DSP 2904 can detect a pattern in a signal using a correlation function. For example, DSP 2904 can detect a pattern using a mean absolute deviation algorithm. As would be appreciated by a person of ordinary skill in the art, DSP 2904 can use various other types of pattern matching algorithms.

DSP 2904 can detect a pattern based on various signal characteristics. For example, DSP 2904 can detect a pattern based on shape, amplitude, and time characteristics. As would be appreciated by a person of ordinary skill in the art, DSP 2904 can detect a pattern based on various other types of signal characteristics.

DSP 2904 can also include one or more signal processing parameters. The signal processing parameters may control how DSP 2904 applies its digital processing function. For example, DSP 2904 can include one or more signal processing parameters that specify a threshold frequency or an amplitude for filtering. DSP 2904 can also include one or more signal processing parameters that specify a signal pattern to detect, or a noise threshold value.

DSP 2904 can apply its digital processing function to a packet in input packet queue 2902. In some embodiments, DSP 2904 can scan input packet queue 2902 for a new packet to process. In some other embodiments, DSP 2904 can get a notification that a new packet is available in input packet queue 2902. DSP 2904 can then retrieve the packet from input packet queue 2902.

DSP 2904 can apply its digital processing function to the retrieved packet. In other words, DSP 2904 can apply its digital processing function to the one or more signal samples in the packet. DSP 2904 can control how it applies its digital processing function to the one or more signal samples in the packet based on its one or more signal processing parameters. After processing the packet, DSP 2904 can store the packet in output packet queue 2906 for display by output module 2616.

As discussed below, each DSP 2904 can have an associated processing delay. The processing delay can represent the amount of time to complete processing of a packet by the digital processing function of DSP 2904. The processing delay can vary between different DSPs 2904. This variance in processing delay between different DSPs 2904 can cause the DSPs 2904 to output packets for display at different times, as discussed below.

After signal factory module 2804 completes generating input packet queue 2902, DSP 2904, output packet queue 2906, signal factory module 2804 can connect the output of input packet queue 2902 to the input of DSP 2904, and the output of DSP 2904 to the input of output packet queue 2906. Once signal factory module 2804 completes the connection, DSP 2904 can receive packets from input packet queue 2902 representing an unprocessed base signal. DSP 2904 can then process the packets using its digital processing function. DSP 2904 can output the processed packets to output packet queue 2906. Signal factory module 2804 can further configure input packet queue 2902 to receive packets from the base signal specified in the signal processing specification.

Once the signal module 2614 is created, signal factory module 2804 can add it to global signals table 2612. As discussed above, global signals table 2612 can be a fixed size array. Each element of the array can be associated with a given base signal. Moreover, each element of the array can be a fixed size array itself. Each element of this subarray can be associated with a given signal module 2614.

In some embodiments, signal factory module 2804 can add the created signal module 2614 to global signals table 2612 by adding a new array element to each subarray associated with a base signal. This new array element can correspond to the newly created signal module 2614. For example, if global signals table 2612 previously contained ten (10) signal modules 2614, the newly created signal module 2614 can be added at element number 11 in each subarray, for example.

Once the created signal module 2614 is added to global signals table 2612, a user (e.g., a physician) can assign the created signal module 2614 to a given base signal. In some embodiments, global signals table 2612 can indicate whether the created signal module 2614 is assigned to a given base signal by storing a '0' or '1' at the corresponding element in the subarray associated with the created signal module 2614. In some other embodiments, global signals table 2612 can indicate whether the created signal module 2614 is assigned to a given base signal by storing a reference to the created signal module 2614 at the corresponding element in the subarray.

Signal factory module 2804 can generate multiple signal modules 2614. Each signal module 2614 can have a DSP 2904 that applies a different digital signal processing function. As a result, each signal module 2614 can generate a different processed version of the same base signal. This can enable a user to analyze the same base signal in a variety of ways. A user may also want to analyze the time-aligned output of multiple versions of the same base signal. This can enable the user to compare different versions of the same signal at the same point in time or different points in time.

As noted above, conventional digital signal processing systems are often unable to synchronize the display of multiple processed signals in near real-time. This may be because different digital signal processing functions have different processing delays. For example, a current EP system may apply two different digital signal processing functions to the same base signal. But a medical team may want to synchronize the display of the two processed signals. For example, a medical team may want to compare an IC signal and an ECG signal at the same point in time in order to determine a clinical diagnosis. In other words, the medical team may want to time-align the display of the first processed signal with the display of the second processed signal in near real-time. But this may not be possible if the two different digital signal processing functions have different processing delays. This is because one of the digital signal processing functions may complete processing of the base signal more quickly than the other digital signal processing function. As a result, one processed signal may be displayed before the other processed signal.

The processing delay associated with a digital processing function may depend on the complexity of the function. For example, a digital processing function that performs low-pass filtering on a signal may be less computationally-intensive and use minimal memory. As a result, such a digital processing function may have a short processing delay. In contrast, another digital processing function may analyze a signal for particular signal characteristics. This type of digital processing function may be more computationally-intensive and use more memory, and therefore have a longer processing delay.

Because of the different processing delays, one processed signal may be displayed before another processed signal. This synchronization gap may become greater over time.

For example, this synchronization gap may become greater where multiple signals are being processed and displayed in near real-time. This is because the difference in processing delay between two digital signal processing functions may be propagated to each new signal sample.

For example, a first digital signal processing function may have a processing delay of 10 milliseconds for a given base signal. A second digital signal processing function may have a processing delay of 20 milliseconds for the same base signal. The first digital signal processing function may complete processing of a first signal sample of the base signal at 10 milliseconds, and the second digital signal processing function may complete processing of the same first signal sample at 20 milliseconds. Thus, the first signal sample processed by the first digital signal processing function may be displayed at 10 milliseconds, and the first signal sample processed by the second digital signal processing function may be displayed at 20 milliseconds. In other words, the first signal sample processed by the first digital signal processing function may be displayed 10 milliseconds before the first signal sample processed by the second digital signal processing function.

This synchronization gap may increase when the second signal sample is processed. For example, the second signal sample may be received for processing by the first digital signal processing function at time 10 milliseconds, and the second signal sample may be received for processing by the second digital signal processing function at time 20 milliseconds. As a result, the second signal sample processed by the first digital signal processing function may be displayed at 20 milliseconds, and the second signal sample processed by the second digital signal processing function may be displayed at 40 milliseconds. In other words, the synchronization gap may increase by 10 milliseconds for the second signal sample; initially the synchronization gap is 10 milliseconds and subsequently the synchronization gap is 20 milliseconds.

This synchronization gap may increase where the digital signal processing is performed on a non-real-time operating system. Unlike a non-real-time operating system, a real-time operating system is a time bound system with well-defined fixed time constraints. A real-time operating system can guarantee that an application task is accepted and completed in a certain amount of time. In other words, a real-time operating system may provide a level of consistency concerning the amount of time it takes to complete a task.

In contrast, a non-real-time operating system cannot provide any guarantee that an application task is completed in a certain amount of time. For example, a non-real-time operating system may not provide a guarantee that the execution of a particular digital signal processing function is completed in a certain amount of time. As a result, there may be a high degree of variability concerning the amount of time it takes to complete a task. This may be problematic when attempting to synchronize the processing and display of multiple processed signals. This is because a processing delay associated with a digital processing function may vary with each execution. For example, a digital signal processing function may normally complete execution in 10 milliseconds. But on a non-real-time operating system, there may be no guarantee that the digital signal processing function completes execution after 10 milliseconds. For example, the digital signal processing function may complete execution in 30 milliseconds. This variability in processing delay may further increase the synchronization gap.

In some embodiments, this display synchronization problem is solved in a multipronged way using an input packet queue 2902 and an output packet queue 2906 of a signal module 2614, storing signal samples in a packet along with an associated tag, and equalizing the processing delays among one or more DSPs 2904.

An input packet queue 2902 and an output packet queue 2906 can solve the display synchronization problem in three ways. First, they ensure packets, and therefore signal samples, are processed and displayed sequentially. Second, an output packet queue 2906 can synchronize the display of packets at the same point in time by blocking the processing of more packets until existing packets are consumed by output module 2616. In other words, an output packet queue 2906 can provide a feedback mechanism to a DSP 2904 that indicates when the DSP 2904 can stop processing more packets. Finally, an input packet queue 2902 ensures a DSP 2904 has packets to process. For example, when an input packet queue 2902 is empty, a DSP 2904 can stop processing more packets. In other words, an input packet queue 2902 can provide a feedback mechanism to a DSP 2904 to indicate that there are no more packets to process.

DSP delay equalizer 2806 can also solve the display synchronization problem by equalizing processing delays across one or more DSPs 2904. As discussed above, different digital signal processing functions have different processing delays, which may cause the processed signals to be displayed out of sync. Therefore, if configuration path module 2620 generates multiple signal modules 2614, each with a DSP 2904 having a different digital signal processing function, each signal module 2614 can complete processing of a packet with a different processing delay. Because of these different processing delays, the processed signals may be displayed out of sync by output module 2616. DSP delay equalizer 2806 can solve this problem by equalizing the processing delays across the generated signal modules 2614.

In some embodiments, after configuration path module 2620 generates the one or more signal modules 2614, signal factory module 2804 can use DSP delay equalizer 2806 to equalize the processing delays of each generated signal module 2614 such that each signal module 2614 outputs a processed packet to its output packet queue 2906 at the same time. For example, DSP delay equalizer 2806 can determine the relative processing delay between two signal modules 2614. DSP delay equalizer 2806 can then use the determined relative delay to configure a DSP 2904 in the first signal module 2614 to complete processing of a packet at approximately the same time as a DSP 2904 in the second signal module 2614 is designed to complete processing of a packet.

In some embodiments, DSP delay equalizer 2806 can perform the equalization by scanning each generated signal module 2614. During the scan, DSP delay equalizer 2806 can request the processing delay associated with a DSP 2904 in each signal module 2614. DSP delay equalizer 2806 can request the processing delay using an application programming interface (API) of each signal module 2614. In response, each signal module 2614 can return its associated processing delay.

A signal module 2614 can store the processing delay associated with its DSP 2904. The processing delay may be a predefined value specified in the signal processing specification used to generate DSP 2904. In some other embodiments, DSP factory module 2808 can calculate the processing delay of a DSP 2904 based on various factors including the digital processing function used by the DSP 2904, the chosen signal processing parameters, and hardware characteristics such as the speed of the processor such as processor 5004, the size of the memory, and I/O latency.

After determining the processing delay associated with a DSP 2904 in each signal module 2614, DSP delay equalizer 2806 can determine the maximum processing delay among the signal modules 2614. For example, DSP delay equalizer 2806 can determine that signal module 2614-1 has a processing delay of 10 milliseconds, that signal module 2614-2 has a processing delay of 20 milliseconds, and that signal module 2614-N has a processing delay of 50 milliseconds. Based on this, DSP delay equalizer 2806 can determine that the maximum processing delay among the signal modules 2614 is 50 milliseconds.

After determining the maximum processing delay, DSP delay equalizer 2806 can configure the DSP 2904 of each signal module 2614 to have the maximum processing delay. For example, DSP delay equalizer 2806 can set the processing delay of the DSP 2904 of each signal module 2614 using an API. In response, each DSP 2904 can be designed to process a packet using its digital processing function and output the processed packet to its associated output packet queue 2906 at the end of the maximum processing delay. For example, in some embodiments, DSP 2904 can block its output to its output packet queue 2906 if it completes processing a packet prior to the end of the maximum processing delay. In some other embodiments, DSP 2904 can insert idle compute cycles during processing of a packet. As would be appreciated by a person of ordinary skill in the art, various other approaches may be used to cause DSP 2904 to output a processed packet to its output packet queue 2906 at the end of the maximum processing delay.

Packetization and the assignment of tags to packets can solve the display synchronization problem. As discussed above, each generated packet may include a fixed number of signal samples. Each packet may also include a tag indicating the packet's relative position among a sequence of packets. In order to synchronize the display of multiple signals, a display module 2618 can display packets having the same tag. In other words, the display module 2618 can synchronize its display using a tag.

As shown in FIG. 26, output module 2616 can include one or more display modules 2618-1 through 2618-N and review module 2624. Review module 2624 can be a software module capable of being executed by a processor (or processors) such as processor 5004. Review module 2624 can display one or more signals processed by one or more signal modules 2614 at a previous point in time. The display modules 2618 can each be software modules capable of being executed by a processor (or processors) such as processor 5004. A display module 2618 can display one or more live signals processed by one or more signal modules 2614. Each display module 2618 can operate independently of the other display modules 2618. In other words, each display module 2618 can simultaneously display one or more signals on one or more display devices such as an input/output device 5003 in FIG. 50. In some embodiments, each display module 2618 can display its associated one or more signals in a particular GUI window on a given display device.

Each display module 2618 can display one or more signals. Each display module 2618 can receive a packet from an associated output packet queue 2906 in a signal module 2614 in global signals table 2612. Display module 2618 can display a signal based on the packet.

Figure 30:
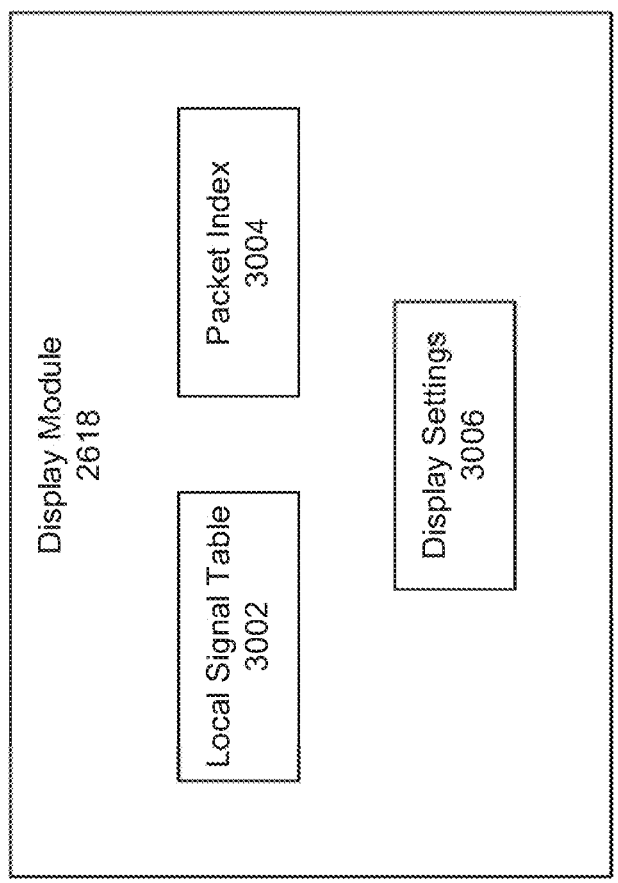
FIG. 30 is a block diagram of a display module for displaying one or more signals, according to some embodiments.

FIG. 30 is a block diagram of a display module 2618, according to some embodiments. Display module 2618 includes a local signal table 3002, a packet index 3004, and display settings 3006. FIG. 30 is discussed with reference to FIG. 29.

As discussed, a display module 2618 can receive a packet from an associated output packet queue 2906 in a signal module 2614. To receive the packet, display module 2618 can maintain a reference to the associated output packet queue 2906 in the signal module 2614. When a display module 2618 is designed to display multiple signals, the display module 2618 can maintain references to the output packet queues 2906 associated with each signal being displayed. The display module 2618 can store the references in its local signal table 3002. Local signal table 3002 can contain a list of one or more references to the output packet queues 2906 associated with each signal being displayed. The display module 2618 can remove a reference from its local signal table 3002 when the associated signal module 2614 is no longer active.

In some embodiments, a display module 2618 can continuously scan its one or more associated output packet queues 2906 for new packets. Where the display module 2618 is associated with a single output packet queue 2906, each time the display module 2618 detects a new packet, it may display the packet on a display device. However, where the display module 2618 is associated with multiple output packet queues 2906, the display module 2618 may not immediately display a new packet detected in a particular output packet queue 2906. This is because display module 2618 can be designed to synchronize the display of multiple signals.

In some embodiments, where a given display module 2618 is designed to synchronize the display of multiple signals, the display module 2618 can detect a new packet in a particular output packet queue 2906. The display module 2618 can then determine the tag associated with the new packet. The display module 2618 can use this determined tag to synchronize the display of new packets from the other output packet queues 2906. For example, display module 2618 can wait to display any packets to the display device until after detecting new packets at the other output packet queues 2906 that have the same determined tag. Once display module 2618 detects new packets having the same tag at its other associated output packet queues 2906, the display module 2618 can simultaneously display the packets from its associated output packet queues 2906. The display module 2618 can display the multiple signals in a non-overlapping stackable format. Because the display module 2618 can display packets having the same tag, the resulting displayed signals may be time-aligned.

A display module 2618 can maintain the current active tag to display in packet index 3004. Upon detecting a new packet in a particular output packet queue 2906, the display module 2618 can determine the tag of the new packet. Display module 2618 can then set packet index 3004 to the determined tag.

A display module 2618 can include display settings 3006. Display settings 3006 can include one or more parameters that control how display module 2618 displays its one or more associated signals. Display settings 3006 can specify colors to display the one or more associated signals. Display settings 3006 can specify a view format such as a waterfall view, dynamic view, or triggered view as discussed below. Display settings 3006 can specify a sweep speed for the one or more signals. Display settings 3006 can contain various other types of display settings as would be appreciated by a person of ordinary skill in the art. Display settings 3006 can be designed by a user as discussed below.

Review module 2624 can display one or more signals processed by one or more signal modules 2614 at a previous point in time. This can enable a user (e.g., a physician) to analyze the one or more signals long after they have been generated and displayed. In some embodiments, review module 2624 can capture a display of one or more signals in a display module 2618 in response to a command. For example, a user can click a button in a GUI to capture the current display of a display module 2618. The captured display can include the previously displayed visualization of the one or more signals at the time of capture. In some embodiments, the display module 2618 can pause its display of new packets in response to the capture of its current display.

In some embodiments, review module 2624 can capture the display of the one or more signals in the display module 2618 by determining a capture configuration of the display module 2618. The capture configuration can include the one or more active signals modules 2614 for the display module 2618, the capture time, the selected view for the display module 2618, the color scheme for the one or more displayed signals, and various other settings as would be appreciated by a person of ordinary skill in the art. After determining the capture configuration, review module 2624 can apply the capture configuration to previously stored signal samples.

As discussed above, input module 2604 can store one or more signal samples for each base signal in a storage for later analysis by review module 2624. Review module 2624 can capture a display of the one or more signals in the display module 2618 by applying the determined capture configuration to these stored signal samples. Specifically, review module 2624 can select the stored signal samples at the capture time in the capture configuration. Review module 2624 can then process the selected signal samples using the active signal modules 2614 in the capture configuration. Review module 2624 can also display the selected signal samples using the selected view, the color scheme, and various other settings in the capture configuration. Thus, review module 2624 can enable a user to review one or more processed signals for a display module 2618 at a particular point in time, and subject to a particular configuration.

In some embodiments, review module 2624 can enable a user to change the reviewed interval for a display module 2618. For example, the user can "rewind" to a different point in time in the past (e.g., 5 minutes ago). After the capture time is changed, review module 2624 can display the one or more processed signals for the display module 2618 at the new review time index.

Figure 31:
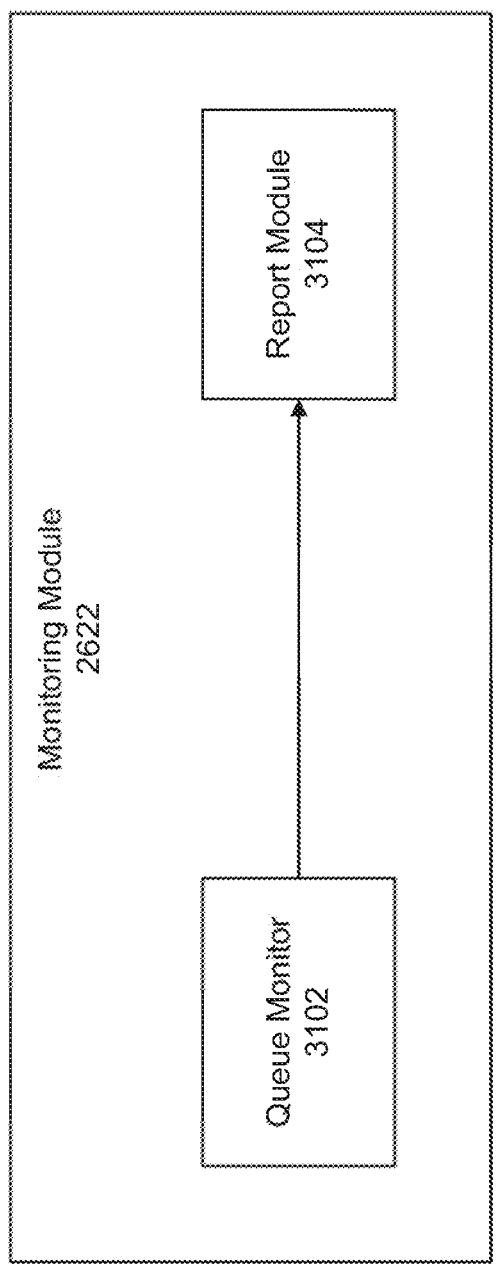
FIG. 31 is a block diagram of a monitoring module for performing error checking, according to some embodiments.

FIG. 31 is a block diagram of monitoring module 2622, according to some embodiments. Monitoring module 2622 includes queue monitor 3102 and report module 3104. Queue monitor 3102 and report module 3104 can be software modules capable of being executed by a processor (or processors) such as processor 5004.

Monitoring module 2622 can be continuously executed while signal path module 2602 is being executed. For example, monitoring module 2622 can be executed as a separate thread of execution by a processor. Monitoring module 2622 can determine whether there are issues in the execution of signal path module 2602.

In some embodiments, queue monitor 3102 can periodically scan queues in the signal path module 2602. For example, queue monitor 3102 can scan the queues 2702 in queuing module 2608. Queue monitor 3102 can also scan the input packet queues 2902 and the output packet queues 2906 in the one or more signal modules 2614. Queue monitor 3102 can determine the status of each queue during the scan. For example, queue monitor 3102 can determine the length of each queue during the scan. In some embodiments, if queue monitor 3102 determines a queue has an error status, queue monitor 3102 can request report module 3104 to display the error status on a display device. For example, queue monitor 3102 can determine that a queue's length is continuously increasing. In response, queue monitor 3102 can request report module 3104 to display an error that indicates that the particular queue has an incorrect length.

Figure 32:
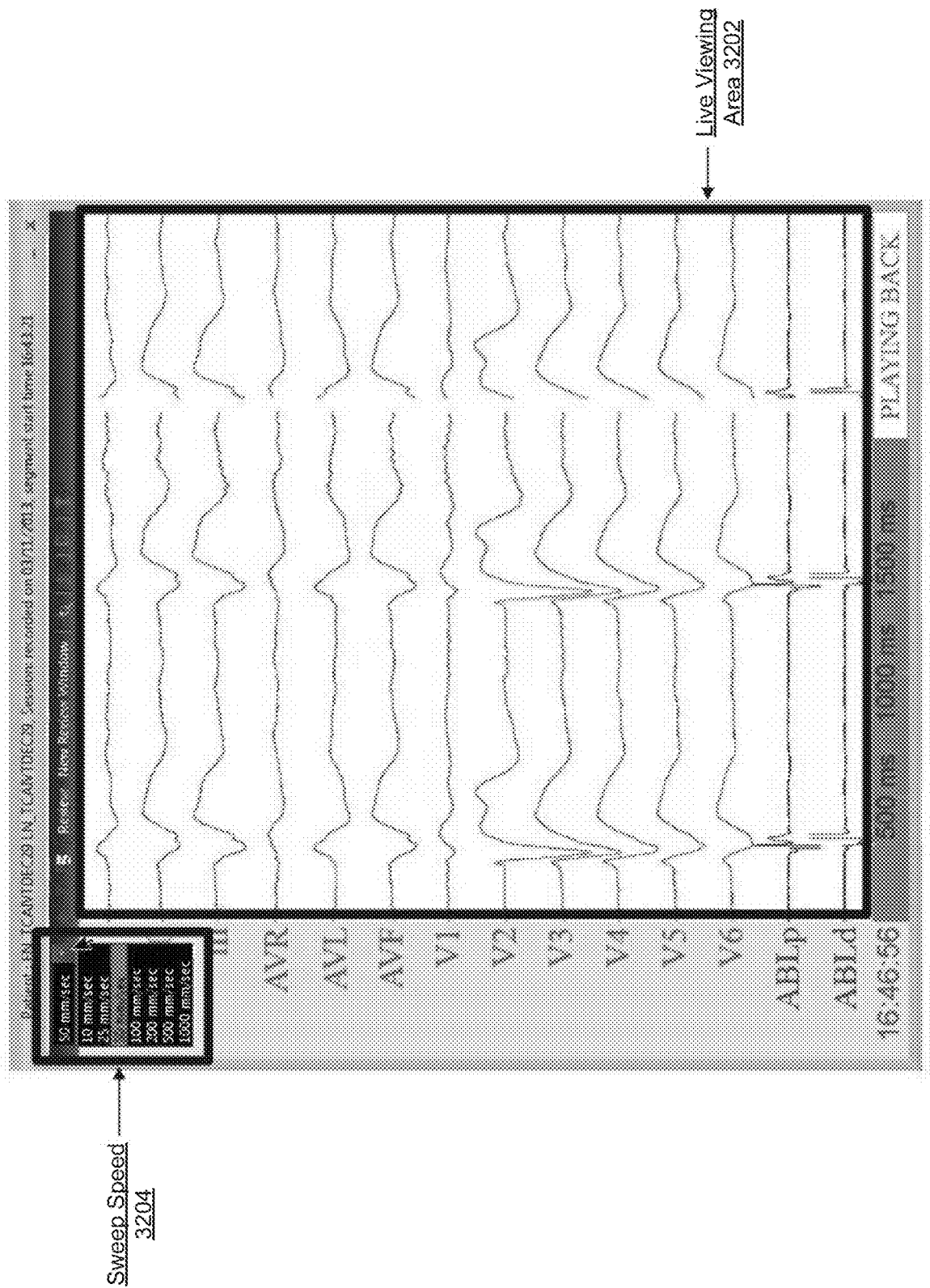
FIG. 32 illustrates an example adjustment of a sweep speed for a display module, according to some embodiments.

FIG. 32 illustrates an example adjustment of a sweep speed for a display module 2618, according to some embodiments. FIG. 32 includes a live viewing area 3202 and a sweep speed 3204. FIG. 32 is discussed with reference to FIG. 26.

Live viewing area 3202 can contain the near real-time display of a display module 2618. In FIG. 32, live viewing area 3202 includes the near real-time display of fourteen (14) different signals (e.g., processed or base signals).

Sweep speed 3204 can be a GUI widget that allows a user to select a sweep speed for live viewing area 3202. A sweep speed may represent a time scale of one or more signals displayed in live viewing area 3202. For example, the sweep speed may range from 10 mm per second to 1000 mm per second. In FIG. 32, sweep speed 3204 is shown being selected to be 50 mm per second. As would be appreciated by a person of ordinary skill in the art, the choice of sweep speed may influence the level of displayed detail, and therefore may be set based on the size of the display screen.

Figure 33:
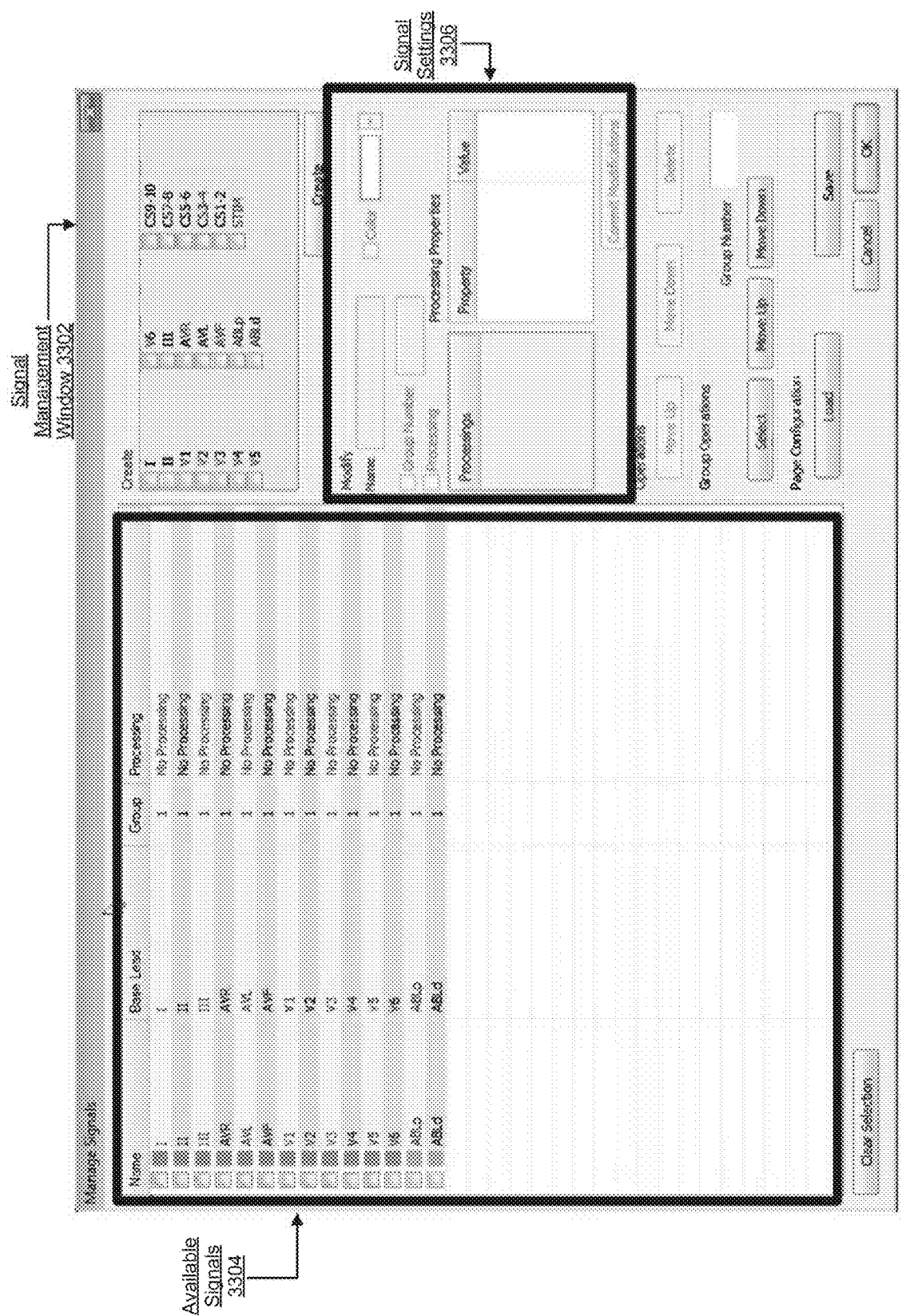
FIG. 33 illustrates signal management for a display module, according to some embodiments.

FIG. 33 illustrates signal management for a display module 2618, according to some embodiments. FIG. 33 includes a signal management window 3302. FIG. 33 is discussed with reference to FIG. 26.

Signal management window 3302 can include available signals 3304 and signal settings 3306. Available signals 3304 can contain one or more signals that can be selected for display by a display module 2618. For example, in FIG. 33, available signals 3304 contain fourteen (14) signals that can be selected for display by a display module 2618. Available signals 3304 can display various information about each signal. For example, available signals 3304 can display the name of the signal and whether the signal is processed by a particular signal module 2614.

Signal settings 3306 can display various settings that can be set for each signal. For example, in FIG. 33, signal settings 3306 enables a user to change the name of each signal or assign each signal a particular color. These settings may be stored in display settings 3006 in display module 2618. Signal settings 3306 can also enable a user to change various processing parameters associated with each signal. These processing parameters may be stored in the one or more signal processing parameters of a DSP 2904 of a signal module 2614 associated with the given signal.

Figure 34:
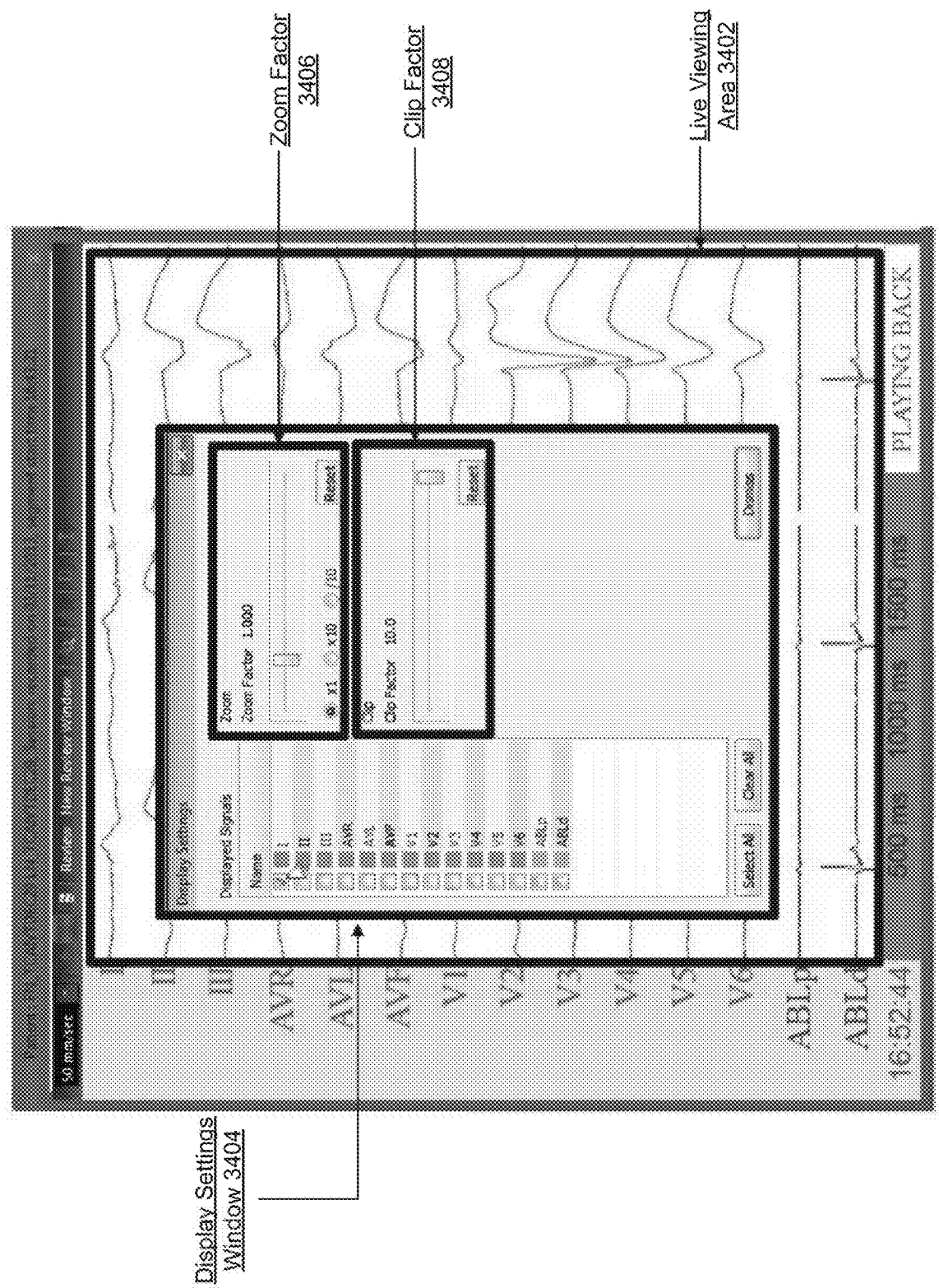
FIG. 34 illustrates an example adjustment of zoom and clip factors for a display module, according to some embodiments.

FIG. 34 illustrates an example adjustment of zoom and clip factors for a display module 2618, according to some embodiments. FIG. 34 includes a live viewing area 3402 and a display settings window 3404. FIG. 34 is discussed with reference to FIG. 26.

Live viewing area 3402 can contain the near real-time display of a display module 2618. In FIG. 34, live viewing area 3402 includes the near real-time display of fourteen (14) different signals (e.g., processed or base signals).

Display settings window 3404 can include a zoom factor 3406 and a clip factor 3408. Zoom factor 3406 can be a GUI widget to select a zoom factor for a particular signal in live viewing area 3402. The selected zoom factor can increase or decrease the size of the particular signal. For example, zoom factor 3406 can increase the size of a particular signal from 0.02 to times 40.

Clip factor 3408 can be a GUI widget permitting a user to select a clip factor for a particular signal in live viewing area 3402. The selected clip factor can control how much a signal overshoots across the display screen. For example, a user can adjust the clip factor to reduce the actual area of where the particular signal is displayed so that if the particular signal is large, it does not extend beyond the whole display screen so as to be partially unviewable.

Figure 35:
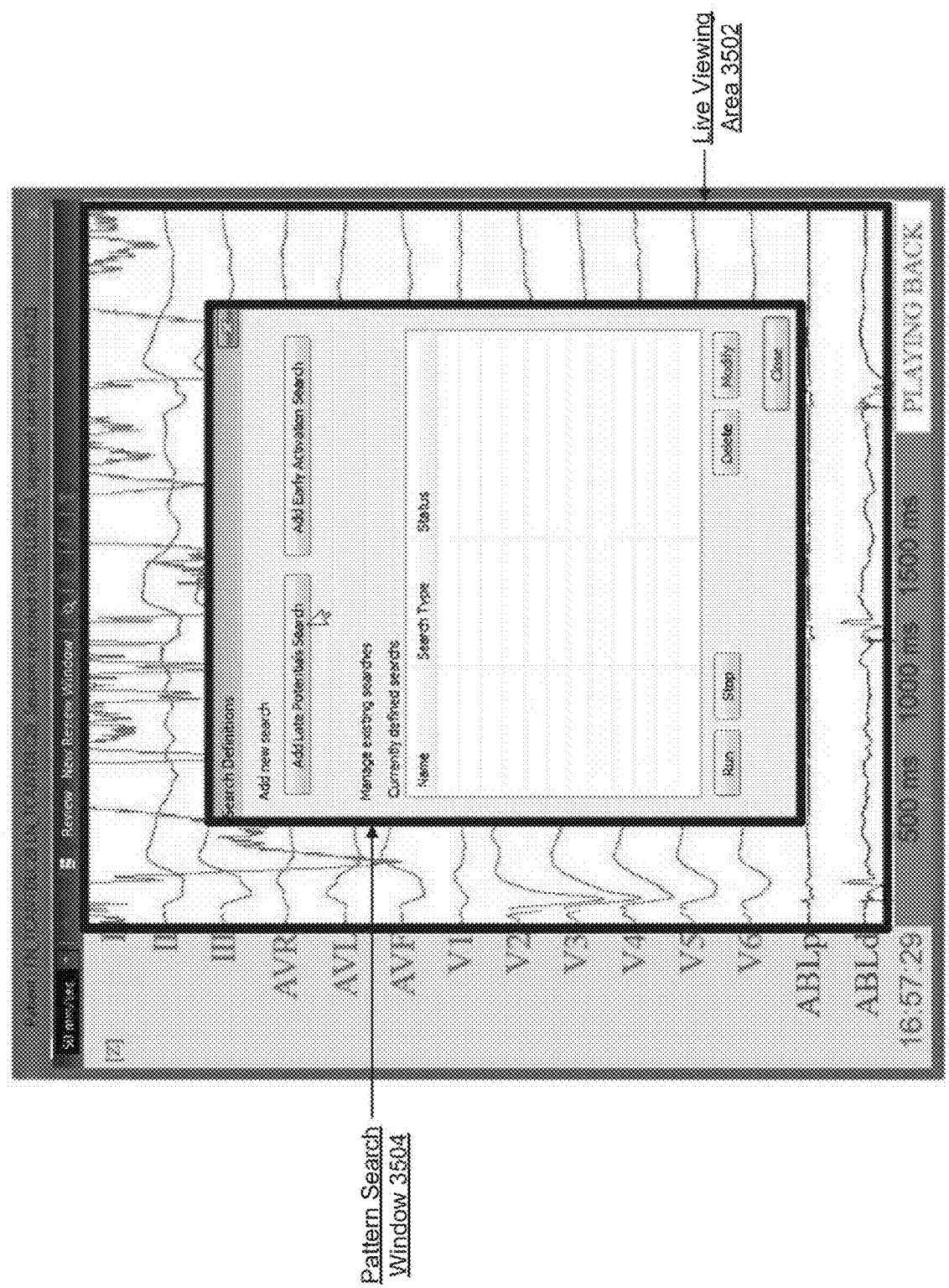
FIG. 35 illustrates pattern searching for a display module, according to some embodiments.

FIG. 35 illustrates pattern searching for a display module 2618, according to some embodiments. FIG. 35 includes a live viewing area 3502 and a pattern search window 3504. FIG. 35 is discussed with reference to FIG. 26.

Live viewing area 3502 can contain the near real-time display of a display module 2618. Pattern search window 3504 can be a GUI window that enables a user to load or specify a signal pattern to search. For example, in FIG. 35, a user may create or load a search for a late potential or early activation in one or more signals. The user may also specify various parameters for the search such as a search interval, beat detection confidence percentage, detection confidence percentage, or other parameters as would be appreciated by a person of ordinary skill in the art. The signal pattern to search for may be stored in the one or more signal processing parameters of a DSP 2904 of a signal module 2614 associated with the given signal.

Figure 36:
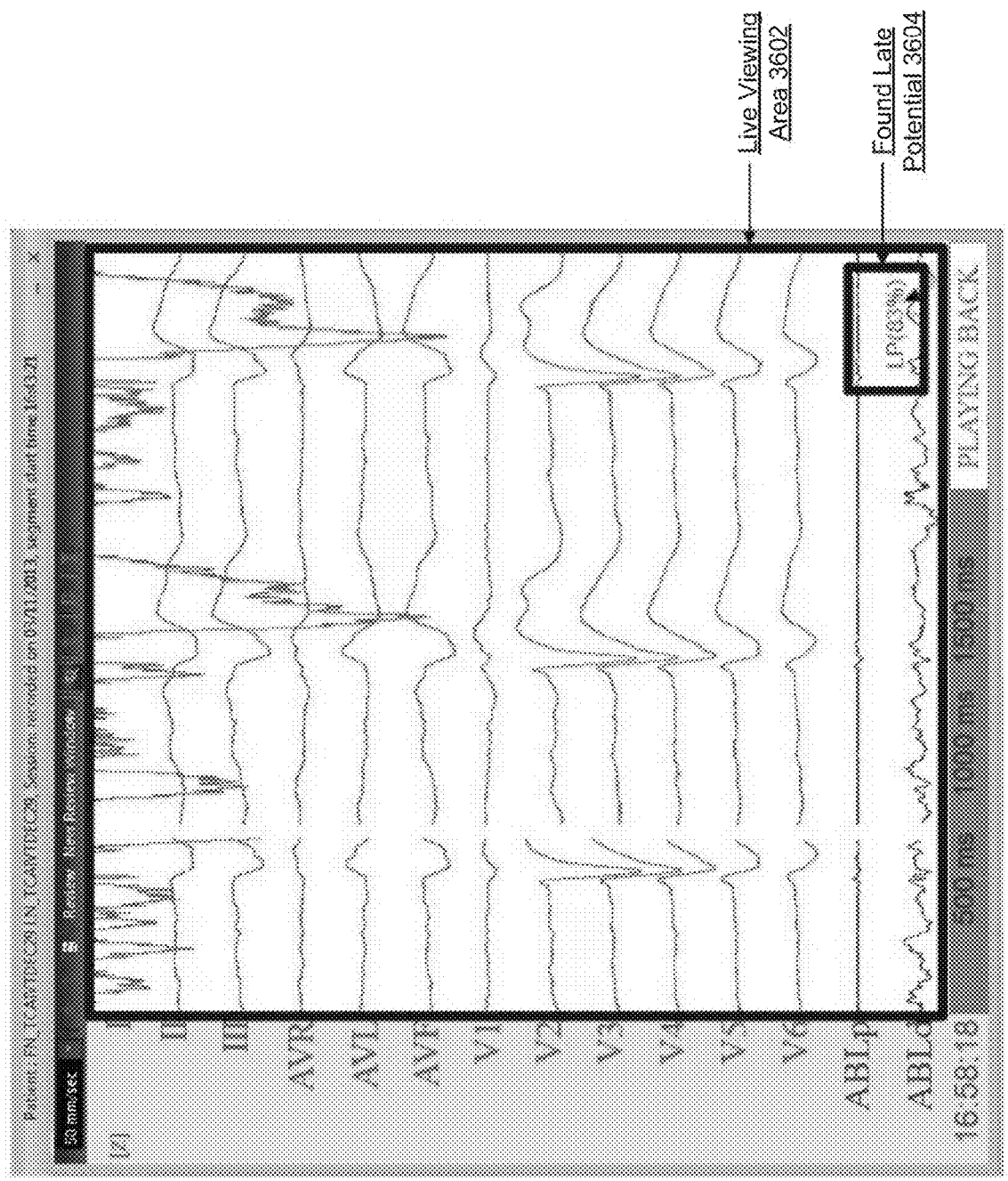
FIG. 36 illustrates a late potential search of a display of a display module, according to some embodiments.

FIG. 36 illustrates a late potential search of a display of a display module 2618, according to some embodiments. FIG. 36 includes a live viewing area 3602. FIG. 36 is discussed with reference to FIG. 26.

Live viewing area 3602 can contain the near real-time display of a display module 2618 subject to a late potential search. A user may create or load the search for the late potential as previously illustrated in FIG. 35. Once a search is initiated, live viewing area 3602 can display late potentials found in one or more signals. Live viewing area 3602 can display the found late potentials with a detection confidence percentage. For example, in FIG. 36, found late potential 3604 is shown with an 83% detection confidence. Live viewing area 3602 can also display a tally of the total late potentials found.

Figure 37A:
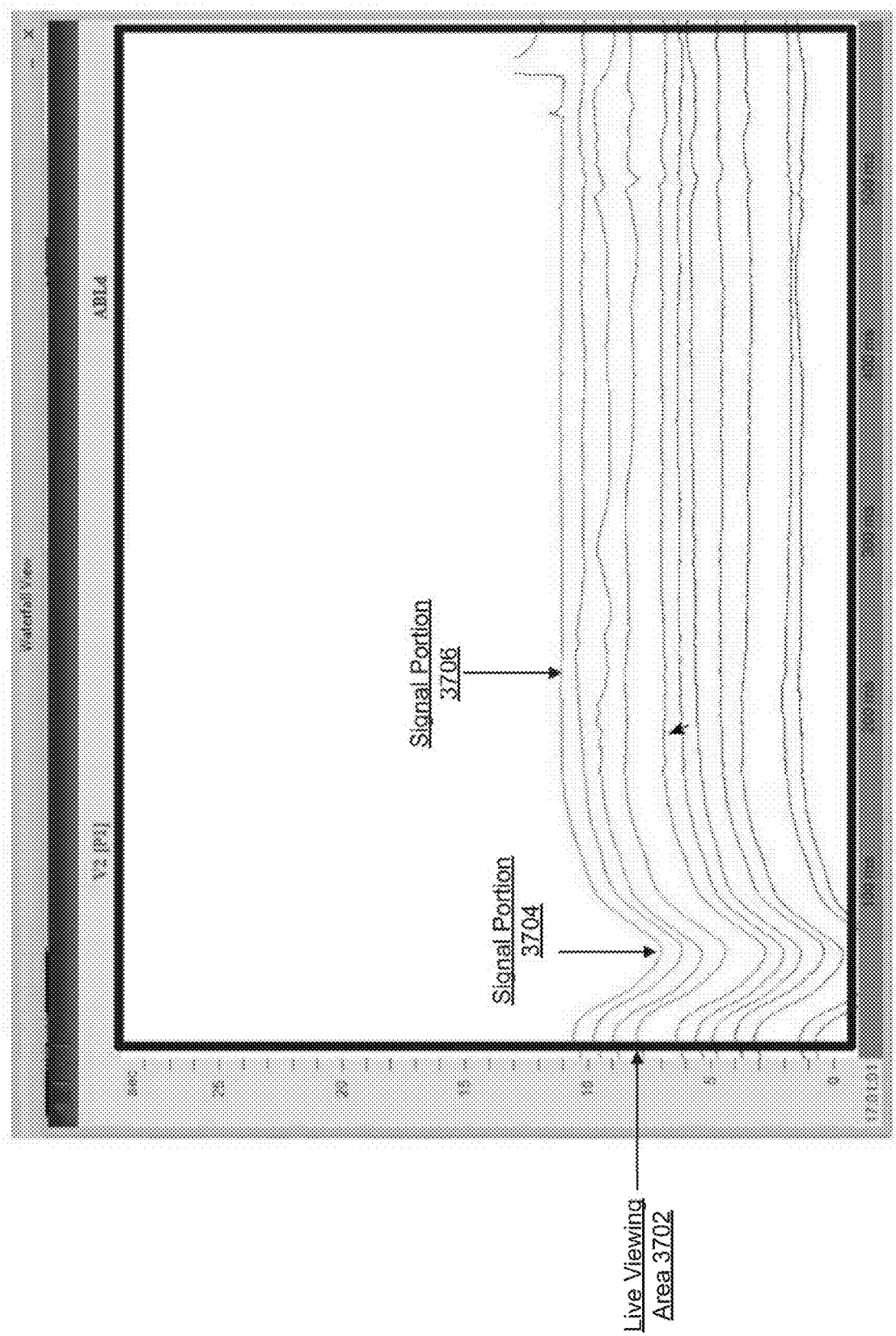
FIG. 37A illustrates using a waterfall view via a display module, according to some embodiments.

FIG. 37A illustrates using a waterfall view for a display of a display module 2618, according to some embodiments. FIG. 37A includes a live viewing area 3702. FIG. 37A is discussed with reference to FIG. 26.

Live viewing area 3702 can contain the near real-time display of a display module 2618. Live viewing area 3702 can use a waterfall view to display the near real-time display of a display module 2618. In waterfall view, signals can be displayed side by side and vertically stacked on top of each other as a pattern is matched. Specifically, a user can select a pattern to match in a first signal (e.g., a specific beat pattern). When the pattern is detected in the first signal, display module 2618 can display a portion of the first signal that matches the pattern next to the corresponding portion of a second signal (e.g., an IC signal). The user can select the size of the portion of the first signal and the size of the portion of the second signal to be displayed. For example, the user can select the size of the portion of the first signal using a time interval (e.g., 150 milliseconds).

In waterfall view, each time the pattern is detected in the first signal, display module 2618 can vertically display each new portion of the first signal that matches the pattern along with the corresponding portion of the second signal. In other words, in waterfall view, display module 2618 can display signals along a vertical time axis.

In FIG. 37A, live viewing area 3702 illustrates the near real-time display of two different signals (e.g., V2[P1] and AB1.$d$) in a waterfall view. In FIG. 37A, signals V2[P1] and AB1.$d$ are displayed side by side stacked on top of each other. For example, at around time 10 seconds, signal portion 3704 is displayed side by side with signal portion 3706. Signal portion 3704 can represent a portion of signal V2[P1] that matches a given pattern (e.g., beat P1, lead V2) at around time 10 seconds. Signal portion 3706 can represent the corresponding portion of signal AB1.$d$ at the time the given pattern matched signal V2[P1].

A user (e.g., a physician) can find waterfall view advantageous. First, waterfall view enables a user to compare corresponding portions of two signals side by side. Second, waterfall view can display signals on a display screen longer because the signals are vertically stacked. In contrast, when signals are displayed left to right, it is often difficult for a user to analyze the signals because they are no longer displayed on the display screen after a short period of time.

Figure 37B:
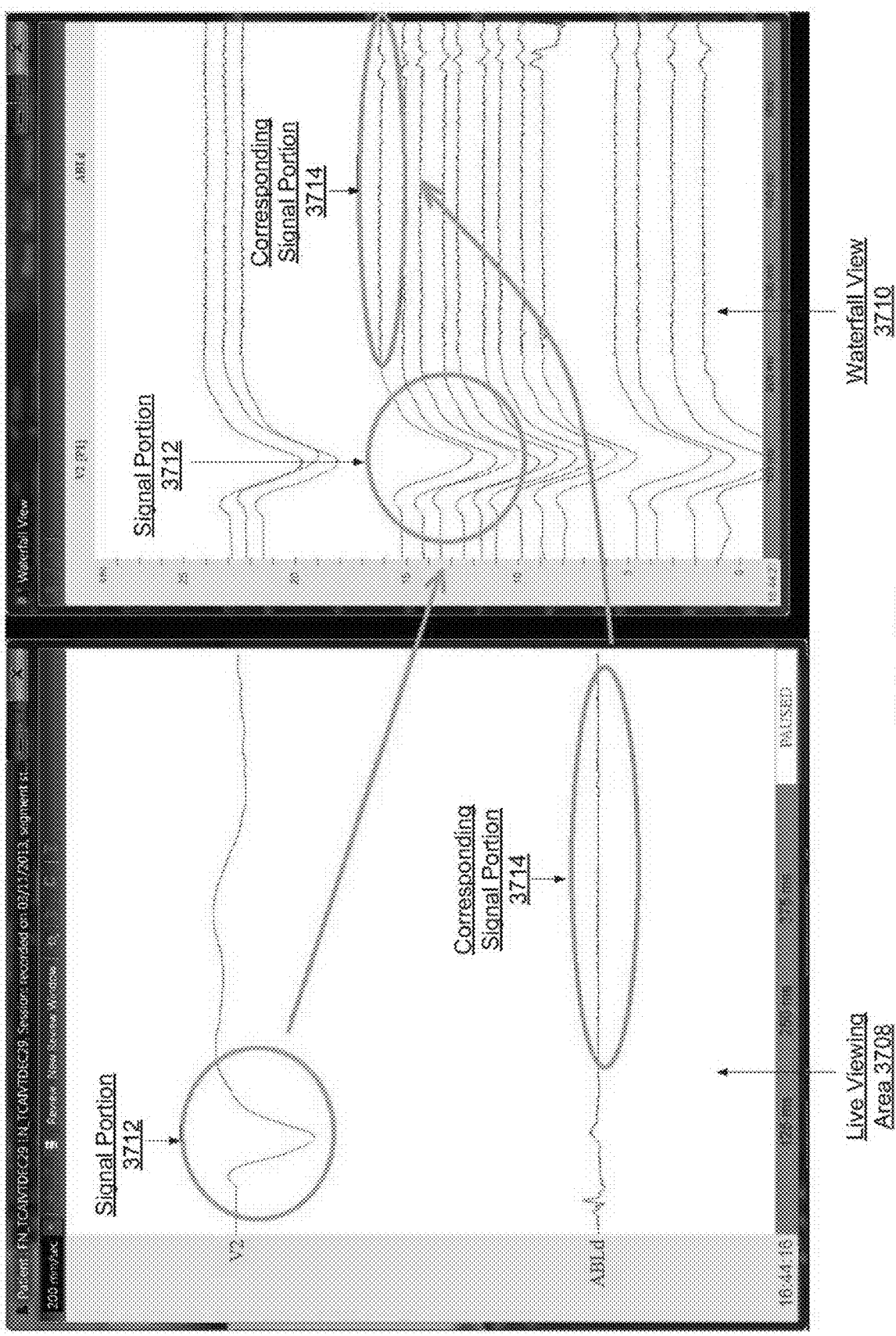
FIG. 37B illustrates using a waterfall view via a display module, according to some embodiments.

FIG. 37B illustrates using a waterfall view via display module 2618, according to some embodiments. FIG. 37B includes a live viewing area 3708 and a waterfall view 3710. FIG. 37B is discussed with reference to FIG. 26.

In FIG. 37B, live viewing area 3708 illustrates the near real-time display of two different signals (e.g., V2[P1] and AB1.$d$). Waterfall view 3710 illustrates the near real-time display of the same two signals, except signals V2[P1] and AB1.$d$ are displayed side by side so as to appear stacked on top of each other. In waterfall view 3710, each time a signal pattern in a signal is detected, display module 2618 can vertically display the portion of the signal that matches the signal pattern along with the corresponding portion of a second signal.

For example, in FIG. 37B, signal portion 3712 of signal V2[P1] contains a signal pattern. Corresponding signal portion 3714 of signal AB1.$d$ corresponds to signal portion 3712 at the time of detection. In FIG. 37B, waterfall view 3710 displays signal portion 3712 and corresponding signal portion 3714 side by side (e.g., together) each time the signal pattern is detected in signal V2[P1]. In FIG. 37B, waterfall view 3710 displays a portion of signal V2[P1] that matches the signal pattern along with a corresponding portion of signal AB1.$d$ from oldest to newest. In other words, in FIG. 37B, waterfall view 3710 displays beats that scroll up in time with the oldest beats at the top and the newest beats at the bottom. As would be appreciated by a person of ordinary skill in the art, waterfall view 3710 can display the beats in various other ways such as newest beats at the top and oldest beats at the bottom.

Figure 37C:
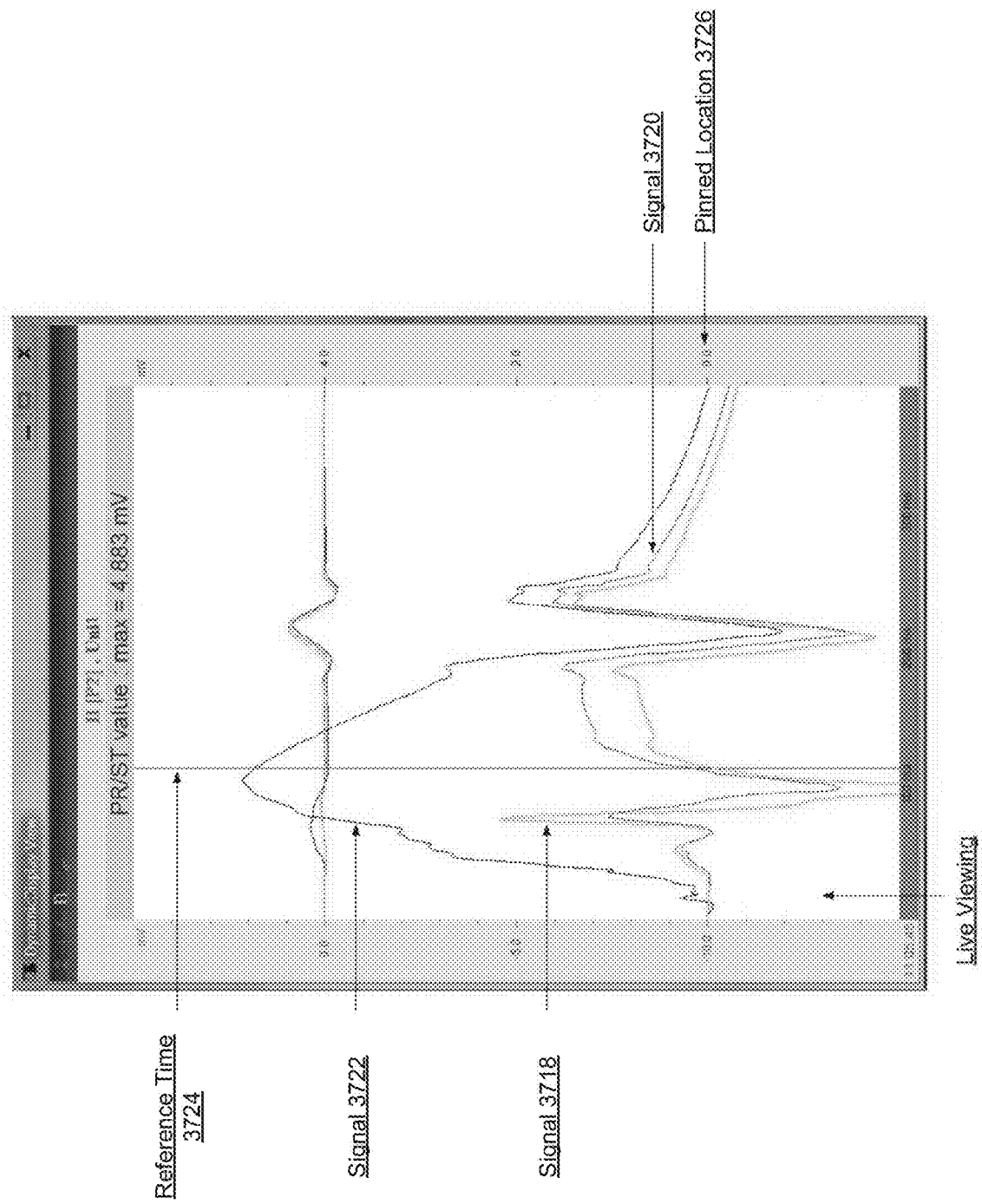
FIG. 37C illustrates using a dynamic view via a display module, according to some embodiments.

FIG. 37C illustrates using a dynamic view for a display of a display module 2618, according to some embodiments. FIG. 37C includes a live viewing area 3716. FIG. 37C is discussed with reference to FIG. 26.

Live viewing area 3716 can contain the near real-time display of a display module 2618. Live viewing area 3716 can use a dynamic view to display the near real-time display of a display module 2618. In dynamic view, a user can select a trigger for a signal (e.g., a correlation with a stored beat). The user can select the trigger from a plurality of trigger types. A trigger type can be a signal characteristic of interest that is associated with a secondary event of interest. When the trigger occurs, display module 2618 can dynamically adjust the offset of the signal so that it is pinned to a baseline. This can prevent the signal from progressing off the display screen. This is often important in clinical settings where the height of a signal peak can indicate a particular type of injury, and a signal plateau can indicate the effectiveness of an ablation lesion, for example.

In FIG. 37C, live viewing area 3716 illustrates a reference beat measured on a unipolar signal (e.g., Uni1) at a reference time (e.g., reference time 3724). For example, this can occur during ablation. In FIG. 37C, signal 3718 can be the initial beat, signal 3720 can be the current beat, and signal 3722 can be the maximum recorded beat since signal Uni1 was captured at reference time 3724. As discussed, in dynamic view, a user can specify a reference location that determines a point in a signal that is pinned to a baseline. In FIG. 37C, this point is at pinned location 3726 (e.g., 0.0 mV) on the screen for signal Uni1. This can cause signal Uni1 to be offset so that it is pinned at pinned location 3726.

Figure 37D:
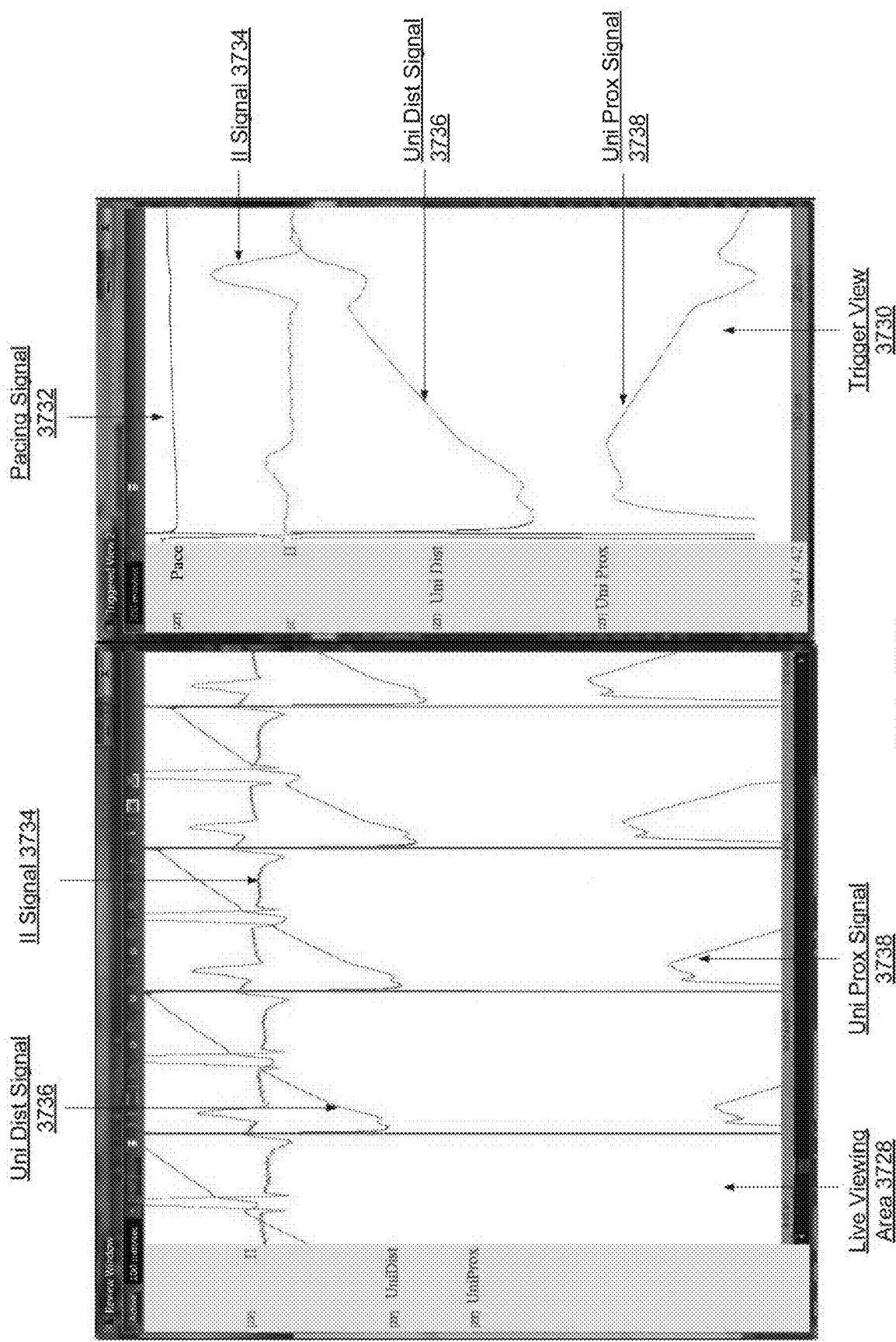
FIG. 37D illustrates using a trigger view via a display module, according to some embodiments.

FIG. 37D illustrates using a trigger view via a display module 2618, according to some embodiments. FIG. 37D includes a live viewing area 3728 and a trigger view 3730. FIG. 37D is discussed with reference to FIG. 26.

Live viewing area 3728 can contain the near real-time display of a display module 2618. In FIG. 37D, trigger view 3730 illustrates the display of live viewing area 3728 using a trigger view. In trigger view 3730, a user can select a first signal (e.g., pacing signal 3732) that triggers the display of other signals (e.g., II signal 3734, Uni Dist signal 3736, and Uni Prox signal 3738). The user can select a particular trigger for the first signal. The user can select the trigger from a plurality of trigger types. A trigger type can be a signal characteristic of interest that is associated with a secondary event of interest. For example, the user can select a particular voltage (e.g., 60 millivolts) for the first signal. A person of ordinary skill in the art would understand that other signal characteristics can be selected. When the trigger occurs, display module 2618 can display the specified one or more signals synchronized in time and stacked vertically in the display. A user (e.g., physician) can find trigger view advantageous. This is because it can enable the user to more easily view events that happen relative to an event (e.g., start of pacing signal 3732).

In trigger view 3730, a user can also specify a time after the trigger occurs where data is pinned to the baseline. For example, in FIG. 37D, the user sets the time to approximately 70 ms after the trigger occurs. In FIG. 37D, in response to user setting the time to approximately 70 ms after the trigger occurs, Uni Dist signal 3736 and Uni Prox signal 3738 are pinned and always in view in trigger view 3730. In contrast, in FIG. 37D, Uni Dist signal 3736 and Uni Prox signal 3738 are not in view in live viewing area 3728 because they are not pinned to a baseline.

Figure 38:
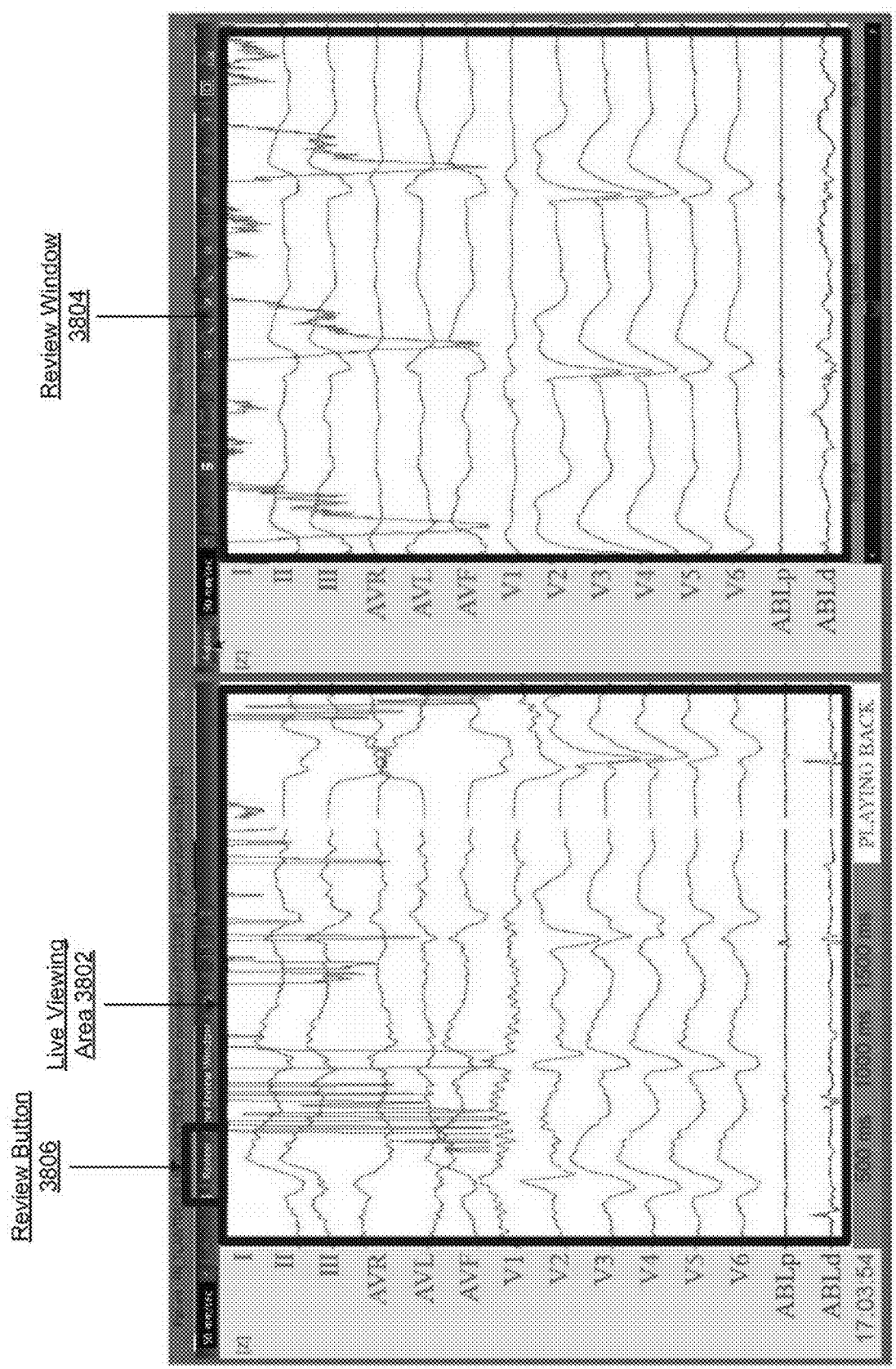
FIG. 38 illustrates the capture of a display of a display module, according to some embodiments.

FIG. 38 illustrates the capture of a display of a display module 2618, according to some embodiments. FIG. 38 includes a live viewing area 3802 and a review window 3804. FIG. 38 is discussed with reference to FIG. 26.

Live viewing area 3802 can contain the near real-time display of a display module 2618. Review window 3804 can contain a previous display shown in live viewing area 3802. To capture the display of live viewing area 3802, a user may submit a capture request. For example, in FIG. 38, a user may click Review Button 3806. In response, review module 2624 can determine a capture configuration of the display module 2618. The capture configuration can include the one or more active signals modules 2614 for the display module 2618, a capture time, a selected view for the display module 2618, a color scheme for the one or more displayed signals, and various other settings as would be appreciated by a person of ordinary skill in the art. After determining the capture configuration, review module 2624 can apply the capture configuration to previously stored signal samples and display the output in review window 3802.

Figure 39:
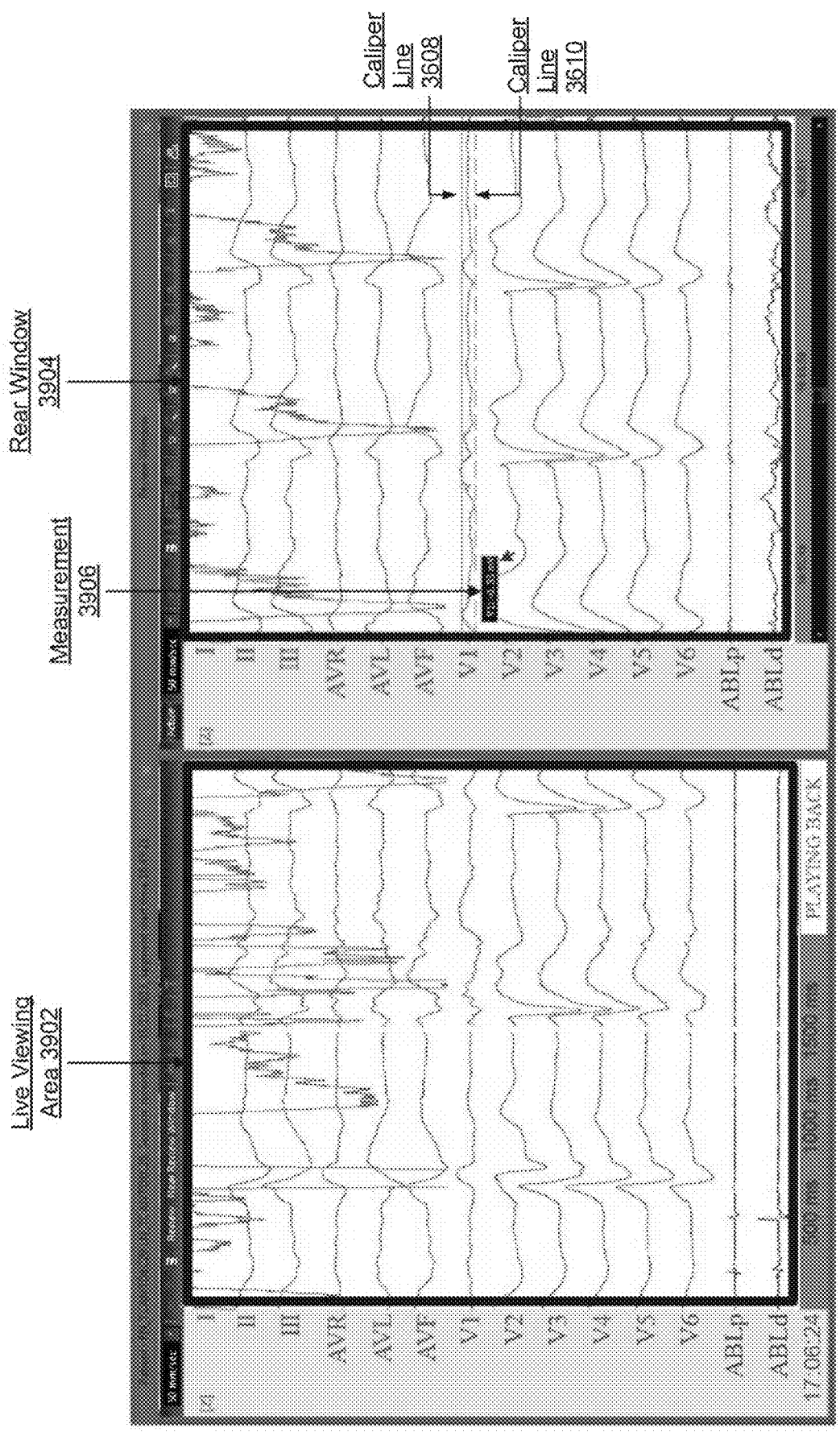
FIG. 39 illustrates the visual analyzation of a captured display of a display module, according to some embodiments.

FIG. 39 illustrates the visual analyzation of a captured display of a display module 2618, according to some embodiments. FIG. 39 includes a live viewing area 3902 and a review window 3904. FIG. 39 is discussed with reference to FIG. 26.

Live viewing area 3902 can contain the near real-time display of a display module 2618. Review window 3904 can contain a previously-captured display shown in live viewing area 3802. A user may analyze the previously-captured output in review window 3904 using vertical and horizontal calipers. Horizontal calipers can be a GUI selection widget. A user can use horizontal calipers to measure amplitude in millivolts (mV) for a particular signal. For example, as shown in FIG. 39, a user can click at the top and bottom of the V1 signal to generate two horizontal lines (e.g., caliper lines 3908 and 3910). The user may then hover the cursor along the V1 signal to display the measured amplitude at a particular point in time (e.g., measurement 3906). Similarly, vertical calipers can also be a GUI selection widget. A user can use vertical calipers to measure time in milliseconds, or beats per minute. A user can click at a left point and right point along a signal to generate two vertical lines and display the measured time, or beats per minute, between the two vertical lines.

The following method descriptions for processing and displaying multiple signals in near-real time are provided for embodiments related to ECG and IC signal visualization. A person of ordinary skill in the art would understand that these methods can apply equally to visualization of other small physiologic signals.

Figure 40:
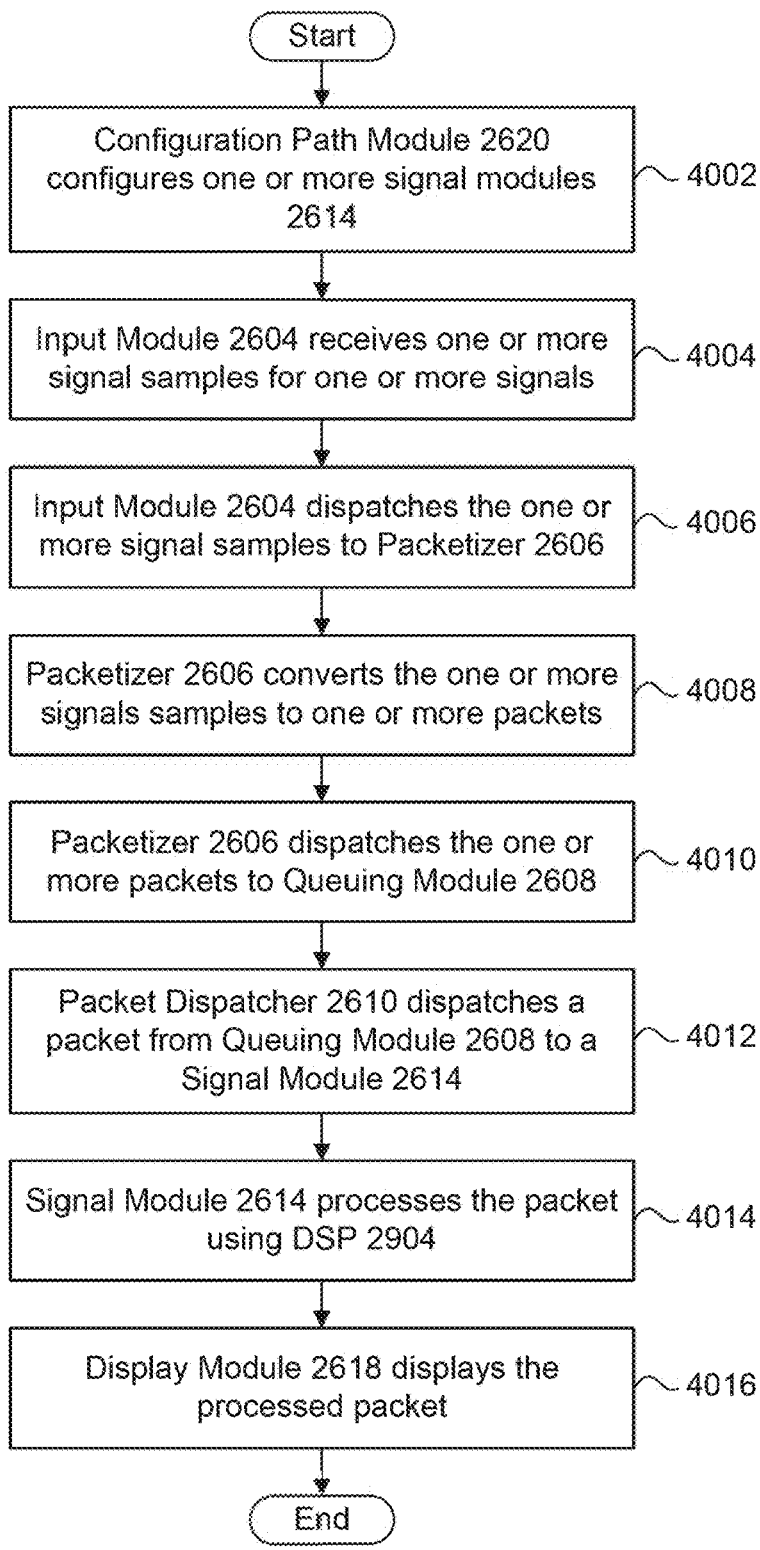
FIG. 40 is a flowchart for a method for processing and displaying multiple signals in near real-time, according to an embodiment.

FIG. 40 is a flowchart for a method 4000 for processing and displaying multiple signals in near real-time, according to some embodiments.

Method 4000 shall be described with reference to FIG. 26. However, method 4000 is not limited to that example embodiment.

Figure 41:
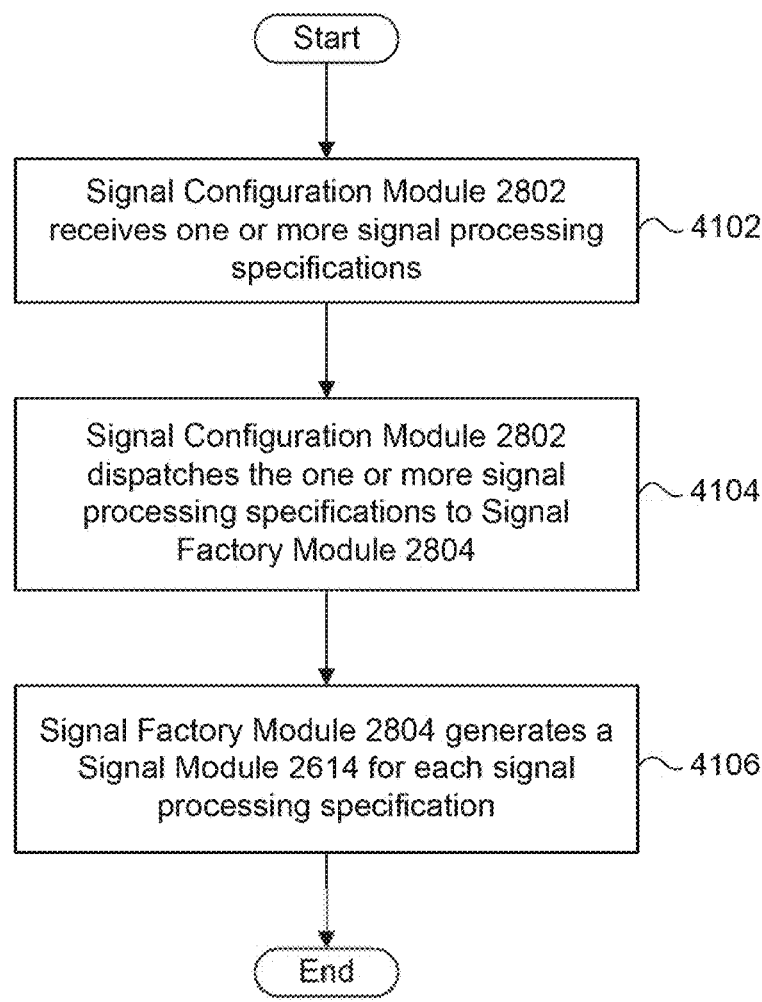
FIG. 41 is a flowchart for a method for configuring one or more signal modules, according to some embodiments.

In 4002, configuration path module 2620 configures one or more signal modules 2614. 4002 can be performed by method 4100 in FIG. 41.

In 4004, input module 2604 receives one or more signal samples for one or more signals. For example, input module 2604 can receive one or more signal samples for an IC signal, and one or more signal samples for an ECG signal. 4004 can be performed by method 4400 in FIG. 44.

In 4006, input module 2604 dispatches the one or more signal samples to packetizer 2606.

Figure 45:
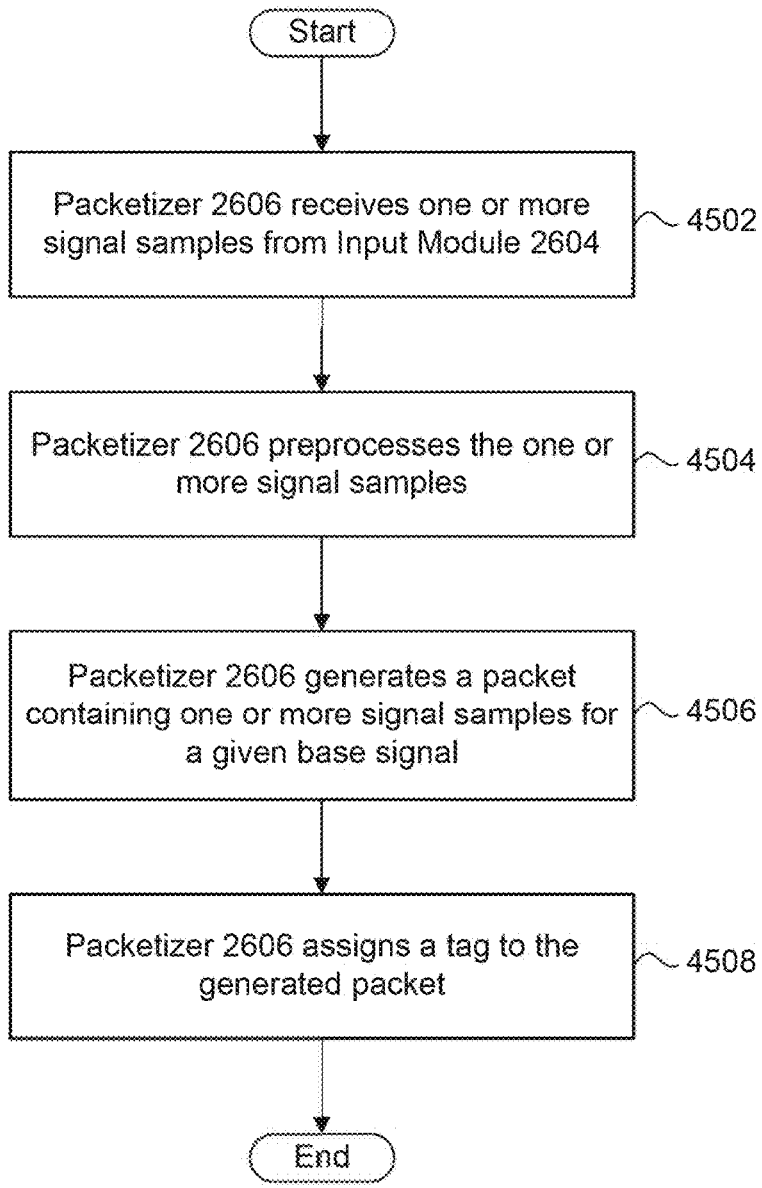
FIG. 45 is a flowchart for a method for converting one or more signal samples to one or more packets using a packetizer, according to some embodiments.

In 4008, packetizer 2606 converts the one or more signal samples to one or more packets. 4008 can be performed by method 4500 in FIG. 45.

Figure 46:
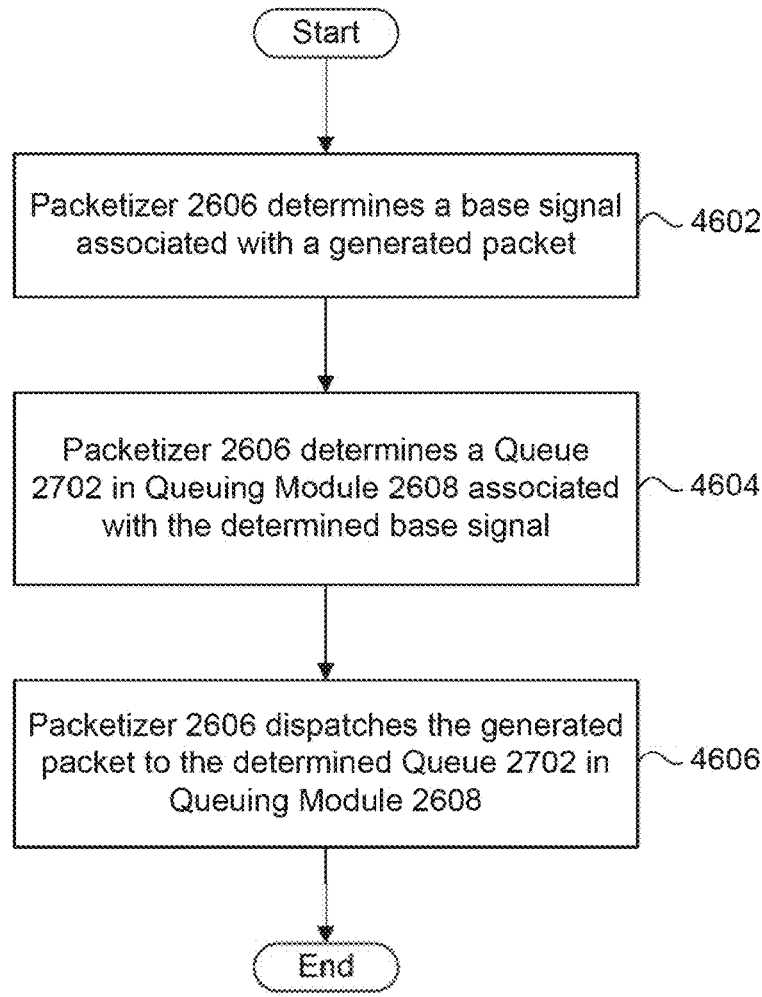
FIG. 46 is a flowchart for a method for dispatching a packet containing one or more signal samples to a queueing module, according to some embodiments.

In 4010, packetizer 2606 dispatches the one or more packets to queuing module 2608. 4010 can be performed by method 4600 in FIG. 46.

Figure 47:
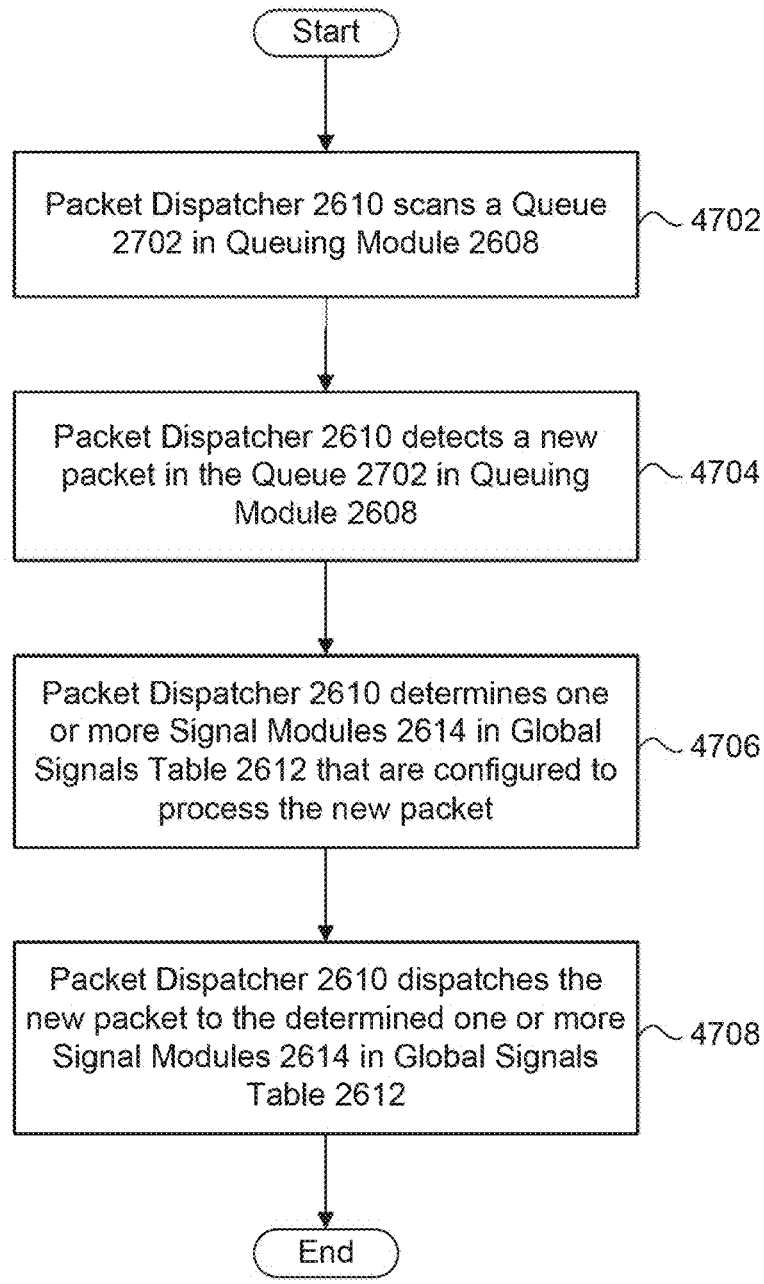
FIG. 47 is a flowchart for a method for dispatching a packet from a queuing module to a signal module associated with the packet, according to some embodiments.

In 4012, packet dispatcher 2610 dispatches a packet from queuing module 2608 to a signal module 2614 associated with the packet. 4012 can be performed by method 4700 in FIG. 47.

Figure 48:
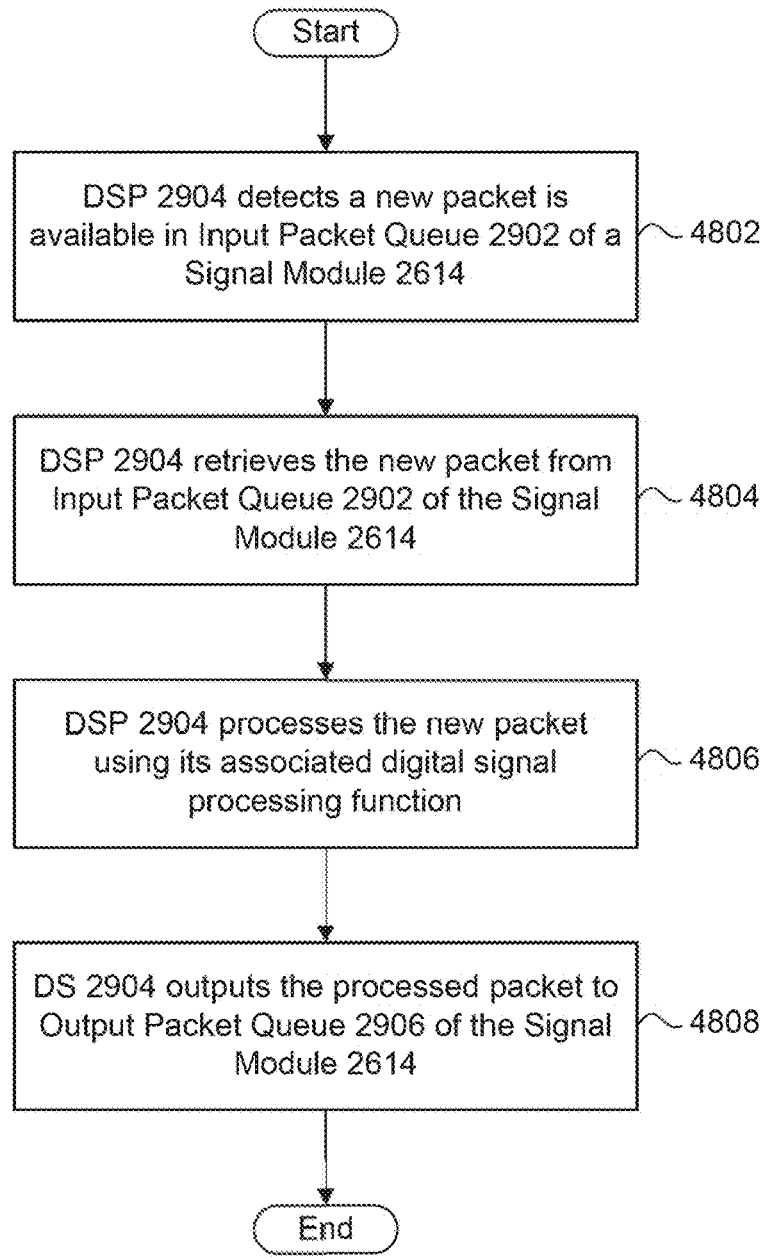
FIG. 48 is a flowchart for a method for processing a packet using a signal module associated with the packet, according to some embodiments.

In 4014, the signal module 2614 of 4012 processes the packet using a DSP 2904. 4014 can be performed by method 4800 in FIG. 48.

Figure 49:
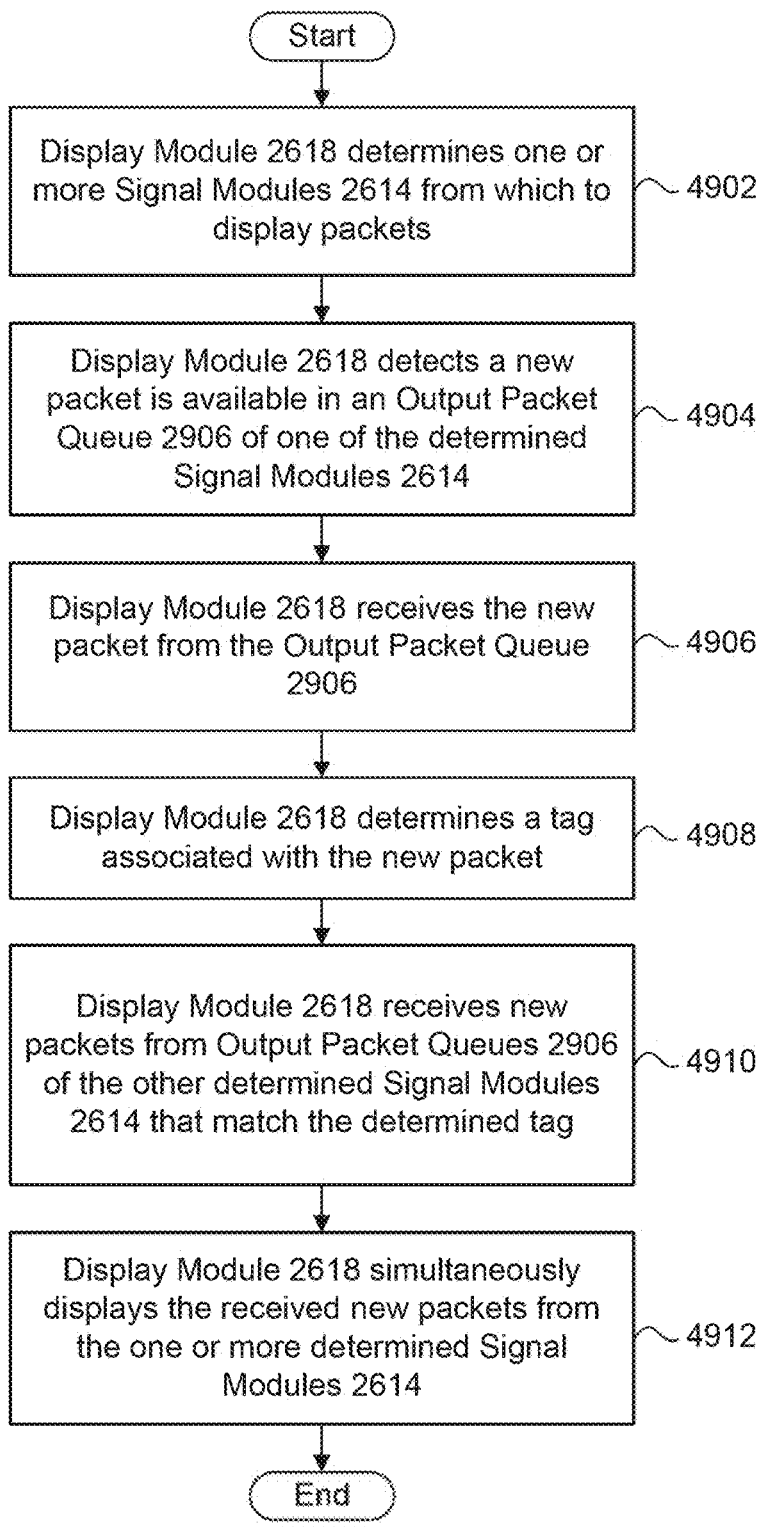
FIG. 49 is a flowchart for a method for displaying a processed packet to a display screen using a display module, according to some embodiments.

In 4016, a display module 2618 associated with the signal module 2614 of 4012 displays the processed packet to a display screen. 4016 can be performed by method 4900 in FIG. 49.

FIG. 41 is a flowchart for a method 4100 for configuring one or more signal modules 2614, according to some embodiments.

Method 4100 shall be described with reference to FIG. 26. However, method 4100 is not limited to that example embodiment.

In 4102, signal configuration module 2802 can receive one or more signal processing specifications. A signal processing specification may specify a base signal to process, the lengths of input and output packet queues for a signal module 2614, a digital signal processing function to process the base signal, and one or more associated parameters for the digital signal processing function. In some embodiments, signal configuration module 2802 can receive a signal processing specification from a file stored in memory. In some other embodiments, signal configuration module 2802 can receive a signal processing specification from a GUI that enables a user to manually enter the signal processing specification.

In 4104, signal configuration module 2802 dispatches the one or more signal processing specifications to signal factory module 2804.

Figure 42:
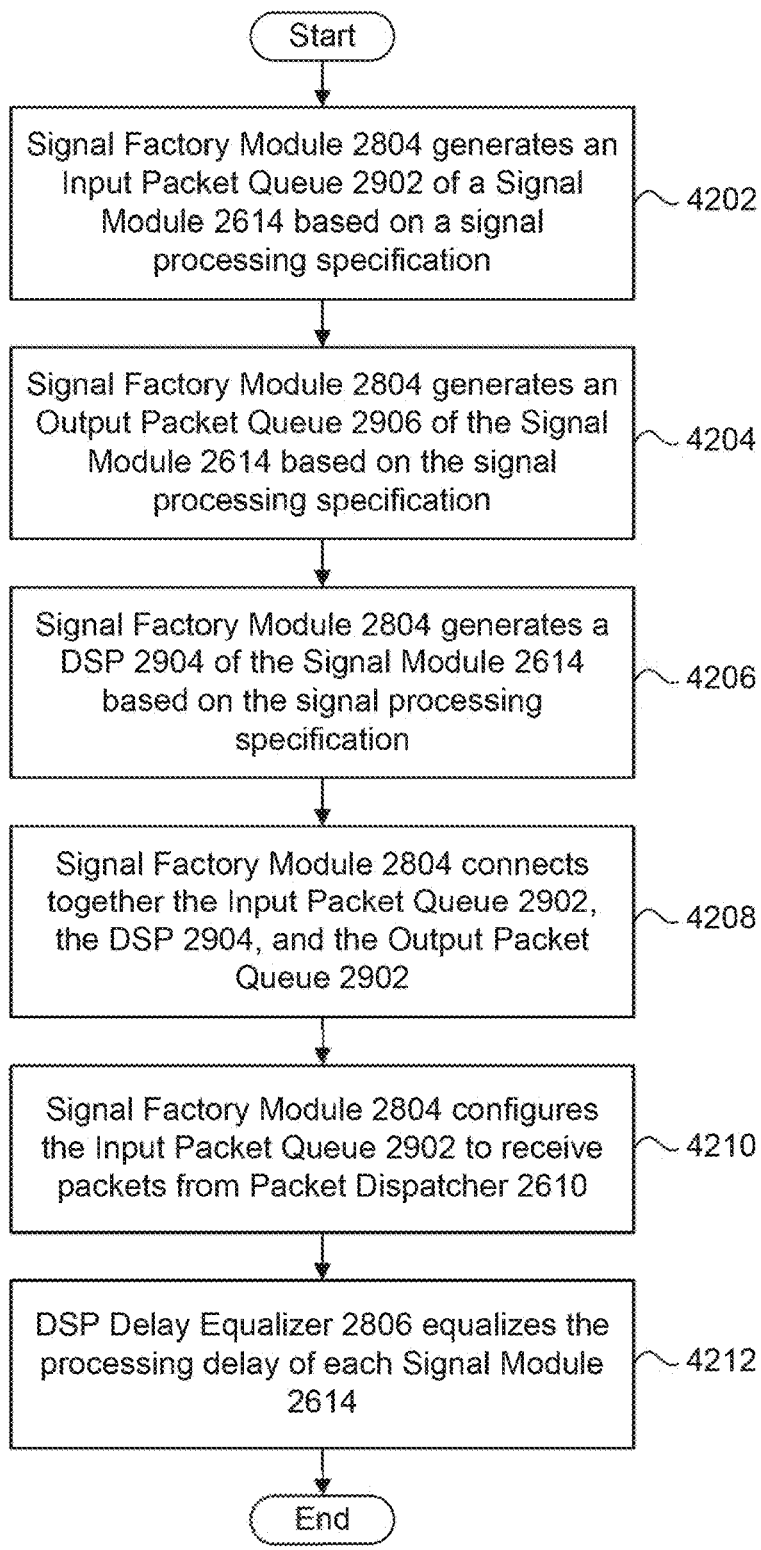
FIG. 42 is a flowchart for a method for generating a signal module from a signal processing specification, according to some embodiments.

In 4106, signal factory module 2804 generates a signal module 2614 for each signal processing specification. 4106 can be performed by method 4200 in FIG. 42.

FIG. 42 is a flowchart for a method 4200 for generating a signal module 2614 from a signal processing specification, according to some embodiments.

Method 4200 shall be described with reference to FIG. 26. However, method 4200 is not limited to that example embodiment.

In 4202, signal factory module 2804 generates an input packet queue 2902 of the signal module 2614 based on the signal processing specification in 4106 of FIG. 41. For example, signal factory module 2804 generates an input packet queue 2902 by creating a queue data structure of the length specified in the signal processing specification.

In 4204, signal factory module 2804 generates an output packet queue 2906 of the signal module 2614 based on the signal processing specification. For example, signal factory module 2804 generates an output packet queue 2806 by creating a queue data structure of the length specified in the signal processing specification.

In 4206, signal factory module 2804 generates a DSP 2904 of the signal module 2614 using DSP factory module 2808 based on the signal processing specification. Specifically, signal factory module 2804 can request DSP factory module 2808 to generate the DSP 2904 based on the digital processing function and one or more signal processing parameters specified in the signal processing specification. For example, DSP factory module 2808 can generate DSP 2904 based on a low-pass filter function and a specific cutoff frequency specified in the signal processing specification.

In 4207, signal factory module 2804 connects the generated input packet queue 2902, the generated DSP 2904, and the generated output packet queue 2906 of the signal module 2614. Specifically, signal factory module 2804 connects the output of the input packet queue 2902 to the input of DSP 2904. Signal factory module 2804 further connects the output of DSP 2904 to the input of output packet queue 2906.

In 4210, signal factory module 2804 configures input packet queue 2902 to receive packets dispatched from packet dispatcher 2610. In some embodiments, signal factory module 2804 can add a rule to a lookup table associated with packet dispatcher 2610. The rule may specify that packets associated with a given signal can be processed by a given signal module 2614.

Figure 43:
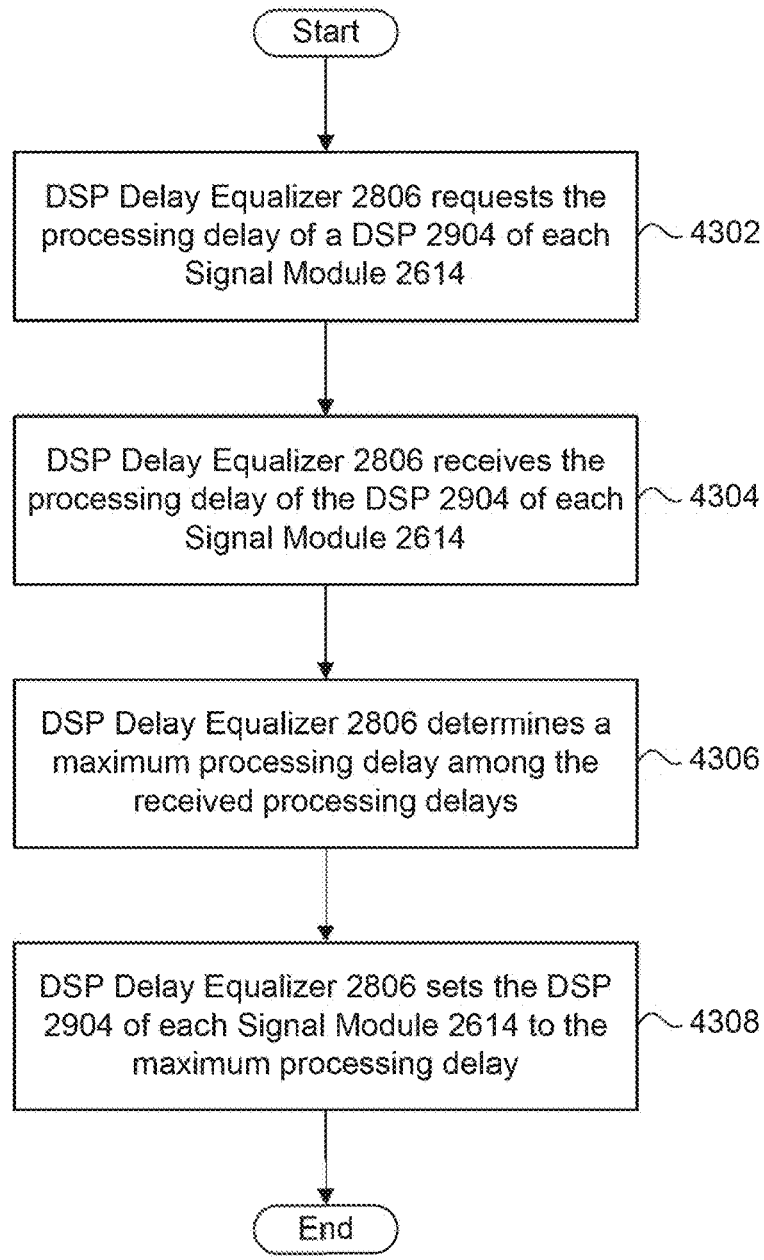
FIG. 43 is a flowchart for a method for equalizing the processing delay associated with each DSP of the one or more signal modules, according to some embodiments.

In 4212, signal factory module 2804 uses DSP delay equalizer 2806 to equalize the associated processing delays of each generated signal module 2614 such that each signal module 2614 outputs a processed packet to its output packet queue 2906 at the same time. 4210 can be performed by method 4300 in FIG. 43.

FIG. 43 is a flowchart for a method 4300 for equalizing the processing delay associated with each DSP 2904 of the one or more signal modules 2614, according to some embodiments.

Method 4300 shall be described with reference to FIG. 26. However, method 4300 is not limited to that example embodiment.

In 4302, DSP delay equalizer 2806 requests the processing delay associated with each DSP 2904 of the one or more signal modules 2614. DSP delay equalizer 2806 can request the processing delay of a DSP 2904 using an API of its associated signal module 2614.

In 4304, DSP delay equalizer 2806 receives the processing delay of a DSP 2904 from each of the one or more signal modules 2614.

In 4306, DSP delay equalizer 2806 determines a maximum processing delay among the one or more received processing delays.

In 4308, DSP delay equalizer 2806 sets a DSP 2904 of each of the one or more signal modules 2614 to the maximum processing delay. For example, DSP delay equalizer 2806 can set the processing delay of a DSP 2904 of each signal module 2614 using an API. In response, each DSP 2904 can be designed to process a packet using its digital processing function and output the processed packet to output packet queue 2906 at the end of the maximum processing delay. In some embodiments, a DSP 2904 can block its output to output packet queue 2906 if it completes processing a packet using its digital processing function prior to the end of the maximum processing delay.

Figure 44:
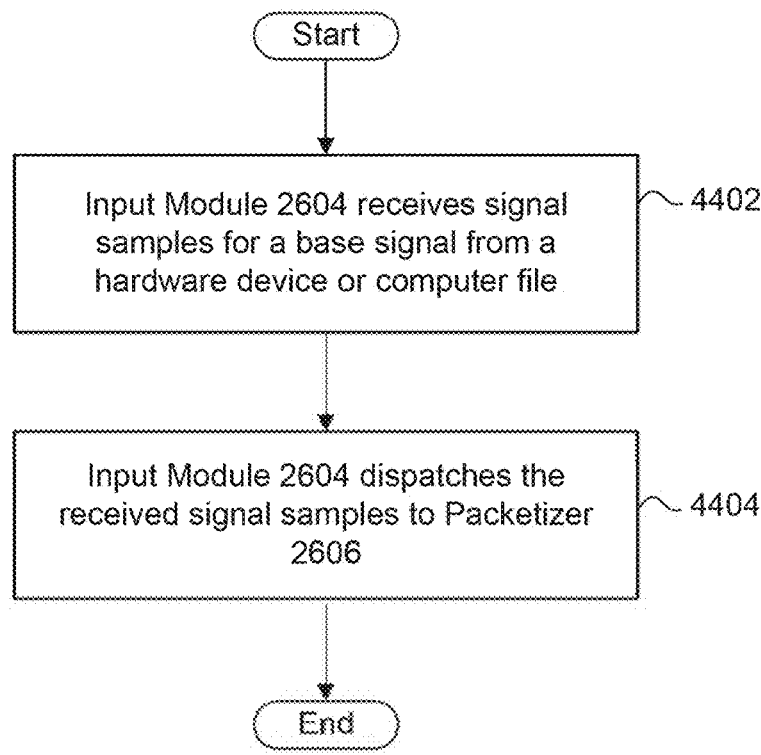
FIG. 44 is a flowchart for a method for receiving one or more signal samples for one or more signals using an input module, according to some embodiments.

FIG. 44 is a flowchart for a method 4400 for receiving one or more signal samples for one or more signals using input module 2604, according to some embodiments.

Method 4400 shall be described with reference to FIG. 26. However, method 4400 is not limited to that example embodiment.

In 4402, input module 2604 receives signal samples for a base signal from a hardware device (e.g., an electrode attached to a patient) or data stored in a computer file. For example, the computer file may contain a previously recorded session of signal samples received from a hardware device. As would be appreciated by a person of ordinary skill in the art, input module 2604 can simultaneously receive signal samples for multiple based signals.

In 4404, input module 2604 dispatches the received signal samples to packetizer 2606.

FIG. 45 is a flowchart for a method 4500 for converting one or more signal samples to one or more packets using packetizer 2606, according to some embodiments.

Method 4500 shall be described with reference to FIG. 26. However, method 4500 is not limited to that example embodiment.

In 4502, packetizer 2606 receives one or more signal samples from input module 2604.

In 4504, packetizer 2606 can optionally preprocess the one or more signal samples. For example, packetizer 2606 can convert the binary values of the one or more signal samples to their corresponding physical values. As would be appreciated by a person of ordinary skill in the art, packetizer 2606 can perform various other types of preprocessing.

In 4506, packetizer 2606 generates a packet containing the one or more signal samples for a given base signal.

Packetizer 2606 can store a predefined number of signal samples in the packet. In some embodiments, packetizer 2606 can use timer 2605 to ensure that each packet contains the same number of signal samples. Specifically, packetizer 2606 can store signal samples received from input module 2604 into the packet until timer 2605 is triggered.

In 4508, packetizer 2606 assigns a tag to the generated packet. The tag may correspond to a time period in which the one or more signal samples in the packet were received. Packetizer 2606 can assign a new tag to each subsequent packet. For example, packetizer 2606 can first generate a packet containing sixteen (16) signal samples for a given base signal. In this case, packetizer 2606 can store the first set of signal samples in a packet with a tag of 0. Packetizer 2606 can store the second set of signal samples in a packet with a tag of 15. Packetizer 2606 can store the subsequent sets of signal samples in packets with tags of 31, 47, 64, etc.

FIG. 46 is a flowchart for a method 4600 for dispatching a packet containing one or more signal samples to queueing module 2608, according to some embodiments.

Method 4600 shall be described with reference to FIG. 26. However, method 4600 is not limited to that example embodiment.

In 4602, packetizer 2606 determines a base signal associated with a newly generated packet.

In 4604, packetizer 2606 determines a queue 2702 in queuing module 2608 associated with the determined base signal. Packetizer 2606 can determine that a queue 2702 is associated with the determined base signal using a lookup table.

In 4606, packetizer 2606 dispatches the packet containing the one or more signal samples to the determined queue 2702.

FIG. 47 is a flowchart for a method 4700 for dispatching a packet from queuing module 2608 to a signal module 2614 associated with the packet, according to some embodiments.

Method 4700 shall be described with reference to FIG. 26. However, method 4700 is not limited to that example embodiment.

In 4702, packet dispatcher 2610 continuously scans a queue 2702 in queueing module 2608.

In 4704, packet dispatcher 2610 detects a new packet in the queue 2702.

In 4706, packet dispatcher 2610 determines one or more signal modules 2614 in global signals table 2612 that are designed to process the new packet. Because the new packet can be dispatched to multiple signal modules 2614 (e.g., multiple copies or "instances" of the packet), the base signal associated with the packet can be simultaneously processed using different digital processing functions of the signal modules 2614.

In some embodiments, packet dispatcher 2610 can determine one or more signal modules 2614 that are designed to process an instance of the new packet using global signals table 2612. For example, global signals table 2612 can be a fixed size array. Each element of the array can be associated with a given base signal, and thus a given a queue 2702. Moreover, each element of the array can be a fixed size array itself. Each element of this subarray can be associated with a given signal module 2614. Thus, packet dispatcher 2610 can determine one or more signal modules 2614 that are designed to process the new packet by checking the corresponding element in the subarray associated with the base signal of the new packet.

In some other embodiments, packet dispatcher 2610 can determine the one or more signal modules 2614 that are designed to process the new packet using a lookup table. Specifically, the lookup table may map the queue 2702 to one or more signal modules 2614.

In 4706, packet dispatcher 2610 dispatches the new packet to the determined one or more signal modules 2614 in global signals tables 2612 for processing. Specifically, packet dispatcher 2610 inserts the new packet into the input packet queues 2902 of the determined one or more signal modules 2614.

FIG. 48 is a flowchart for a method 4800 for processing a packet using a signal module 2614 associated with the packet, according to some embodiments.

Method 4800 shall be described with reference to FIG. 26. However, method 4800 is not limited to that example embodiment.

In 4802, DSP 2904 detects whether a new packet is available in the input packet queue 2902 of the signal module 2614. In some embodiments, DSP 2904 can scan the input packet queue 2902 for a new packet to process. In some other embodiments, DSP 2904 can get a notification that a new packet is available in the input packet queue 2902.

In 4804, DSP 2904 retrieves the new packet from input packet queue 2902 of the signal module 2614.

In 4806, DSP 2904 processes the new packet using its associated digital signal processing function. Specifically, DSP 2904 can apply its digital processing function to the one or more signal samples in the packet. In some embodiments, DSP 2904 can control how it processes the packet using its digital processing function based on one or more signal processing parameters designed for DSP 2904.

In 4808, DSP 2904 outputs the processed packet to output packet queue 2906. In some embodiments, DSP 2904 can output the processed packet to output packet queue 2906 based on its designed maximum processing delay.

FIG. 49 is a flowchart for a method 4900 for displaying a processed packet to a display screen using display module 2618, according to some embodiments.

Method 4900 shall be described with reference to FIG. 26. However, method 4900 is not limited to that example embodiment.

In 4902, display module 2618 determines what one or more signal modules 2614 from which to display processed packets. In some embodiments, display modules 2618 can determine what one or more signal modules 2614 to display processed packets from by maintaining references to the output packet queues 2906 of the one or more signal modules 2614. Display module 2618 can store the references in local signal table 3002.

In 4904, display module 2618 detects that a new packet is available in an output packet queue 2906 of one of the determined signal modules 2614.

In 4906, display module 2618 receives the new packet from the output packet queues 2906 of the one of the determined signal modules 2614.

In 4908, display module 2618 determines a tag associated with new packet.

In 4910, display module 2618 receives new packets from the other output packet queues 2906 that match the determined tag.

In 4912, display module 2618 simultaneously displays the received new packets for one or more signal modules to a display screen. Because display module 2618 displays new packets having the same tag, display module 2618 synchronizes the display of the signals associated with the new packets.

Methods 4000, 4100, 4200, 4300, 4400, 4500, 4600, 4700, 4800, 4900 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIGS. 40-49, as will be understood by a person of ordinary skill in the art.

Computer System Implementation

Various embodiments can be implemented, for example, using one or more well-known computer systems, such as computer system 5000 shown in FIG. 50. One or more computer systems 5000 can be used, for example, to implement any of the embodiments discussed herein, as well as combinations and sub-combinations thereof.

Computer system 5000 can include one or more processors (also called central processing units, or CPUs), such as a processor 5004. Processor 5004 can be connected to a communication infrastructure or bus 5006.

Computer system 5000 can also include user input/output device(s) 5003, such as monitors, keyboards, pointing devices, etc., which can communicate with communication infrastructure 5006 through user input/output interface(s) 5002.

One or more of processors 5004 can be a graphics processing unit (GPU). In an embodiment, a GPU can be a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 5000 can also include a main or primary memory 5008, such as random access memory (RAM). Main memory 5008 can include one or more levels of cache. Main memory 5008 can have stored therein control logic (e.g., computer software) and/or data.

Computer system 5000 can also include one or more secondary storage devices or memory 5010. Secondary memory 5010 can include, for example, a hard disk drive 5012 or a removable storage device or drive 5014. Removable storage drive 5014 can be a floppy disk drive, a magnetic tape drive, a compact disk drive, an optical storage device, tape backup device, or any other storage device/drive.

Removable storage drive 5014 can interact with a removable storage unit 5018. Removable storage unit 5018 can include a computer usable or readable storage device having stored thereon computer software (control logic) or data. Removable storage unit 5018 can be a floppy disk, magnetic tape, compact disk, DVD, optical storage disk, or any other computer data storage device. Removable storage drive 5014 can read from or write to removable storage unit 5018.

Secondary memory 5010 can include other means, devices, components, instrumentalities, or other approaches for allowing computer programs or other instructions or data to be accessed by computer system 5000. Such means, devices, components, instrumentalities, or other approaches can include, for example, a removable storage unit 5022 and an interface 5020. Examples of the removable storage unit 5022 and the interface 5020 can include a program cartridge and cartridge interface (such as that found in video game devices), a removable memory chip (such as an EPROM or PROM) and associated socket, a memory stick and USB port, a memory card and associated memory card slot, or any other removable storage unit and associated interface.

Computer system 5000 can further include a communication or network interface 5024. Communication interface 5024 can enable computer system 5000 to communicate and interact with any combination of external devices, external networks, external entities, etc. (individually and collectively referenced by reference number 5028). For example, communication interface 5024 can allow computer system 5000 to communicate with external or remote devices 5028 over communications path 5026, which can be wired or wireless (or a combination thereof), and which can include any combination of LANs, WANs, the Internet, etc. Control logic or data can be transmitted to and from computer system 5000 via communications path 5026.

Computer system 5000 can also be any of a personal digital assistant (PDA), desktop workstation, laptop or notebook computer, netbook, tablet, smart phone, smart watch or other wearable, appliance, part of the Internet-of-Things, or embedded system, to name a few non-limiting examples, or any combination thereof.

Computer system 5000 can be a client or server, accessing or hosting any applications or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); or a hybrid model including any combination of the foregoing examples or other services or delivery paradigms.

Any applicable data structures, file formats, and schemas in computer system 5000 can be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas can be used, either exclusively or in combination with known or open standards.

In some embodiments, a tangible, non-transitory apparatus or article of manufacture including a tangible, non-transitory computer useable or readable medium having control logic (software) stored thereon can also be referred to herein as a computer program product or program storage device. This includes, but is not limited to, computer system 5000, main memory 5008, secondary memory 5010, and removable storage units 5018 and 5022, as well as tangible articles of manufacture embodying any combination of the foregoing. Such control logic, when executed by one or more data processing devices (such as computer system 5000), can cause such data processing devices to operate as described herein.

Based on the teachings contained in this disclosure, it will be apparent to persons skilled in the relevant art how to make and use embodiments of this disclosure using data processing devices, computer systems, or computer architectures other than that shown in FIG. 50. In particular, embodiments can operate with software, hardware, and/or operating system implementations other than those described herein.

CONCLUSION

The EP recording system disclosed herein effectively removes noise and removes or isolates unwanted large signals while preserving relevant components of raw small signals, that is, while preserving integrity of original information in an EP environment. Conventional EP systems can successfully filter out noise but may also filter out signal components with the noise that a medical team desires to see. Conventional EP systems can also generate and introduce additional noise and unwanted artifacts not originally present in the raw signals with well-meaning software filtering algorithms. Even when conventional EP systems utilize state-of-the-art noise reduction practices, conventional EP systems cannot effectively collect clean small signals with high confidence in the presence of simultaneous large-signal procedures such as defibrillation and ablation. This is because conventional EP systems do not have a comprehensive signal acquisition and filtering solution across the relevant frequency ranges—low (e.g., 0 to 100 Hz), mid (e.g., above 100 Hz to below 300 kHz), and high (e.g., above and including 300 kHz)—and cannot effectively handle simultaneous signals that differ by 100s or 1000s of orders of magnitude. In comparison, the EP recording system disclosed herein integrates and applies novel hardware circuitry, software methods, and system topologies to remove unwanted signals but preserve original signal waveforms across the relevant frequencies for signals found in an EP environment.

The disclosed EP system does not have to make tradeoffs that conventional EP systems have to make. Rather, the disclosed EP system allows aspects of hardware and software to perform in tandem, in order to simultaneously: (1) run amplifiers at high gain to see small signals, (2) prevent both clipping and saturation by minimizing destructive large-signal filtering in hardware to see the large signals at the same time, (3) process the signals, separating them from each other in independent displays, removing any remaining noise, and synchronizing separated signals, and finally (4) enable a user to manipulate and analyze both large and small signals so that signal artifacts and events can be accurately time-and-event correlated.

Figure 22A:
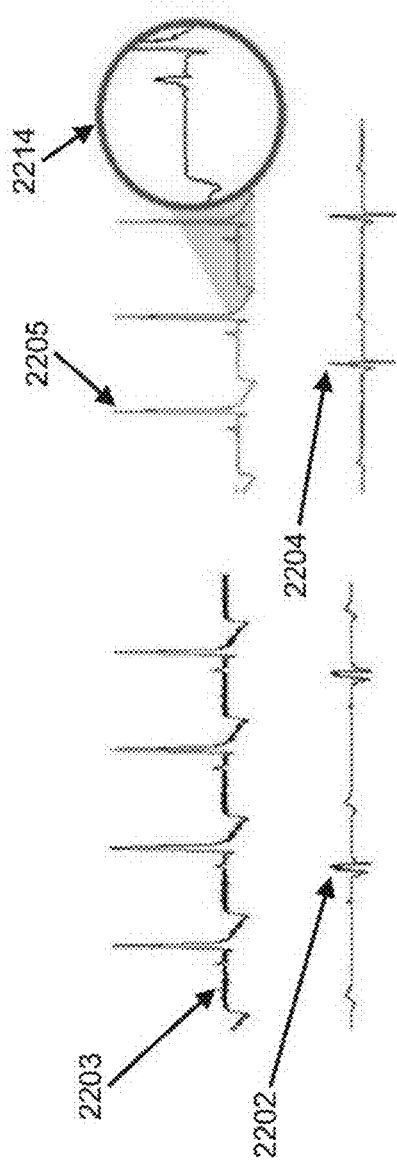
FIG. 22A illustrates the improvement in the visualization of an ECG or IC signal, according to an exemplary embodiment.
Figure 22B:
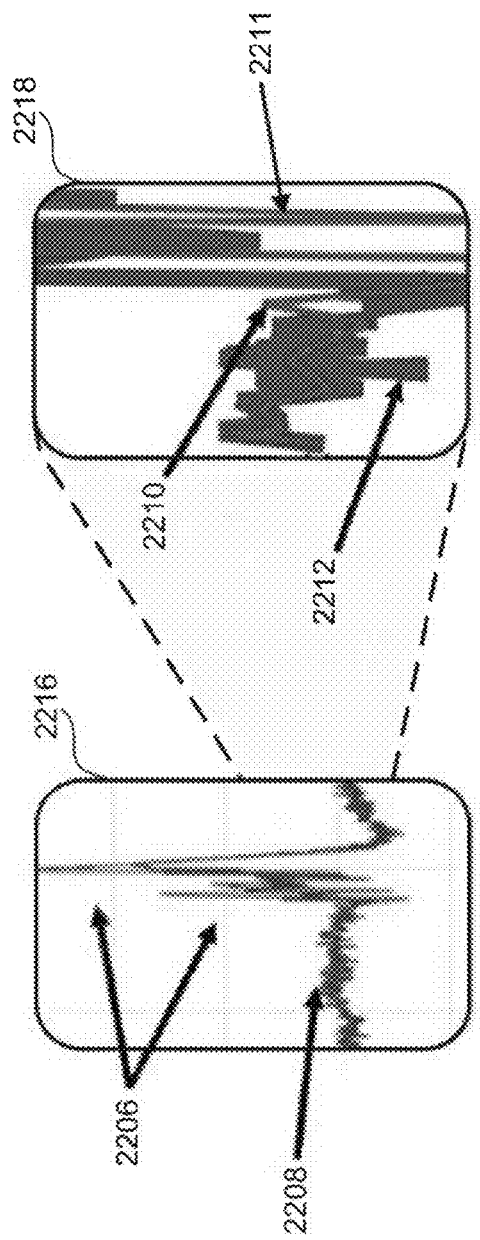
FIG. 22B illustrates the EP system's ability to reveal low-amplitude cardiac signals and micro-components of artifacts of an EP signal in the presence of noise and large-signal procedures, according to an exemplary embodiment.

The exemplary signals 2200 of FIGS. 22A-22B illustrate these concepts, showing the improvement in the visualization of an ECG or IC cardiac signal in the presence of large transients, ablation signals, defibrillation signals, and EP environment noise after being acquired, filtered, and processed by the EP system disclosed herein. FIG. 22A shows the removal of noise from both small and large signals, and the avoidance of clipping in the processing of large signals. A conventional EP system may provide a noisy cardiac signal 2203 and artificially clip a signal 2202 to limit the amplitude of a displayed signal to avoid the effects of saturation. The disclosed EP system acquires and clearly displays both weak 2214 and strong 2205 signals. With the disclosed EP system, there is no need for artificial clipping, and a strong signal 2204 is fully defined (not clipped).

FIG. 22B illustrates the EP system's ability to reveal low-amplitude cardiac signals and micro-components of relevant random artifacts of an EP signal in the presence of noise and large-signal procedures. The window 2216 illustrates a noisy signal 2208 with both the high and low-amplitude micro-components 2206 of the desired signal revealed by the disclosed EP system. In comparison, as shown in window 2218, a conventional EP system may not as successfully reveal both low and high-amplitude micro-components of the desired signal. With noisier signals, a low-amplitude micro-component 2210 of the desired signal can be revealed but is more apt to be lost amongst the noise 2212 in a conventional EP system. A high-amplitude micro-component 2211 of the desired signal may be lost by artificial clipping in a conventional EP system.

FIG. 22C illustrates the ability of the disclosed EP system to remove 60 Hz noise 2220, without saturation or delayed recovery, while preserving the component 2222 of the 60 Hz signal that belongs to the original waveform 2224. Specifically, component 2222, of the original waveform 2224, which occurs at the same time as the artifact 2220, is not lost. In other words, when large signals simultaneously overlap small signals, the disclosed EP system can identify, acquire, and process both cleanly.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, or entities illustrated in the figures or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein. This disclosure also extends to methods associated with using or otherwise implementing the features of the disclosed hardware and systems herein.

References herein to "one embodiment," "an embodiment," "an exemplary embodiment," or similar phrases, indicate that the embodiment described can include a particular feature, structure, or characteristic, but every embodiment cannot necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art to incorporate such feature, structure, or characteristic into other embodiments whether or not explicitly mentioned or described herein. Additionally, some embodiments can be described using the expression "coupled" and "connected," along with their derivatives. These terms are not necessarily intended as synonyms for each other. For example, some embodiments can be described using the terms "connected" or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A system for displaying electrocardiogram (ECG) and intracardiac (IC) signals, comprising:
   a Wilson Central Terminal (WCT) circuit configured to be coupled to three limb electrodes;
   a right-leg drive (RLD) circuit configured to be coupled to a fourth limb electrode; and
   a twin-T network, coupled to the RLD circuit, comprising a first twin-T circuit coupled to a second twin-T circuit and an operational amplifier;
   wherein a node of the first twin-T circuit is coupled to a first input of the operational amplifier, at least two of the three limb electrodes are coupled to a second input of the operational amplifier, and an output of the operational amplifier is coupled to an input of the RLD circuit, and
   wherein a node of the second twin-T circuit is coupled to the output of the operational amplifier.

2. The system of claim 1, wherein the WCT circuit provides a unipolar input reference for single catheter inputs.

3. The system of claim 1, wherein the RLD circuit is configured to remove common mode voltage from a signal received at the input of the RLD circuit.

4. The system of claim 1, wherein the RLD circuit is configured to prevent current having an amplitude greater than one microampere from flowing to the fourth limb electrode.

5. The system of claim 1, wherein the twin-T network comprises a notch filter in a feedback path of the twin-T network.

6. The system of claim 1, wherein the twin-T network is configured to provide enhanced common mode rejection of a first harmonic frequency and a third harmonic frequency of power mains.

7. The system of claim 1, wherein a first harmonic frequency is 60 Hz and a third harmonic frequency is 180 Hz.

8. The system of claim 1, wherein the RLD circuit is configured to remove a common mode voltage from a signal received from the three limb electrodes.

9. The system of claim 1, wherein the twin-T network is configured to produce a first peak and a second peak at the output of the operational amplifier, wherein the first peak has a first center frequency located at a first harmonic frequency and the second peak has a second center frequency located at a third harmonic frequency.

* * * * *